United States Patent
Hayashi et al.

(10) Patent No.: US 10,424,742 B2
(45) Date of Patent: Sep. 24, 2019

(54) ORGANIC ELECTROLUMINESCENT DEVICE

(71) Applicants: HODOGAYA CHEMICAL CO., LTD., Tokyo (JP); SFC CO., LTD., Chungcheongbuk-do (KR)

(72) Inventors: Shuichi Hayashi, Tokyo (JP); Daizou Kanda, Tokyo (JP); Shunji Mochiduki, Tokyo (JP); Se-Jin Lee, Chungcheongbuk-do (KR); Oun-gyu Lee, Chungcheongbuk-do (KR); Bong-Ki Shin, Chungcheongbuk-do (KR)

(73) Assignees: HODOGAYA CHEMICAL CO., LTD., Tokyo (JP); SFC CO., LTD, Chungcheongbuk-Do (KR)

( * ) Notice: Subject to any disclaimer, the term of this patent is extended or adjusted under 35 U.S.C. 154(b) by 0 days.

(21) Appl. No.: 15/504,804

(22) PCT Filed: Aug. 6, 2015

(86) PCT No.: PCT/JP2015/072386
§ 371 (c)(1),
(2) Date: Feb. 17, 2017

(87) PCT Pub. No.: WO2016/027687
PCT Pub. Date: Feb. 25, 2016

(65) Prior Publication Data
US 2017/0271599 A1    Sep. 21, 2017

(30) Foreign Application Priority Data

Aug. 20, 2014 (JP) ................................ 2014-167249

(51) Int. Cl.
*H01L 51/00* (2006.01)
*C09K 11/06* (2006.01)
(Continued)

(52) U.S. Cl.
CPC ........ *H01L 51/0072* (2013.01); *C07D 221/18* (2013.01); *C07D 403/04* (2013.01);
(Continued)

(58) Field of Classification Search
None
See application file for complete search history.

(56) References Cited

U.S. PATENT DOCUMENTS 5,639,914 A    6/1997  Tomiyama et al.
5,707,747 A    1/1998  Tomiyama et al.
(Continued)

FOREIGN PATENT DOCUMENTS

CN    1986645 A     6/2007
CN    103649080 A   3/2014
(Continued)

OTHER PUBLICATIONS

Machine English translation of KR 10-2011-0018195. Jan. 26, 2018.*
(Continued)

*Primary Examiner* — Jay Yang
(74) *Attorney, Agent, or Firm* — Greenblum & Bernstein, P.L.C.

(57) ABSTRACT

The organic EL device of the invention has, in order, an anode, a hole transport layer, a luminous layer, an electron transport layer and a cathode. The hole transport layer includes an indenoacridan derivative represented by the following general formula (1), and the luminous layer includes an N-aromatic substituted indenoindole compound and/or an N-aromatic substituted carbazole compound. In the formula, $A^1$ is a divalent aromatic hydrocarbon group, a divalent aromatic heterocyclic group or a single bond, B is a monovalent aromatic hydrocarbon group; a monovalent
(Continued)

1  TRANSPARENT SUBSTRATE
2  TRANSPARENT ANODE
3  HOLE INJECTION LAYER
5  HOLE TRANSPORT LAYER
5a FIRST HOLE TRANSPORT LAYER
5b SECOND HOLE TRANSPORT LAYER
6  LUMINOUS LAYER
7  ELECTRON TRANSPORT LAYER
8  ELECTRON INJECTION LAYER
9  CATHODE aromatic heterocyclic group; or a disubstituted amino group having, as a substituent, a monovalent aromatic hydrocarbon group or a monovalent aromatic heterocyclic group; and $R^1$ to $R^{14}$ each represent a hydrogen atom or an alkyl group.

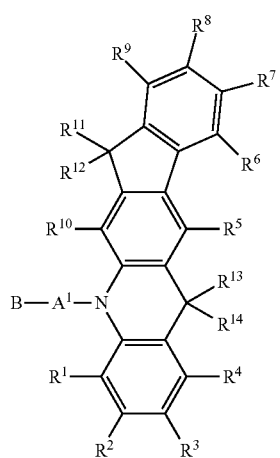

(1)

10 Claims, 47 Drawing Sheets

(51) Int. Cl.
*C07D 221/18* (2006.01)
*C07D 403/14* (2006.01)
*C07D 403/04* (2006.01)
*C07D 403/10* (2006.01)
*C07D 491/048* (2006.01)
*C07D 495/14* (2006.01)
*C09D 11/02* (2014.01)
*C07D 495/04* (2006.01)
*H01L 51/50* (2006.01)
*C09K 11/02* (2006.01)
*C07D 209/94* (2006.01)

(52) U.S. Cl.
CPC ......... *C07D 403/10* (2013.01); *C07D 403/14* (2013.01); *C07D 491/048* (2013.01); *C07D 495/04* (2013.01); *C07D 495/14* (2013.01); *C09K 11/025* (2013.01); *C09K 11/06* (2013.01); *H01L 51/0052* (2013.01); *H01L 51/0058* (2013.01); *H01L 51/0071* (2013.01); *H01L 51/0085* (2013.01); *H01L 51/50* (2013.01); *C07D 209/94* (2013.01); *C09K 2211/1007* (2013.01); *C09K 2211/1044* (2013.01); *C09K 2211/185* (2013.01); *H01L 51/5016* (2013.01); *H01L 51/5056* (2013.01); *H01L 51/5064* (2013.01)

(56) References Cited

U.S. PATENT DOCUMENTS

| | | |
|---|---|---|
| 5,792,557 A | 8/1998 | Nakaya et al. |
| 7,759,030 B2 | 7/2010 | Abe et al. |
| 7,799,492 B2 | 9/2010 | Abe et al. |
| 8,597,802 B2 | 12/2013 | Kim et al. |
| 8,845,926 B2 | 9/2014 | Shitagaki et al. |
| 2003/0165715 A1* | 9/2003 | Yoon .................. C07D 235/08 428/690 |
| 2007/0138483 A1 | 6/2007 | Lee et al. |
| 2007/0252521 A1 | 11/2007 | Kondakov et al. |
| 2012/0228598 A1* | 9/2012 | Yokoyama .......... C07D 471/04 257/40 |
| 2014/0117289 A1 | 5/2014 | Pan et al. |
| 2014/0167026 A1 | 6/2014 | Kato et al. |
| 2014/0374721 A1 | 12/2014 | Yokoyama et al. |
| 2015/0249218 A1* | 9/2015 | Yokoyama .......... C07D 401/04 257/40 |

FOREIGN PATENT DOCUMENTS

| | | |
|---|---|---|
| JP | H08-48656 A | 2/1996 |
| JP | 3194657 B2 | 7/2001 |
| JP | 2004-311411 A | 11/2004 |
| JP | 2006-219393 A | 8/2006 |
| JP | 2009-535815 A | 10/2009 |
| JP | 2009-299049 A | 12/2009 |
| JP | 2010040829 A | 2/2010 |
| JP | 4943840 B2 | 5/2012 |
| JP | 2014-519541 A | 8/2014 |
| KR | 10-2011-0018195 * | 2/2011 |
| KR | 10-2012-0084238 A | 7/2012 |
| KR | 10-1216004 B1 | 12/2012 |
| KR | 10-2014-0046771 * | 4/2014 |
| WO | 2006/033563 A1 | 3/2006 |
| WO | 2007/110228 A1 | 10/2007 |
| WO | 2010/147319 A2 | 12/2010 |
| WO | 2013/054764 A1 | 4/2013 |
| WO | 2014/034092 A1 | 3/2014 |
| WO | WO-2014/034092 A1 * | 3/2014 |
| WO | 2014/061960 A1 | 4/2014 |
| WO | WO-2014/058183 A1 * | 4/2014 |
| WO | 2014/112360 A1 | 7/2014 |
| WO | WO-2014/112360 A1 * | 7/2014 |

OTHER PUBLICATIONS

Machine English translation of Yokoyama et al. 3 (WO 2014/112360 A1). Jul. 10, 2018.*
Machine English translation of Mun et al. (KR 10-2014-0046771). Jan. 13, 2018.*
International Search Report issued with respect to Application No. PCT/JP2015/072386, dated Oct. 13, 2015.
International Preliminary Report on Patentability issued with respect to Application No. PCT/JP2015/072386, dated Feb. 21, 2017.
European Search Report issued with respect to Application No. 15834378.0, dated Dec. 8, 2017.
Chinese Office Action issued with respect to Application No. 201580044758.8, dated Dec. 1, 2017.

* cited by examiner

1  TRANSPARENT SUBSTRATE
2  TRANSPARENT ANODE
3  HOLE INJECTION LAYER
5  HOLE TRANSPORT LAYER
5a FIRST HOLE TRANSPORT LAYER
5b SECOND HOLE TRANSPORT LAYER
6  LUMINOUS LAYER
7  ELECTRON TRANSPORT LAYER
8  ELECTRON INJECTION LAYER
9  CATHODE (1-6)

(1-7)

(1-8)

(1-9)

(1-10)

(1-11)

(1-12)

(1-13)

(1-14)

(1-15)

(1-16)

(1-17)

(1-18)

(1-19)

(1-20)

(1-21)

(1-22)

(1-23)

(1-24)

(1-25)

(1-26)

(1-27)

(1-28)

(1-29)

(1-30)

(1-31)

(1-32)

(1-33)

(1-34)

(1-35)

(1-36)

(1-37)

(1-38)

(1-39)

(1-40)

(1-41)

(1-42)

(1-43)

(1-44)

(1 − 4 5)

(1 − 4 6)

(1 − 4 7)

(2-1) (2a)

(2-2) (2a)

(2-3) (2a)

(2-4) (2a)

(2-5) (2a)

(2-6)　(2b)

(2-7)　(2c)

(2-8)　(2c)

(2-9)　(2a)

(2-10)　(2a)

(3-1)

(3-2)

(3-3)

(3-4)

(3-5)

(3-6)

(3-7)

(3-8)

(3-9)

(3-10)

(3-17)

(3-18)

(3-19)

(3-20)

(3-21)

(3-22)

(3-23)

(4a-1)

(4a-2)

(4a-3)

(4a-4)

(4a-5)

(4a-6)

(4a-7)

(4a-8)

(4a-9)

(4a-10)

(4a-11)

(4a-12)

(4a-13)

(4a-14)

(4a-15)

(4a-16)

(4a-17)

(4a-18)

(4a-19)

(4a-20)

(4b-1)

(4b-2)

(4b-3)

(4b-4)

(4b-5)

(4b-6)

(4b-7)

(4b-8)

(4b-9)

(4b-10)

(4b-11)

(4b-12)

(4b-13)

(4b-14)

(4b-15)

(4b-16)

(4c-1)

(4c-2)

(4c-3)

(4c-4)

(4c-5)

(4c-6)

(4c-7)

(4c-8)

(4c-9)

(4c-10)

(4c-11)

(4c-12)

(4c-13)

(4c-14)

(4c-15)

(4c-16)

(4c-17)

(4c-18)

(4c-19)

(4c-20)

(4c-21)

(4c-22)

(4c-23)

(4c-24)

(4c-25)

(4c-26)

(4c-27)

(4c-28)

(4c-29)

(4c-30)

(5-1)

(5-2)

(5-3)

(5-4)

(5-5)

(5-6)

(5-7)

(5-8)

(5-9)

(5-10)

(5-11)

(5-12)

(5-13)

(5-14)

(5-15)

(5-16)

(5-17)

(5-18)

(5-19)

(5-20)

(5-21)

(5-22)

(5-23)

(5'-1)

(5'-2)

(6-1)

(6-2)

(6-3)

(6-4)

(6-5)

(6-11)

(6-12)

(6-13)

(6-14)

(6-15)

(6 − 1 6)

(6 − 1 7)

ORGANIC ELECTROLUMINESCENT DEVICE

TECHNICAL FIELD

This invention relates to an organic electroluminescent device (organic EL device) which is a self-light emitting device suitable for various types of display devices. More specifically, the invention relates to an organic EL device which includes, in the hole transport layer, an indenoacridan derivative having a specific molecular structure.

BACKGROUND ART

Organic EL devices, being self-light emitting devices, are brighter and more visible than liquid crystal devices, enabling a clear display. Accordingly, much research has been conducted on organic EL devices.

In 1987, C. W. Tang et al. of Eastman Kodak Company successfully developed a practical organic EL device by creating a layered structure that divides various roles for light emission among different materials. This organic EL device is configured by laminating a layer of a fluorescent body capable of transporting electrons and a layer of an organic substance capable of transporting holes. By injecting positive charges and negative charges into a layer of the fluorescent body and causing light to be emitted, a high luminance of 1,000 cd/m$^2$ or more at a voltage of not more than 10 V can be obtained.

Many improvements for the practical utilization of organic EL devices have been made to date. For example, it is commonly known that a high efficiency and durability can be achieved by dividing up even further the various roles of the layered structure and creating a layered structure that has, provided on a substrate, an anode, a hole injection layer, a hole transport layer, a luminous layer, an electron transport layer, an electron injection layer and a cathode.

To further improve the luminous efficiency, efforts are being made to utilize triplet excitons and the use of phosphorescent light-emitting compounds is being investigated.

In addition, devices that utilize light emission by thermally activated delayed fluorescence (TADF) have also been developed. For example, in 2011, Adachi et al. at Kyushu University achieved an external quantum efficiency of 5.3% with a device that uses a thermally activated delayed fluorescent material.

The luminous layer is fabricated by doping a charge transporting compound that is generally called the host material with a fluorescent compound or phosphorescent light-emitting compound or with a material radiating delayed fluorescence. Selection of the organic materials in an organic EL device has a large influence on device characteristics such as efficiency and durability.

In an organic EL device, the charges injected from both electrodes recombine in the luminous layer, resulting in light emission. How efficiently the hole and electron charges are delivered to the luminous layer is important, and the device to have an excellent carrier balance is required. Also, increasing the hole-injecting properties and increasing the electron-blocking properties that block electrons injected from the cathode improves the probability of holes and electrons recombining, and confining excitons generated within the luminous layer enables a high luminous efficiency to be obtained. Because of the important role thus played by the hole-transporting material, there exists a desire for a hole-transporting material which has high hole-injecting properties, a high hole mobility, high electron-blocking properties and moreover a high durability to electrons.

With respect to the device life, the heat resistance and amorphousness of the material are also important. In a material having a low heat resistance, thermal decomposition arises even at low temperatures due to the heat generated during device operation, resulting in degradation of the material. In a material having low amorphousness, crystallization of the thin film occurs in a short time, leading to device deterioration. Hence, the material to be used is required to have high heat resistance and good amorphousness.

N,N'-diphenyl-N,N'-di(α-naphthyl)benzidine (NPD) and various aromatic amine derivatives are known as hole-transporting materials that have hitherto been used in organic EL devices (see, for example, PTL 1 and PTL 2). Although NPD has a good hole-transporting ability, the glass transition temperature (Tg), which serves as an indicator of heat resistance, is low at 96° C. Hence, under high-temperature conditions, the device characteristics deteriorate due to crystallization.

Among the aromatic amine derivatives mentioned in PTL 1 and PTL 2 are also compounds having an excellent hole mobility of at least $10^{-3}$ cm$^2$/Vs, but because the electron-blocking properties are inadequate, some electrons end up passing through the luminous layer, making it unlikely that, for example, an enhanced luminous efficiency is achieved. To further increase efficiency, there has existed a desire for a material which has higher electron-blocking properties and forms a thin film that is more stable and has a higher heat resistance.

Aromatic amine derivatives with high durability have also been reported (see, for example, PTL 3). However, these have been used as charge-transporting materials for electrophotographic photoreceptors, there are no examples of their use in organic EL devices.

Arylamine compounds having a substituted carbazole structure have been proposed as compounds having improved characteristics such as heat resistance and hole-injecting properties (see, for example, PTL 4 to PTL 6). However, in devices which use these compounds in the hole injection layer or hole transport layer, although the heat resistance and luminous efficiency have been improved, the results are still insufficient. An even lower driving voltage and an even higher luminous efficiency are desired.

In order to improve the device characteristics of organic EL devices and enhance the yield in device fabrication, there exists a desire for a device which, by combining materials that have excellent hole and electron injecting and transporting performances and form thin films of excellent stability and durability, enables holes and electrons to recombine at a high efficiency and has a high luminous efficiency, a low driving voltage and a long life.

In addition, to improve the device characteristics of organic EL devices, there exists a desire for a device which, by combining materials that have excellent hole and electron injecting and transporting performances and form thin films of excellent stability and durability, are balanced in careers and achieves a high efficiency, a low driving voltage and a long life.

CITATION LIST

Patent Literature

[PTL 1] Japanese Patent Application Laid-open No. H8-048656
[PTL 2] Japanese Patent No. 3194657
[PTL 3] Japanese Patent No. 4943840
[PTL 4] WO 2006/033563
[PTL 5] WO 2007/110228
[PTL 6] WO 2010/147319

SUMMARY OF THE INVENTION

Technical Problem

The object of the invention is to provide an organic EL device including a hole transport layer which is formed of a hole-transporting material having an excellent hole-injecting and transporting performance, an excellent electron-blocking ability, excellent stability in a thin-film state and durability and which is combined with other layers so as to effectively show the excellent properties of the hole-transporting material, thereby achieving in the device a high efficiency, a low driving voltage and a long life.

Solution to Problem

The inventors have discovered that indenoacridan derivatives having a specific molecular structure exhibit excellent properties as a hole-transporting material and that, by using such compounds to form a hole transport layer, when the luminous layer includes an N-aromatic substituted indenoindole compound or an N-aromatic substituted carbazole compound, there can be obtained an organic EL device that achieves an excellent carrier balance and has excellent characteristics. As a result, the inventors have accomplished the present invention.

Accordingly, the invention provides an organic electroluminescent device having, in order, an anode, a hole transport layer, a luminous layer, an electron transport layer and a cathode, wherein the hole transport layer contains an indenoacridan derivative represented by the following general formula (1), and the luminous layer includes an N-aromatic substituted indenoindole compound and/or an N-aromatic substituted carbazole compound.

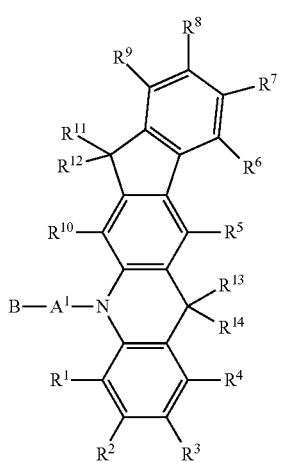

(1)

In the formula (1),
$A^1$ is a divalent aromatic hydrocarbon group, a divalent aromatic heterocyclic group or a single bond,
B is a monovalent aromatic hydrocarbon group; a monovalent aromatic heterocyclic group; or a disubstituted amino group having, as a substituent, a vinyl group which may have a substituent, a monovalent aromatic hydrocarbon group or a monovalent aromatic heterocyclic group,
when B is a disubstituted amino group, $A^1$ is not a single bond, and when $A^1$ is not a single bond, $A^1$ and B may be bonded to each other via a single bond, a methylene group which may have a substituent, an oxygen atom or a sulfur atom to form a ring,
$R^1$ to $R^{10}$ each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, an aralkyl group or an aryloxy group, and may be bonded to each other via a methylene group which may have a substituent, an oxygen atom or a sulfur atom to form a ring and
$R^{11}$ to $R^{14}$ each represent an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, an aralkyl group or an aryloxy group, and $R^{11}$ and $R^{12}$, or $R^{13}$ and $R^{14}$, may be bonded to each other via a single bond, a methylene group which may have a substituent, an oxygen atom or a sulfur atom to form a ring.

In the organic EL device of the invention, the N-aromatic substituted indenoindole compound used in the luminous layer is preferably a compound represented by the following general formula (2).

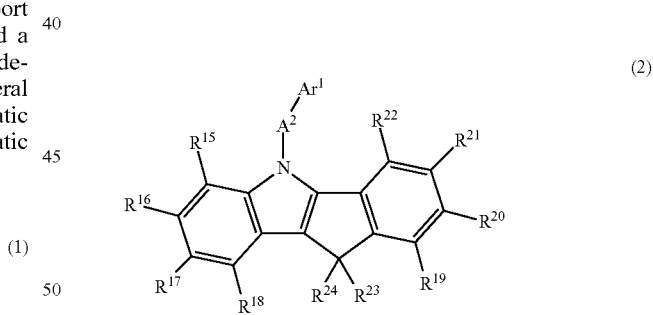

(2)

In the formula (2),
$A^2$ is a divalent aromatic hydrocarbon group, a divalent aromatic heterocyclic group or a single bond,
$Ar^1$ is a monovalent aromatic hydrocarbon group or a monovalent aromatic heterocyclic group,
$R^{15}$ to $R^{22}$ each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, an aralkyl group, an aryloxy group, or a disubstituted amino group having, as a substituent, a monovalent aromatic hydrocarbon group or a monovalent aromatic heterocyclic group, may be bonded to each other via a single bond, a methylene group which may have a substituent, an oxygen atom or a sulfur atom to form a ring, and some of $R^{15}$ to $R^{18}$ or some of $R^{19}$ to $R^{22}$ may be detached and the remaining groups of $R^{15}$ to $R^{18}$ or the remaining groups of $R^{19}$ to $R^{22}$ may be bonded to vacancies generated by the detachment via a methylene group which may have a substituent, an oxygen atom, a sulfur atom or a monoarylamino group to form a ring and $R^{23}$ and $R^{24}$ each represent an alkyl group having 1 to 6 carbon atoms, a monovalent aromatic hydrocarbon group, a monovalent aromatic heterocyclic group or an aralkyl group, and may be bonded to each other via a single bond, a methylene group which may have a substituent, an oxygen atom or a sulfur atom to form a ring.

Also, in the organic EL device of the invention, the N-aromatic substituted carbazole compound used in the luminous layer is preferably a compound represented by the following general formula (3).

(3)

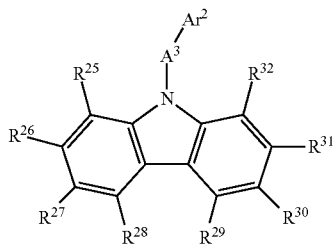

In the formula (3), $A^3$ is a divalent aromatic hydrocarbon group, a divalent aromatic heterocyclic group or a single bond, $Ar^2$ is a monovalent aromatic hydrocarbon group or a monovalent aromatic heterocyclic group and $R^{25}$ to $R^{32}$ each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, an aralkyl group, an aryloxy group, or a disubstituted amino group having, as a substituent, a monovalent aromatic hydrocarbon group or a monovalent aromatic heterocyclic group, may be bonded to each other via a single bond, a methylene group which may have a substituent, an oxygen atom or a sulfur atom to form a ring, and some of $R^{25}$ to $R^{28}$ or some of $R^{29}$ to $R^{32}$ may be detached and the remaining groups of $R^{25}$ to $R^{28}$ or the remaining groups of $R^{29}$ to $R^{32}$ may be bonded to vacancies generated by the detachment via a methylene group which may have a substituent, an oxygen atom, a sulfur atom or a monoarylamino group to form a ring.

Also, in the organic EL device of the invention, the electron transport layer preferably includes an anthracene derivative represented by the following general formula (4).

(4)

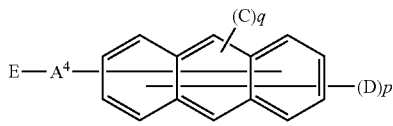

In the formula (4), $A^4$ is a divalent aromatic hydrocarbon group, a divalent aromatic heterocyclic group or a single bond, E is a monovalent aromatic heterocyclic group, C is a monovalent aromatic hydrocarbon group or a monovalent aromatic heterocyclic group, D is a hydrogen atom, a deuterium atom, a fluorine atom, a chlorine atom, a cyano group or an alkyl group having 1 to 6 carbon atoms and p is an integer of 7 or 8 and q is an integer of 1 or 2, with the proviso that the sum of p and q is 9.

It is especially preferable for the anthracene derivative to be a compound represented by the following general formula (4a), (4b) or (4c).

Anthracene derivatives represented by the general formula (4a);

(4a)

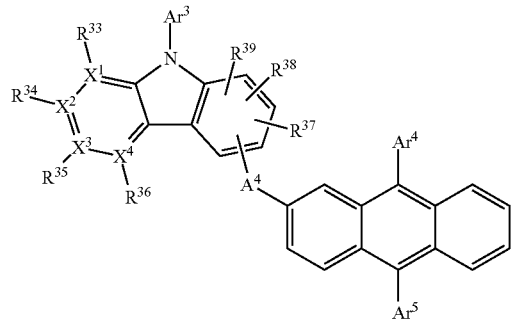

where $A^4$ is as defined in the formula (4), $Ar^3$, $Ar^4$ and $Ar^5$ each represent a monovalent aromatic hydrocarbon group or a monovalent aromatic heterocyclic group, $R^{33}$ to $R^{39}$ each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic, group, an aralkyl group or an aryloxy groups, and may be bonded to each other via a single bond, a methylene group which may have a substituent, an oxygen atom or a sulfur atom to form a ring and $X^1$, $X^2$, $X^3$ and $X^4$ each represent a carbon atom or a nitrogen atom, provided that only one of these is a nitrogen atom, with none of $R^{33}$ to $R^{36}$, including hydrogen atoms, being bonded to the nitrogen atom.

Anthracene derivatives represented by the general formula (4b);

(4b)

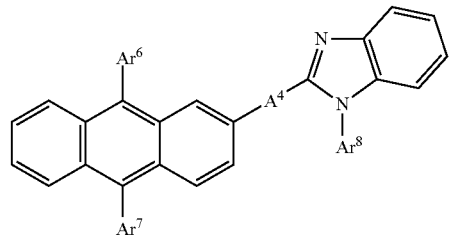

where

A⁴ is as defined in the formula (4) and

Ar⁶, Ar⁷ and Ar⁸ each represent a monovalent aromatic hydrocarbon group or a monovalent aromatic heterocyclic group.

Anthracene derivatives represented by the general formula (4c);

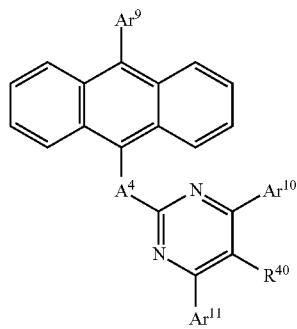

(4c)

where

A⁴ is as defined in the formula (4),

Ar⁹, Ar¹⁰ and Ar¹¹ each represent a monovalent aromatic hydrocarbon group or a monovalent aromatic heterocyclic group and R⁴⁰ is a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, an aralkyl group or an aryloxy group.

In addition, in the organic EL device of the invention, it is more preferable for, (1) the hole transport layer to have a two-layer structure including a first hole transport layer and a second hole transport layer, with the second hole transport layer being positioned on the luminous layer side and including the indenoacridan derivative represented by the general formula (1),
(2) the luminous layer to further include a phosphorescence emitting material,
(3) the phosphorescence emitting material to be a metal complex containing iridium or platinum and
(4) the phosphorescence emitting material to be a red-emitting dopant.

Advantageous Effects of Invention

In the organic EL device of the invention, the indenoacridan derivative represented by the general formula (1) which is included in the hole transport layer has an indenoacridan ring on the molecule and is characterized in that a monovalent aromatic hydrocarbon group, a monovalent aromatic heterocyclic group or a specific disubstituted amino group is bonded to the nitrogen atom on the ring via a single bond or a divalent aromatic group. Indenoacridan derivatives with such a structure have the following properties, (1) good hole injecting and transporting properties,
(2) excellent electron-blocking ability,
(3) stable thin-film state, and
(4) excellent heat resistance.

Moreover, the organic EL device of the invention, in addition to including such an indenoacridan derivative in the hole transport layer, also includes an N-aromatic substituted indenoindole compound or an N-aromatic substituted carbazole compound in the luminous layer. As a result, the excellent properties of the indenoacridan derivative are fully shown, holes can be efficiently injected and transported in the luminous layer, and light emission at a high efficiency and low driving voltage can be achieved. Additionally, the life of the device can be increased.

In this invention, by also providing, together with the above hole transport layer and the above luminous layer, an electron transport layer formed of an anthracene derivative represented by the above-mentioned general formula (4), holes and electrons can be more efficiently injected and transported to the luminous layer, making it possible to ensure a high carrier balance and achieve even further improvement in the device characteristics.

Furthermore, in this invention, by giving the hole transport layer a two-layer structure including a first hole transport layer and a second hole transport layer, and by forming the second hole transport layer, which is positioned on the side adjacent to the luminous layer and is formed of an indenoacridan derivative of the above general formula (1), the electron-blocking ability of the indenoacridan derivative is optimized, resulting in higher efficiency and longer life (higher durability) of the organic EL device.

DESCRIPTION OF EMBODIMENTS

Figure 1:
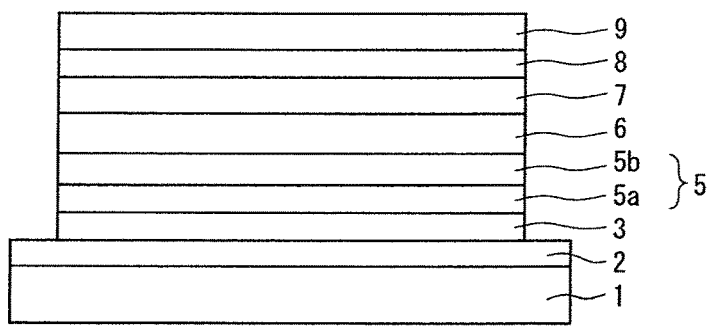
FIG. 1 is a diagram showing a preferred layer construction used in the examples of the organic EL device of the invention.

The organic EL device of the invention has a basic structure in which an anode, a hole transport layer, a luminous layer, an electron transport layer and a cathode have been formed in this order on a transparent substrate such as a glass substrate or a transparent plastic substrate (e.g., a polyethylene terephthalate substrate). As long as the device has this basic structure, the layer structure may take various forms. For example, the hole transport layer may have a two-layer structure including a first hole transport layer positioned on the anode side and a second hole transport layer adjacent to the luminous layer, a hole injection layer may be provided between the anode and the hole transport layer, and an electron injection layer may be provided between the electron transport layer and the cathode. In FIG. 1, for example, which shows the layer structure used in the examples described below, an anode 2, a hole injection layer 3, a hole transport layer 5, a luminous layer 6, an electron transport layer 7, an electron injection layer 8 and a cathode 9 are formed in this order on a transparent substrate 1. In this example, the hole transport layer 5 has a two-layer structure including a first hole transport layer 5a and a second hole transport layer 5b. The layers making up the organic EL device of the invention are each described below.

<Anode 2>

The anode 2 is formed on the transparent substrate 1 by the vapor deposition of an electrode material having a large work function, such as ITO or gold.

<Hole Injection Layer 3>

When necessary, a hole injection layer 3 is suitably formed between the anode 2 and the hole transport layer 5. This hole injection layer 3 may be formed using a publicly known material, examples of which include materials such as starburst-shaped triphenylamine derivatives and various triphenylamine tetramers; porphyrin compounds exemplified by copper phthalocyanine; acceptor-type heterocyclic compounds such as hexacyanoazatriphenylene, and coatable polymeric materials. Use can also be made of tris(bromophenyl)aminium hexachloroantimonate, radialene derivatives (see, for example, WO 2014/009310), etc. that are P-doped, as well as polymeric compounds having, as a partial structure therein, a TPD or other benzidine derivative structure.

<Hole Transport Layer 5>

The hole transport layer 5 is provided between the above anode 2 and the luminous layer 6. In the invention, this hole transport layer includes an indenoacridan derivative represented by the following general formula (1).

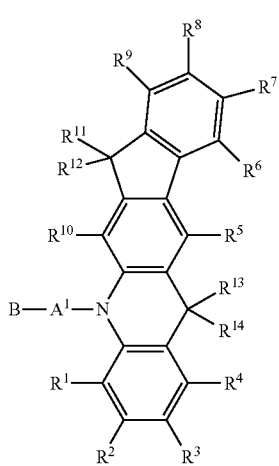

(1)

In the general formula (1), $A^1$ is a divalent aromatic hydrocarbon group, a divalent aromatic heterocyclic group or a single bond.

Here, the divalent aromatic hydrocarbon group is formed of an aromatic hydrocarbon ring having two sites available for bonding. Examples of such aromatic hydrocarbon rings include benzene, biphenyl, terphenyl, tetrakisphenyl, styrene, naphthalene, anthracene, acenaphthylene, fluorene, phenanthrene, indane, pyrene, triphenylene and fluoranthene.

The divalent aromatic heterocyclic group is formed of an aromatic heterocycle having two sites available for bonding. Examples of such aromatic heterocycles include pyridine, pyrimidine, triazine, pyrrole, furan, thiophene, quinoline, isoquinoline, benzofuran, benzothiophene, indoline, carbazole, carboline, benzoxazole, benzothiazole, quinoxaline, benzoimidazole, pyrazole, dibenzofuran, dibenzothiophene, naphthyridine, phenanthroline, acridine, quinazoline and benzoquinazoline.

B in the general formula (1) represents a monovalent aromatic hydrocarbon group, a monovalent aromatic heterocyclic group or a disubstituted amino group.

The monovalent aromatic hydrocarbon group is formed of an aromatic hydrocarbon ring having one site available for bonding, and the monovalent aromatic heterocyclic group is formed of an aromatic heterocycle having one site available for bonding. Examples of these are given below.

Monovalent Aromatic Hydrocarbon Groups;

phenyl, biphenylyl, terphenylyl, naphthyl, anthracenyl, phenanthrenyl, fluorenyl, indenyl, pyrenyl, perylenyl, fluoranthenyl and triphenylenyl groups.

Monovalent Aromatic Heterocyclic Groups;

pyridyl, pyrimidinyl, triazinyl, furyl, pyrrolyl, thienyl, quinolyl, isoquinolyl, benzofuranyl, benzothienyl, indolyl, carbazolyl, quinazolinyl, benzoxazolyl, benzothiazolyl, quinoxalinyl, benzoimidazolyl, benzoquinazolinyl, pyridopyrimidinyl, pyrazolyl, naphthopyrimidinyl, dibenzofuranyl, dibenzothienyl, naphthyridinyl, phenanthrolinyl, acridinyl and carbolinyl groups.

The substituents in the disubstituted amino group are vinyl groups (which may have a substituent), monovalent aromatic hydrocarbon groups or monovalent aromatic heterocyclic groups. These monovalent aromatic hydrocarbon groups and monovalent aromatic heterocyclic groups are exemplified by the same groups as mentioned above.

In $A^1$ and B, when B is a disubstituted amino group, $A^1$ is not a single bond. When $A^1$ is not a single bond, i.e., when $A^1$ is a divalent aromatic hydrocarbon group or a divalent aromatic heterocyclic group, $A^1$ and B may be bonded to each other via a single bond, a methylene group which may have a substituent, an oxygen atom or a sulfur atom to form a ring.

In particular, when the disubstituted amino group represented by B has a vinyl group, this vinyl group preferably bonds via a single bond to the aromatic ring on $A^1$ or to the aromatic ring on the other substituent of the disubstituted amino group to additionally form an aromatic ring (see subsequently described Compound Nos. 1-22, 1-23 and 1-42).

That is, it is desirable for the indenoacridan derivative represented by the above general formula (1) to be an N-aromatic substitution product in which an aromatic hydrocarbon ring or an aromatic heterocycle is bonded to the nitrogen atom on the acridan ring.

The above-described groups represented by $A^1$ and B, such as monovalent or divalent aromatic hydrocarbon groups or aromatic heterocyclic groups, and disubstituted amino groups, may additionally have substituents.

Such substituents (including substituents that may be on the vinyl group of the disubstituted amino group) are exemplified by a deuterium atom, a cyano group and a nitro group, and also by the following groups.

halogen atoms such as fluorine, chlorine, bromine and iodine atoms;

alkyl groups having 1 to 6 carbon atoms, such as methyl, ethyl, n-propyl, isopropyl, n-butyl, isobutyl, tert-butyl, n-pentyl, isopentyl, neopentyl and n-hexyl groups;

alkyloxy groups having 1 to 6 carbon atoms, such as methyloxy, ethyloxy and propyloxy groups;

alkenyl groups such as vinyl and allyl groups;

aryl groups such as phenyl, biphenylyl, terphenylyl, naphthyl, anthracenyl, phenanthrenyl, fluorenyl, indenyl, pyrenyl, perylenyl, fluoranthenyl and triphenylenyl groups;

aryloxy groups such as phenyloxy and tolyloxy groups;
aralkyl groups such as benzyl and phenethyl groups;
arylalkyloxy groups such as benzyloxy and phenethyloxy groups;
aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, quinazolinyl, benzoxazolyl, benzothiazolyl, quinoxalinyl, benzoimidazolyl, benzoquinazolinyl, pyrazolyl, dibenzofuranyl, dibenzothienyl and carbolinyl groups;
arylvinyl groups such as styryl and naphthylvinyl groups;
acyl groups such as acetyl and benzoyl groups; and
silyl groups such as trimethylsilyl and triphenylsilyl groups;

These substituents may additionally have thereon any of the substituents mentioned here.

Moreover, the substituents mentioned above may be bonded to each other via a single bond, a substituted or unsubstituted methylene group, an oxygen atom or a sulfur atom to forma ring.

In the above general formula (1), $R^1$ to $R^{10}$ each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, an aralkyl group or an aryloxy group.

Examples of alkyl groups having 1 to 6 carbon atoms include methyl, ethyl, n-propyl, isopropyl, n-butyl, isobutyl, tert-butyl, n-pentyl, isopentyl, neopentyl and n-hexyl groups.

Examples of cycloalkyl groups having 5 to 10 carbon atoms include cyclopentyl, cyclohexyl, 1-adamantyl and 2-adamantyl groups.

Examples of alkenyl groups having 2 to 6 carbon atoms include vinyl, allyl, isopropenyl and 2-butenyl groups.

Examples of alkyloxy groups having 1 to 6 carbon atoms include methyloxy, ethyloxy and propyloxy groups.

Examples of cycloalkyloxy groups having 5 to 10 carbon atoms include cyclopentyloxy, cyclohexyloxy, 1-adamantyloxy and 2-adamantyloxy groups.

The monovalent aromatic hydrocarbon groups and monovalent aromatic heterocyclic groups are exemplified by the same ones as those exemplified for "B" above.

Examples of aralkyl groups include benzyl and phenethyl groups.

Examples of aryloxy groups include phenyloxy, tolyloxy, biphenyloxy, naphthyloxy, anthracenyloxy, phenanthrenyloxy, fluorenyloxy, indenyloxy, pyrenyloxy and perylenyloxy groups.

The above groups may be bonded to each other via a methylene group which may have a substituent, an oxygen atom or a sulfur atom to form a ring.

The above groups represented by $R^1$ to $R^{10}$ may have substituents. Such substituents are exemplified by, within a range that satisfies the conditions regarding the number of carbons, the same ones exemplified as the substituents possessed by the monovalent aromatic hydrocarbon groups and monovalent aromatic heterocyclic groups in "B" above.

These substituents may be present independently or may be bonded to each other via a single bond, a methylene group which may have a substituent, an oxygen atom or a sulfur atom to form a ring.

$R^{11}$ to $R^{14}$ in the general formula (1) represent an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, an aralkyl group or an aryloxy group.

Examples of these groups include the same groups mentioned above as examples for $R^1$ to $R^{10}$. These groups, as with the substituents on $R^1$ to $R^{10}$, may additionally have substituents.

In addition, $R^{11}$ and $R^{12}$, or $R^{13}$ and $R^{14}$, may be bonded to each other via a single bond, a methylene group which may have a substituent, an oxygen atom or a sulfur atom to form a ring.

Examples of indenoacridan derivatives of the above general formula (1) include Compounds (1-1) to (1-47) shown in FIGS. 10 to 19.

In this invention, as will be understood from the subsequently described examples, indenoacridan derivatives of the above general formula (1) have a high glass transition temperature Tg (e.g., 110° C. or above). Therefore, the thin-film state is stable and the heat resistance is excellent. Also, compared with the work functions of ordinary hole-transporting materials (approx. 5.4 eV), these indenoacridan derivatives have a high work function. Therefore, they have excellent hole-transporting properties, high hole mobility and good hole-injecting properties. In addition, they also have excellent electron-blocking properties.

Such indenoacridan derivatives may be used individually, two or more may be used in admixture, or, within a range that does not detract from the outstanding properties of the indenoacridan derivative, they may be used together with a known hole-transporting material to form the hole transport layer 5.

Examples of such known hole-transporting materials include benzidine derivatives such as N,N'-diphenyl-N,N'-di(m-tolyl)benzidine (TPD), N,N'-diphenyl-N,N'-di(a-naphthyl)benzidine (NPD) and N,N,N',N'-tetrabiphenylylbendizine; 1,1-bis[4-(di-4-tolylamino)phenyl]cyclohexane (TAPC); the subsequently described triarylamine derivatives of a general formula (5) or a general formula (6); and also various triphenylamine trimers.

In this hole transport layer 5, it is also possible to use a material P-doped with, for instance, tris(bromophenyl)aminium hexachloroantimony, radialene derivatives (see, for example, WO 2014/009310), etc. as well as polymeric compounds having the structure of a benzidine derivative such as TPD in a molecule.

The above-described hole transport layer 5 is preferably formed by vapor deposition or co-vapor deposition of a gas containing an indenoacridan derivative of the general formula (1), although formation may also be carried out by a known method such as spin coating or ink-jet printing.

The thickness of such a hole transport layer 5 is generally about 25 to 60 nm. However, light emission can be obtained at low driving voltage even when the thickness is increased to, for example, 100 nm or more, and consequently a rise in the driving voltage can be suppressed. That is, owing to the high degree of freedom in the thickness of the hole transport layer, a practical driving voltage can be maintained at a thickness of, for example, 20 to 300 nm, especially 20 to 200 nm.

In this invention, as shown in FIG. 1, for example, the hole transport layer 5 which includes the above indenoacridan derivative preferably has a two-layer structure including a first hole transport layer 5a positioned on the anode side and a second hole transport layer 5b positioned on the luminous layer 6 side.

A hole transport layer 5 having such a two-layer structure is described later in the Specification.

<Luminous Layer 6>

The luminous layer 6 may be formed by a known method such as vapor deposition, spin coating or ink-jet printing, according to the type of material used. In this invention, it is important for the luminous layer 6 to include in particular an N-aromatic substituted indenoindole compound or an N-aromatic substituted carbazole compound. That is, by using these compounds together with an emitting material in the luminous layer 6, full advantage is taken of the hole transporting and injecting properties of the indenoacridan derivative included in the above-described hole transport layer 5, and holes are efficiently injected into the luminous layer 6, and thus achieve light emission at a high efficiency and low driving voltage.

The N-aromatic substituted indenoindole compound is a compound having an indenoindole ring structure, an aromatic group has been introduced onto the nitrogen atom within the ring. This compound is represented by, for example, the general formula (2) below.

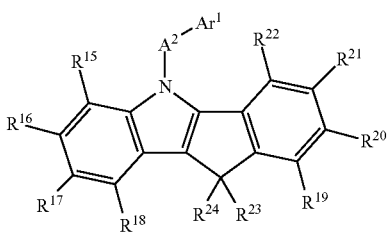

(2)

In the general formula (2), $A^2$ bonded to the nitrogen atom represents, as with $A^1$ in the general formula (1), a divalent aromatic hydrocarbon group, a divalent aromatic heterocyclic group or a single bond.

This divalent aromatic hydrocarbon group and divalent aromatic heterocyclic group are exemplified by the same groups exemplified for $A^1$ in the general formula (1). These groups may have the same substituents exemplified for $A^1$ in the general formula (1). Such substituents may be bonded to each other via a single bond, a substituted or unsubstituted methylene group, an oxygen atom or a sulfur atom to form a ring.

Also, $Ar^1$ represents a monovalent aromatic hydrocarbon group or a monovalent aromatic heterocyclic group. These monovalent aromatic hydrocarbon groups and monovalent aromatic heterocyclic groups are exemplified by the same groups exemplified for B in the general formula (1). These groups may have the same substituents exemplified for B, and such substituents may be bonded to each other via a single bond, a substituted or unsubstituted methylene group, an oxygen atom or a sulfur atom to form a ring.

$R^{15}$ to $R^{22}$ in the general formula (2) represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, an aralkyl group, an aryloxy group, or a disubstituted amino group having, as a substituent, a monovalent aromatic hydrocarbon group or a monovalent aromatic heterocyclic group.

Specific examples of the monovalent aromatic hydrocarbon group, the monovalent aromatic heterocyclic group and other groups included as substituents on the disubstituted amino group include the groups mentioned as examples of B or $R^1$ to $R^{10}$ in the general formula (1). These groups too may be bonded to each other via a single bond, a methylene group which may have a substituent, an oxygen atom or a sulfur atom to form a ring (i.e., a condensed ring) (see, for example, subsequently described general formulas (2d) and (2e)).

In addition, some of $R^{15}$ to $R^{18}$ or some of $R^{19}$ to $R^{22}$ may be detached and the remaining groups of $R^{15}$ to $R^{18}$ or the remaining groups of $R^{19}$ to $R^{22}$ (these remaining groups being the groups mentioned above) may be bonded to vacancies generated by the detachment via a methylene group which may have a substituent, an oxygen atom, a sulfur atom or a monoarylamino group to form a ring (i.e., a condensed ring) (see, for example, subsequently described general formulas (2a) to (2c)).

$R^{23}$ and $R^{24}$ in the general formula (2) represent an alkyl group having 1 to 6 carbon atoms, a monovalent aromatic hydrocarbon group or a monovalent aromatic heterocyclic group. Specific examples of these groups include those mentioned as examples of B or $R^1$ to $R^{10}$ in the general formula (1). These groups may be bonded to each other via a single bond, a methylene group which may have a substituent, an oxygen atom or a sulfur atom to form a ring.

In the N-aromatic substituted indenoindole compound represented by the above-described general formula (2), it is preferable for a ring to be formed by $R^{15}$ to $R^{18}$, or by $R^{19}$ to $R^{22}$.

For example, N-aromatic substituted indenoindole compounds represented by the following general formulas (2a) to (2e) are examples in which $R^{15}$ to $R^{18}$ form a ring.

In the following general formulas (2a) to (2e), $A^2$, $Ar^1$ and $R^{15}$ to $R^{24}$ have the meanings indicated in the above general formula (2). X is a divalent linking group, and is a methylene group which may have a substituent, an oxygen atom, a sulfur atom or a monoarylamino group.

General Formula (2a);

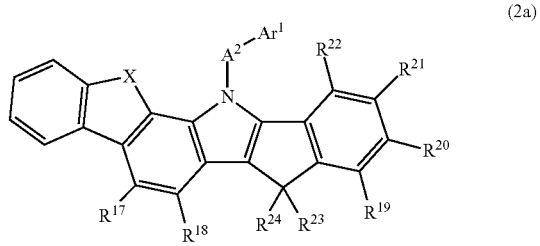

(2a)

The general formula (2a) has a structure in which, at the position in the benzene ring which is a vacant site since $R^{15}$ in the general formula (2) detaches, the $R^{16}$ group adjacent to $R^{15}$ bonds through the linking group X to form a condensed ring.

General Formula (2b);

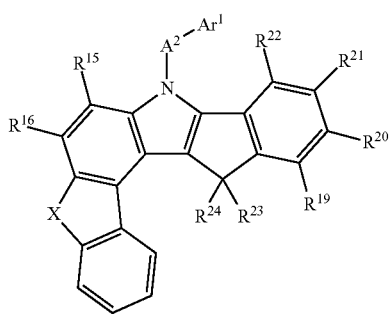

(2b)

The general formula (2b) has a structure in which, at the position in the benzene ring which is a vacant site since $R^{17}$ in the general formula (2) detches, the $R^{18}$ group adjacent to $R^{17}$ bonds through the linking group X to forma condensed ring.

General Formula (2c);

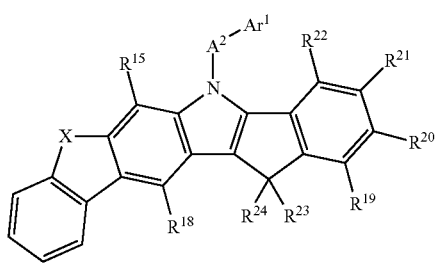

(2c)

The general formula (2c) has a structure in which, at the position in the benzene ring which is a vacant site since $R^{16}$ in the general formula (2) detaches, the $R^{17}$ group adjacent to $R^{16}$ bonds through the linking group X to form a condensed ring.

In the above general formulas (2a) to (2c), examples of condensed rings that form due to bonding to a benzene ring through a linking group X include a fluorene ring (X=methylene), a carbazole ring (X=a monophenylamino group), a dibenzofuran ring (X=oxygen atom) and a dibenzothiophene ring (X=sulfur atom).

General Formula (2d);

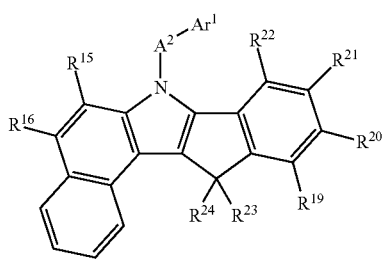

(2d)

The general formula (2d) has a structure in which $R^{17}$ (vinyl group) and $R^{18}$ (vinyl group) in the general formula (2) bond to form a benzene ring.

General Formula (2e);

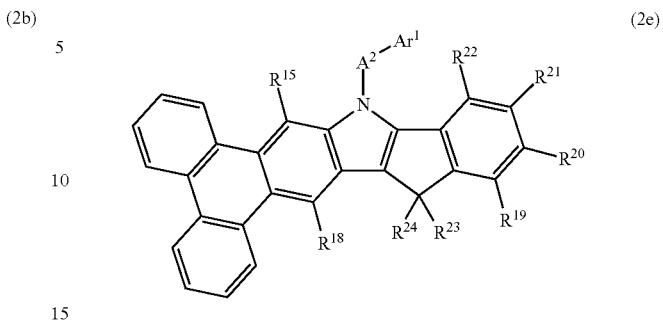

(2e)

The general formula (2e) has a structure in which $R^{16}$ (phenyl group) and $R^{17}$ (phenyl group) in the general formula (2) bond to form a phenanthrene ring.

The above general formulas (2a) to (2e) show structures in which $R^{15}$ to $R^{18}$ form a ring. In structures where $R^{19}$ to $R^{22}$ form a ring, the ring formed in these general formulas (2a) to (2e) condense to the benzene ring to which $R^{19}$ to $R^{22}$ are bonded.

Figure 20:
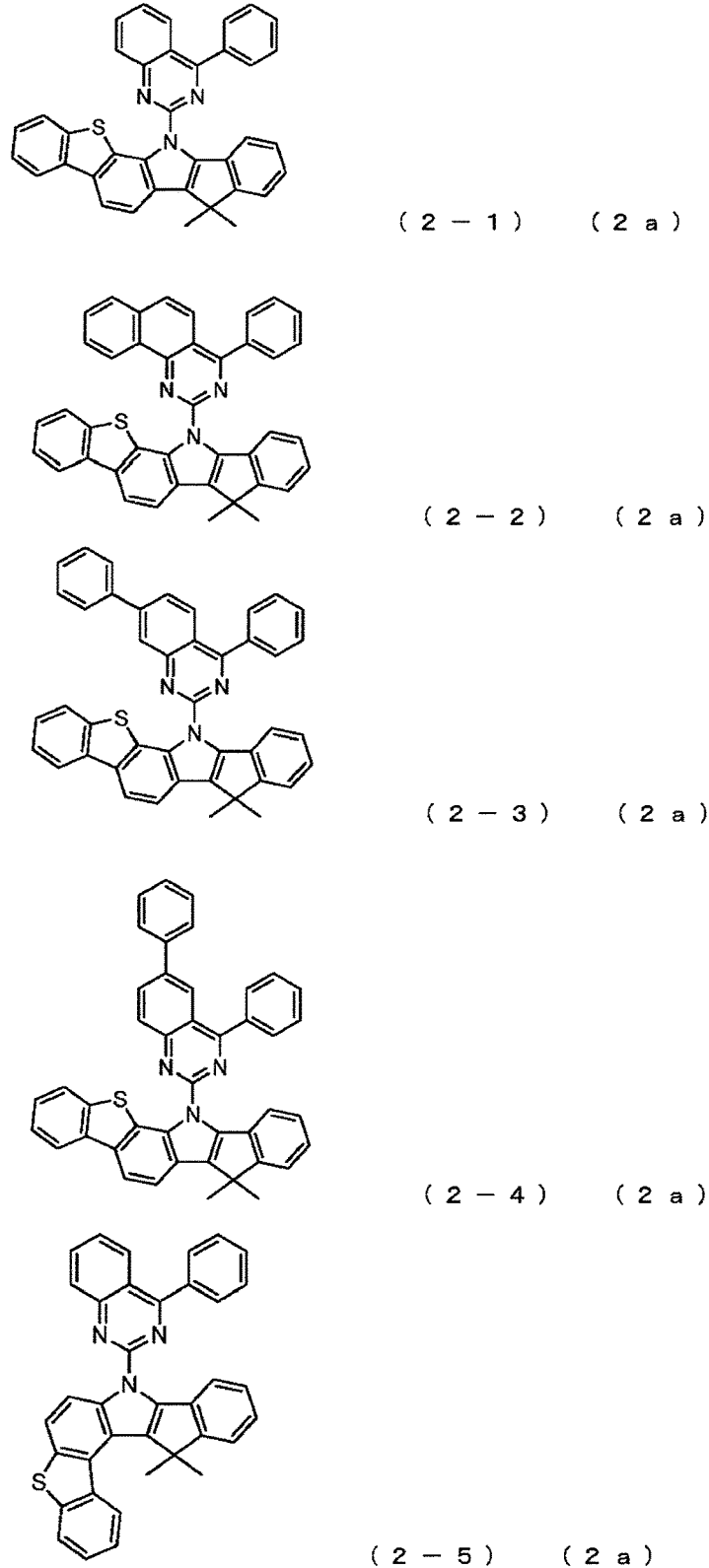
FIG. 20 is a diagram showing the structural formulas of Compound Nos. (2-1) to (2-5) that are N-aromatic substituted indenoindole derivatives of general formula (2).
Figure 21:
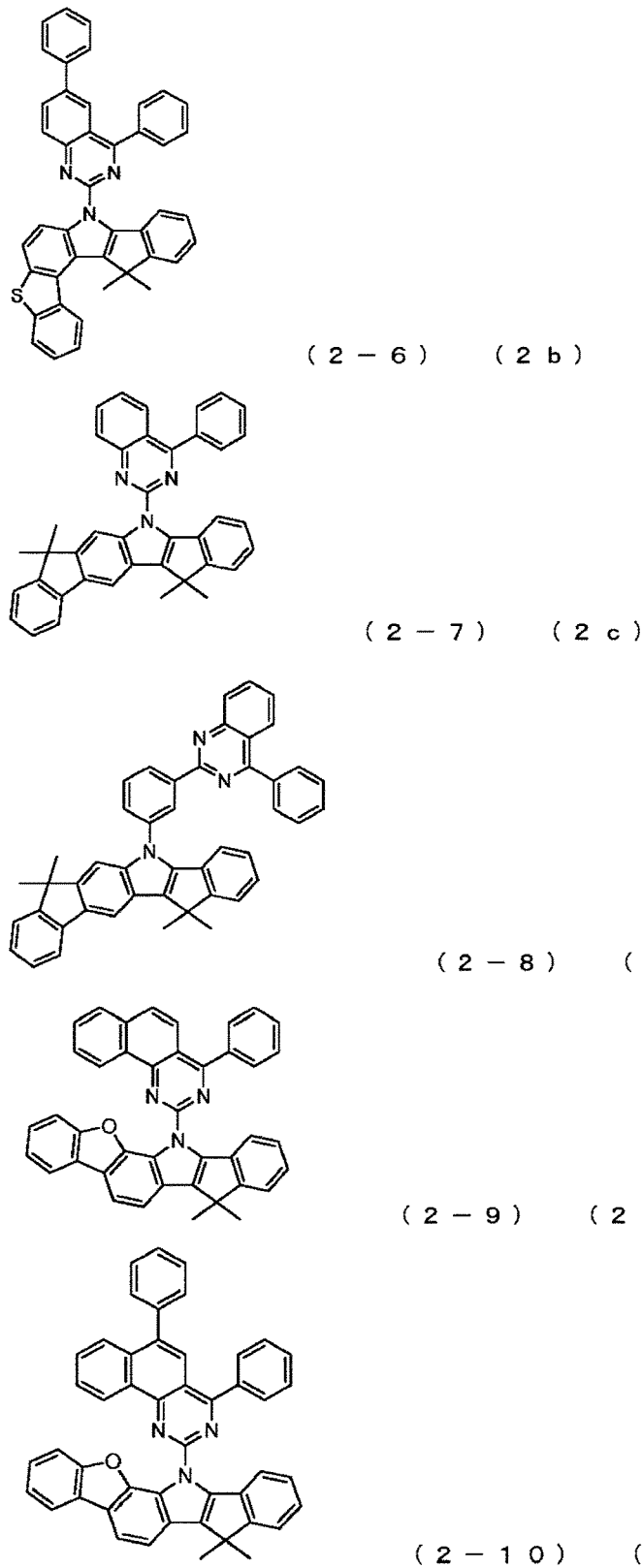
FIG. 21 is a diagram showing the structural formulas of Compound Nos. (2-6) to (2-10) that are N-aromatic substituted indenoindole derivatives of general formula (2).
Figure 22:
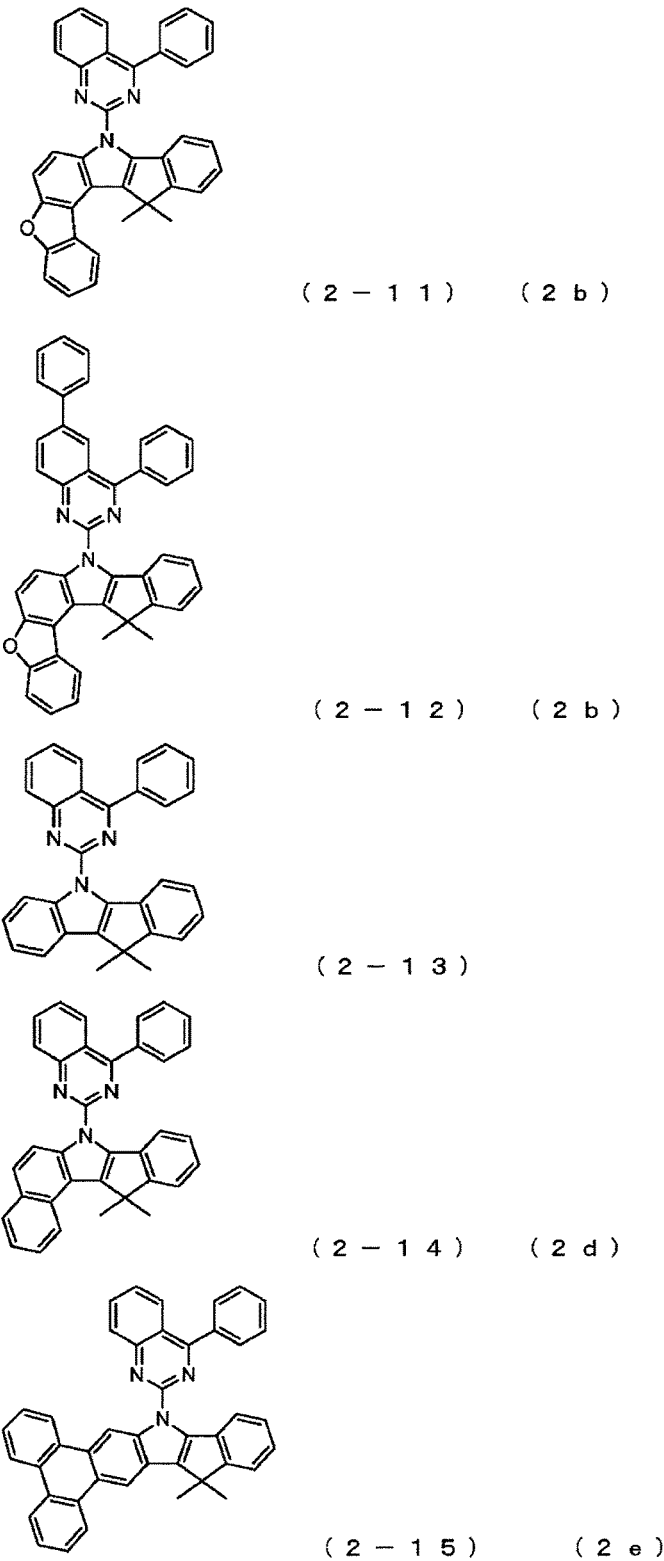
FIG. 22 is a diagram showing the structural formulas of Compound Nos. (2-11) to (2-15) that are N-aromatic substituted indenoindole derivatives of general formula (2).
Figure 23:
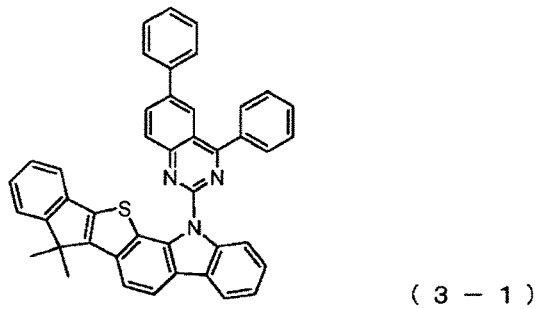
FIG. 23 is a diagram showing the structural formulas of Compound Nos. (3-1) to (3-5) that are N-aromatic substituted carbazole derivatives of general formula (3).
Figure 23:
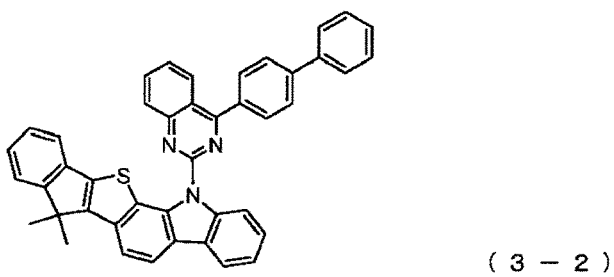
Figure 23:
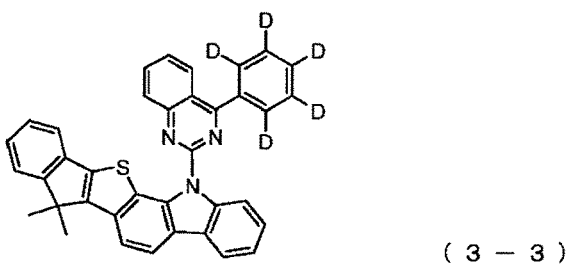
Figure 23:
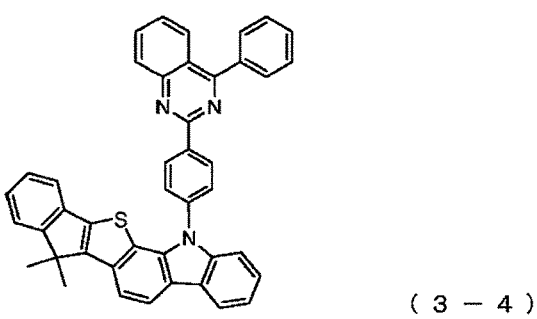
Figure 23:
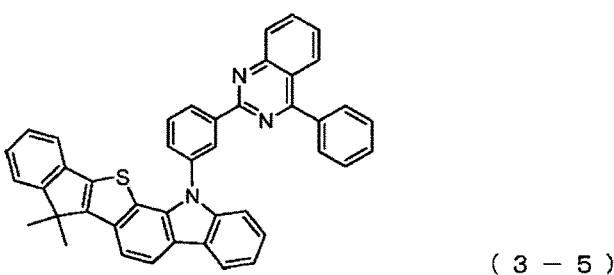
Figure 24:
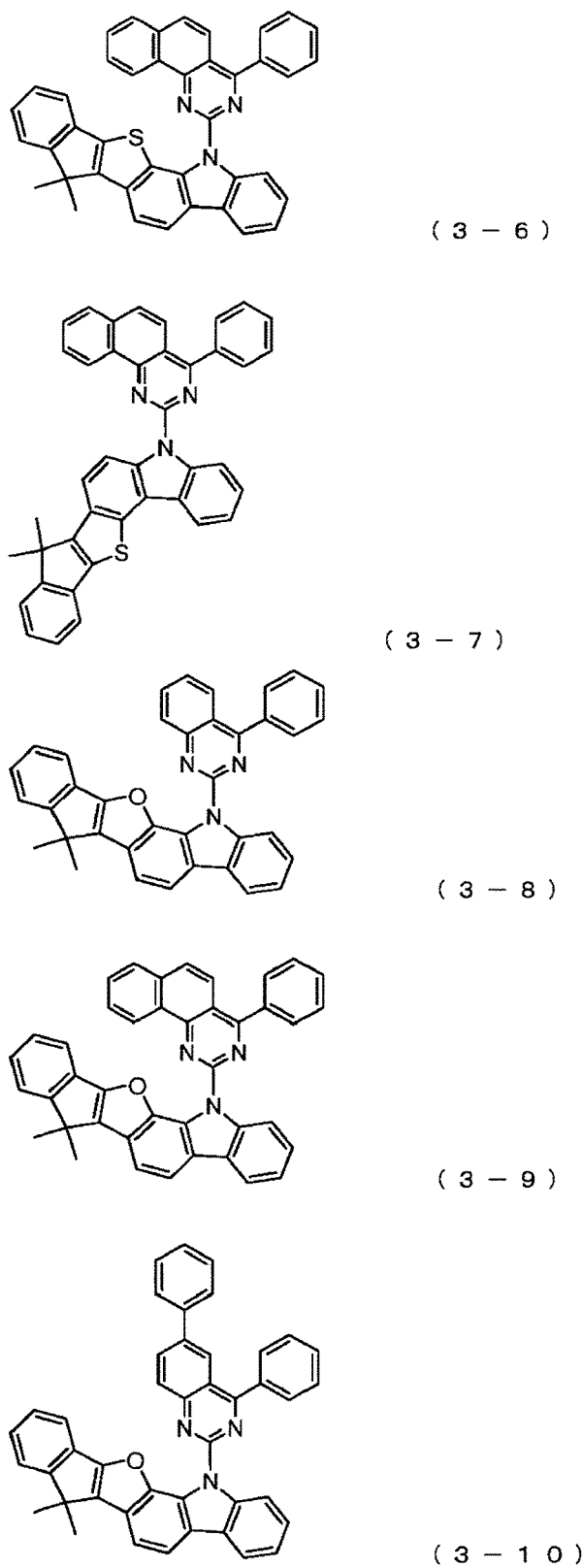
FIG. 24 is a diagram showing the structural formulas of Compound Nos. (3-6) to (3-10) that are N-aromatic substituted carbazole derivatives of general formula (3).
Figure 25:
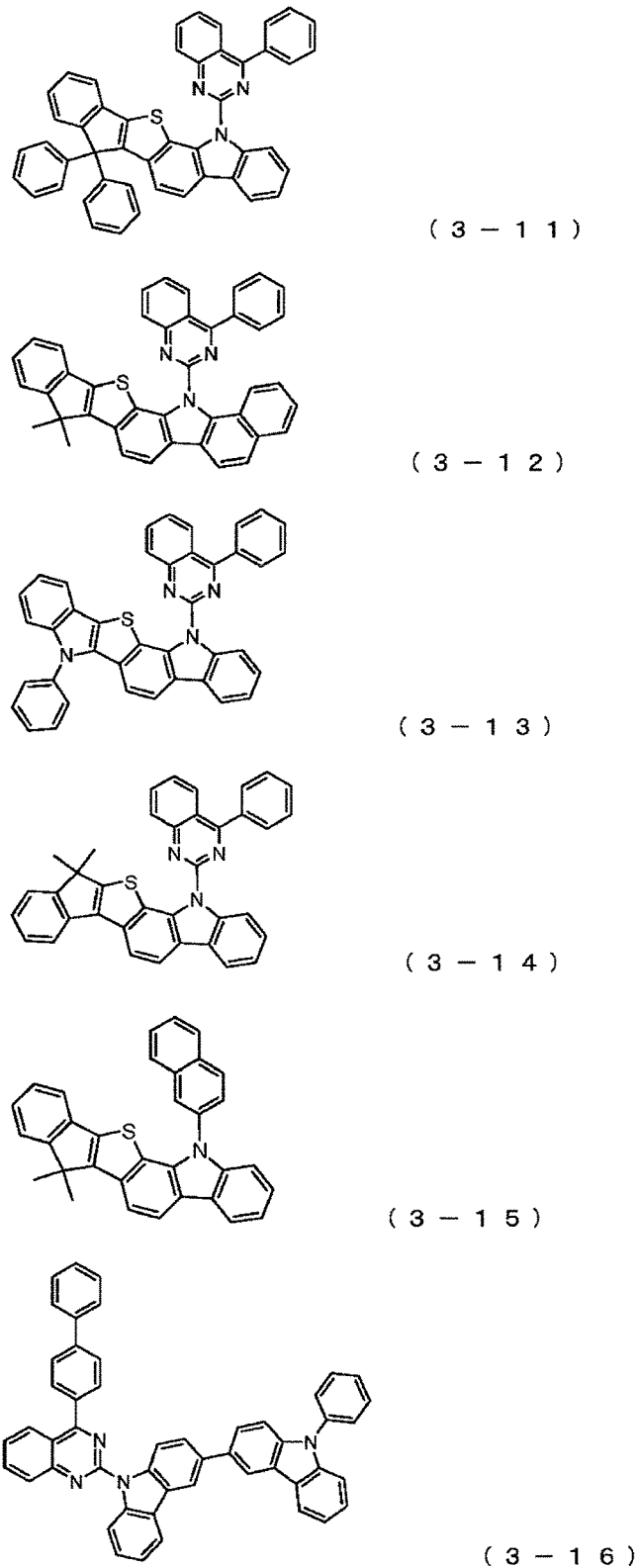
FIG. 25 is a diagram showing the structural formulas of Compound Nos. (3-11) to (3-16) that are N-aromatic substituted carbazole derivatives of general formula (3).
Figure 26:
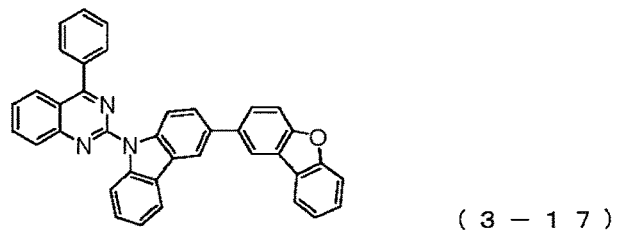
FIG. 26 is a diagram showing the structural formulas of Compound Nos. (3-17) to (3-21) that are N-aromatic substituted carbazole derivatives of general formula (3).
Figure 26:
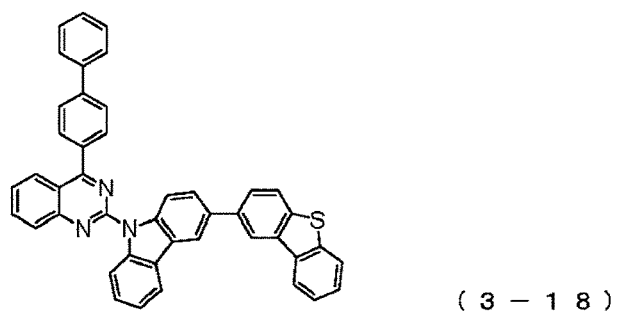
Figure 26:
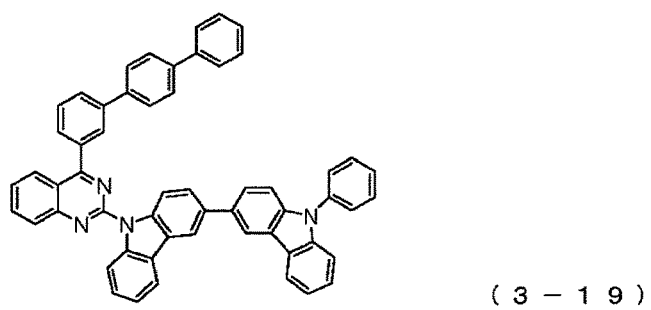
Figure 26:
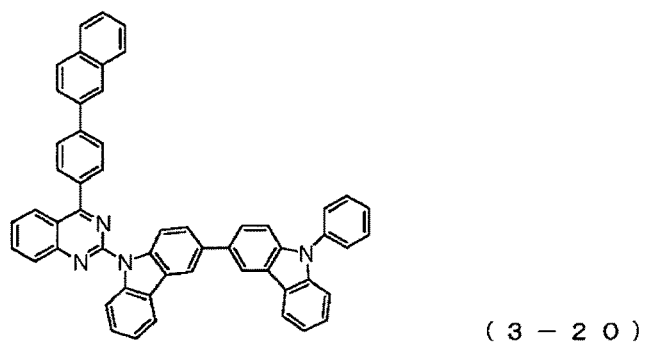
Figure 26:
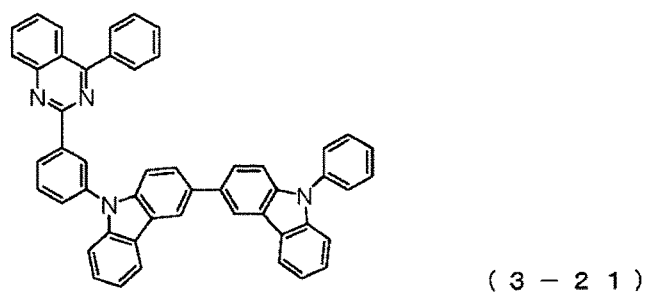
Figure 27:
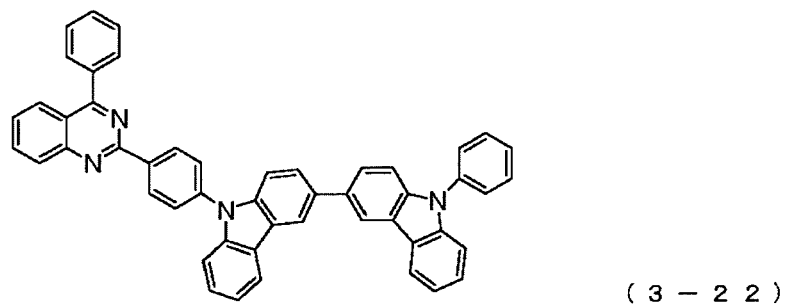
FIG. 27 is a diagram showing the structural formulas of Compound Nos. (3-22) and (3-23) that are N-aromatic substituted carbazole derivatives of general formula (3).
Figure 27:
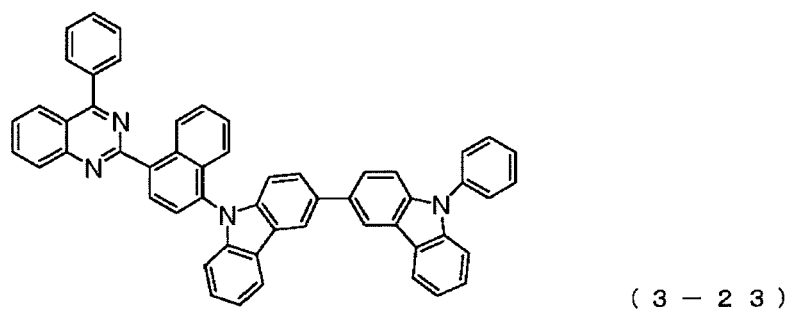
Figure 28:
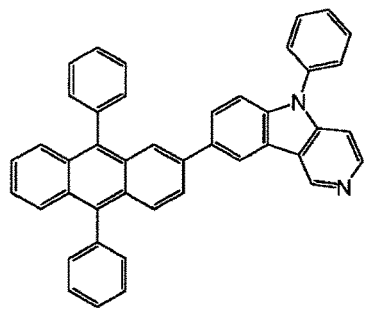
FIG. 28 is a diagram showing the structural formulas of Compound Nos. (4a-1) to (4a-5) that are anthracene derivatives of general formula (4a).
Figure 28:
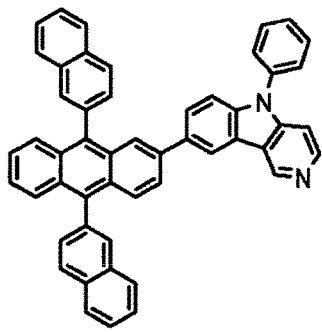
Figure 28:
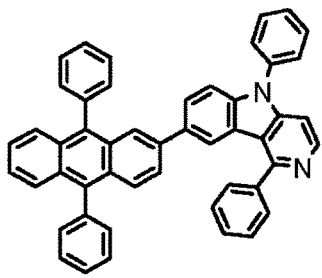
Figure 28:
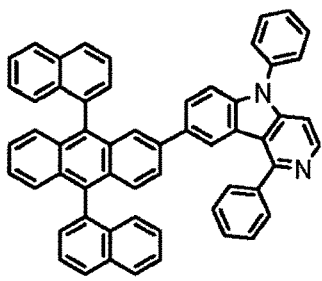
Figure 28:
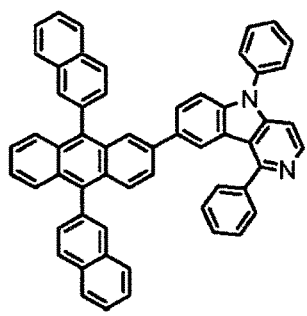
Figure 29:
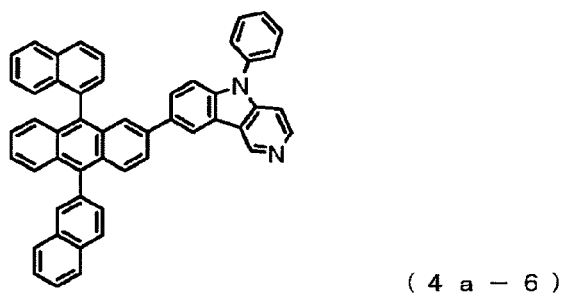
FIG. 29 is a diagram showing the structural formulas of Compound Nos. (4a-6) to (4a-10) that are anthracene derivatives of general formula (4a).
Figure 29:
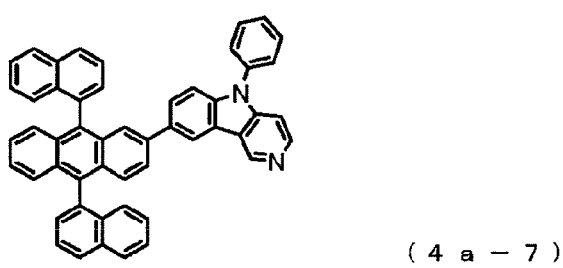
Figure 29:
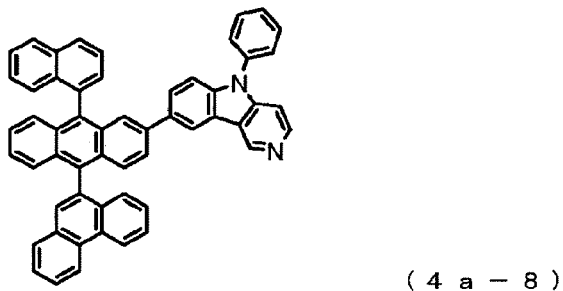
Figure 29:
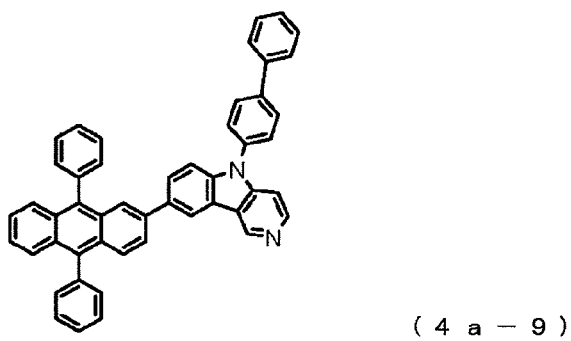
Figure 29:
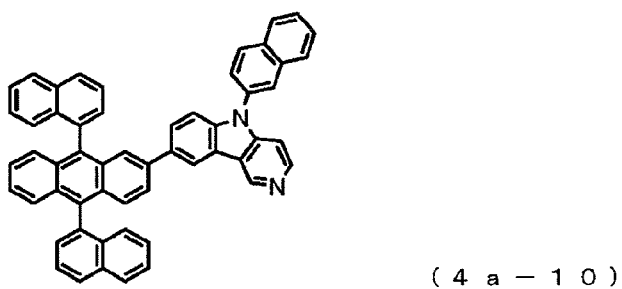
Figure 30:
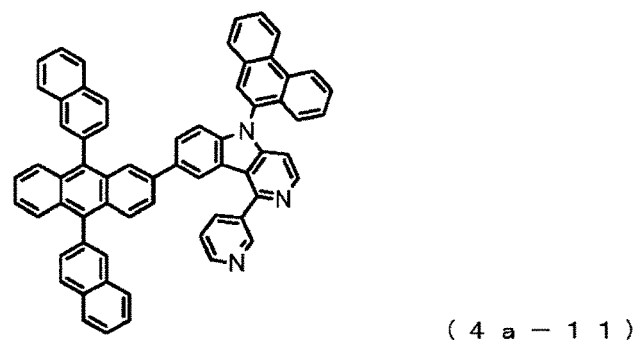
FIG. 30 is a diagram showing the structural formulas of Compound Nos. (4a-11) to (4a-15) that are anthracene derivatives of general formula (4a).
Figure 30:
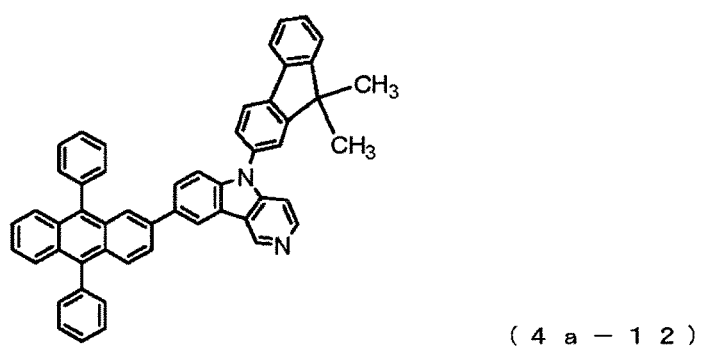
Figure 30:
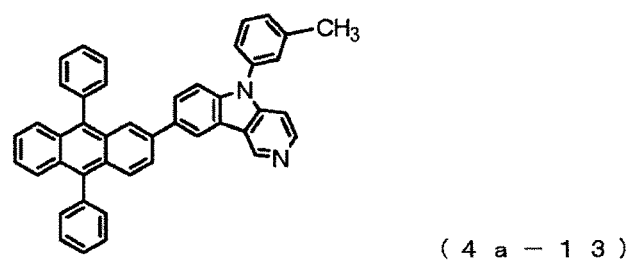
Figure 30:
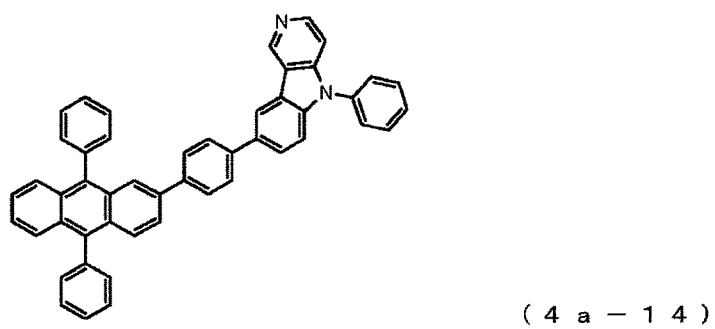
Figure 30:
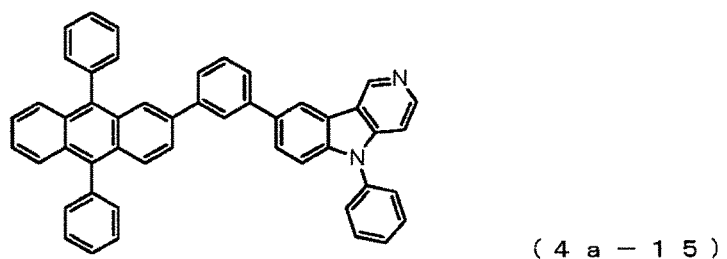
Figure 31:
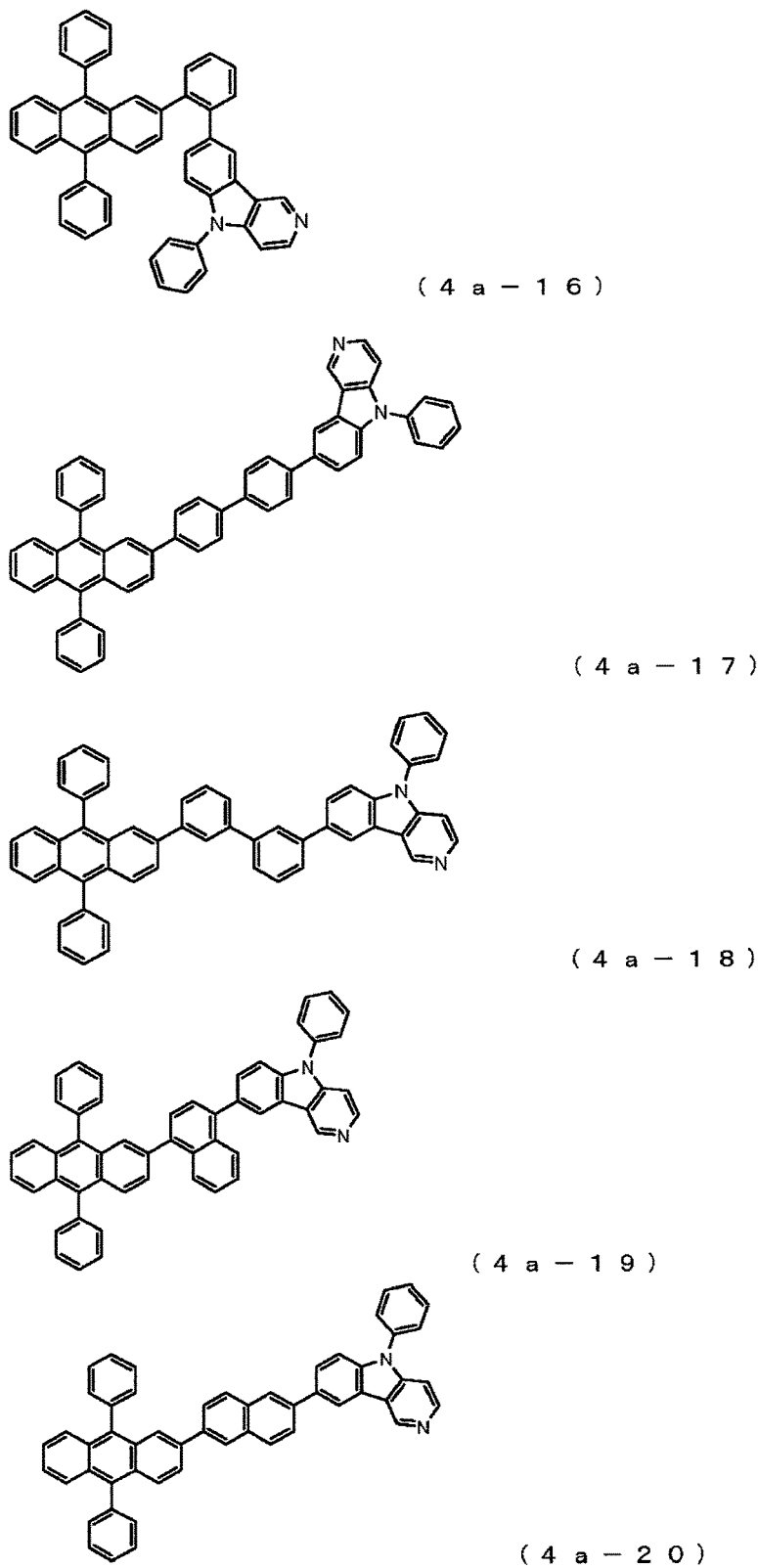
FIG. 31 is a diagram showing the structural formulas of Compound Nos. (4a-16) to (4a-20) that are anthracene derivatives of general formula (4a).

In the invention, specific examples of N-aromatic substituted indenoindole compounds of the above general formula (2) (or general formulas (2a) to (2e)) include Compounds (2-1) to (2-15) having the structural formulas shown in FIGS. 20 to 22.

In the invention, the N-aromatic substituted carbazole compound used to form the luminous layer 6 is a compound which has a carbazole ring structure and in which an aromatic group has been introduced onto the nitrogen atom in the carbazole ring. The carbazole compound is represented by, for example, the general formula (3) below.

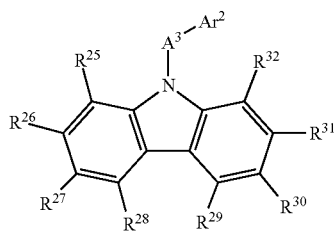

(3)

In the general formula (3), $A^3$ that bonds to the nitrogen atom, as with $A^1$ in the general formula (1) and $A^2$ in the general formula (2), is a divalent aromatic hydrocarbon group, a divalent aromatic heterocyclic group or a single bond.

These divalent aromatic hydrocarbon groups and divalent aromatic heterocyclic groups may be exemplified by the same groups exemplified for $A^1$ in the general formula (1) and $A^2$ in the general formula (2). These groups may have the same substituents exemplified for $A^1$. Moreover, these substituents may be bonded to each other via a single bond, a substituted or unsubstituted methylene group, an oxygen atom or a sulfur atom to form a ring.

$Ar^2$ in the above general formula (3) represents a monovalent aromatic hydrocarbon group or a monovalent aromatic heterocyclic group. These monovalent aromatic hydrocarbon groups and monovalent aromatic heterocyclic groups may be exemplified by the same groups exemplified for B in the general formula (1). These groups may have the same substituents exemplified for B. Moreover, these substituents may be bonded to each other via a single bond, a substituted or unsubstituted methylene group, an oxygen atom or a sulfur atom to form a ring.

$R^{25}$ to $R^{32}$ in the general formula (3) represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, an aralkyl group, an aryloxy group, or a disubstituted amino group having, as a substituent, a monovalent aromatic hydrocarbon group or a monovalent aromatic heterocyclic group.

The monovalent aromatic hydrocarbon group, monovalent aromatic heterocyclic group and other groups included as substituents on the disubstituted amino groups are exemplified by the groups mentioned as examples for B or $R^1$ to $R^{10}$ in the general formula (1). These groups too may be bonded to each other via a single bond, a methylene group which may have a substituent, an oxygen atom or a sulfur atom to forma ring (i.e., a condensed ring).

Also, some of $R^{25}$ to $R^{32}$ may be detached, and the remaining groups of $R^{25}$ to $R^{32}$ (especially a group adjacent to the group that has detached) may be bonded to vacancies generated by the detachment via a methylene group which may have a substituent, an oxygen atom, a sulfur atom or a monoarylamino group to form a ring (i.e., a condensed ring).

In this invention, it is preferable for a ring to be formed by $R^{25}$ to $R^{32}$. That is, a structure in which a ring is condensed to the benzene ring on the carbazole ring is preferred. In particular, as shown in the general formulas (3a-1) to (3a-4) and (3b-1) below, it is preferable for the adjacent group to bond to the vacant site where some of $R^{25}$ to $R^{32}$ has detached via a methylene group which may have a substituent, an oxygen atom, a sulfur atom or a monoarylamino group to form a ring.

In the following general formulas (3a-1) to (3a-4) and (3b-1), $A^3$, $Ar^2$ and $R^{25}$ to $R^{32}$ have the same meanings as indicated in the general formula (3), and X is a divalent linking group that represents a methylene group which may have a substituent, an oxygen atom, a sulfur atom or a monoarylamino group.

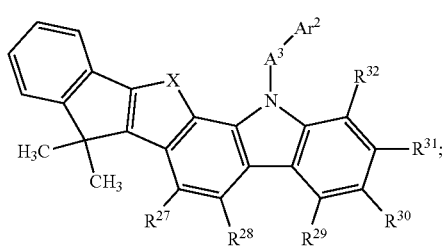

General Formula (3a-1)

The general formula (3a-1) has a structure in which, at the position in the benzene ring which is a vacant site since $R^{25}$ in the general formula (3) detaches, the $R^{26}$ group (an indenyl group having two methyl groups as substituents) adjacent to $R^{25}$ bonds through the linking group X to form a condensed ring.

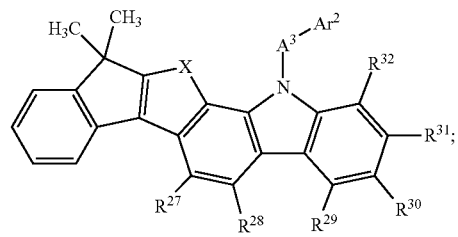

General Formula (3a-2)

The general formula (3a-2) as well has a structure wherein, as in the general formula (3a-1), at the position in the benzene ring which is a vacant site since $R^{25}$ in the general formula (3) detaches, the $R^{26}$ group (an indenyl group having two methyl groups as substituents) adjacent to $R^{25}$ bonds through the linking group X to form a condensed ring.

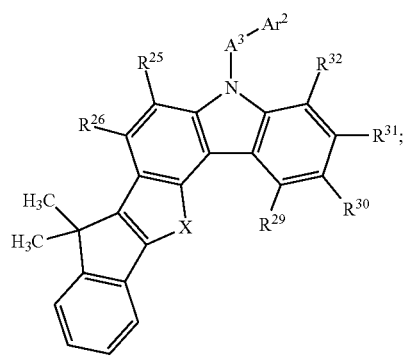

General Formula (3a-3)

The general formula (3a-3) has a structure in which, at the position in the benzene ring which is a vacant site since $R^{28}$ in the general formula (3) detaches, the $R^{27}$ group (an indenyl group having two methyl groups as substituents) adjacent to $R^{28}$ bonds through the linking group X to form a condensed ring.

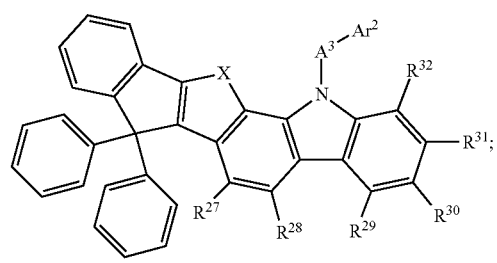

General Formula (3a-4)

The general formula (3a-4) has a structure in which, at the position in the benzene ring which is a vacant site since $R^{25}$ in the general formula (3) detaches, the $R^{26}$ group (an indenyl group having two phenyl groups as substituents) adjacent to $R^{25}$ bonds through the linking group X to form a condensed ring.

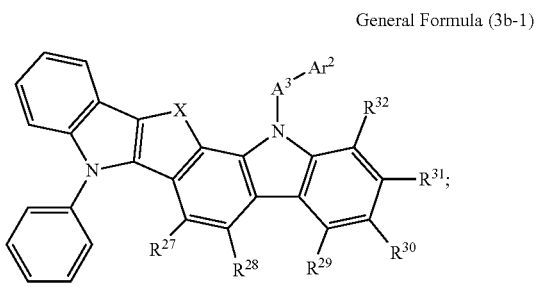

General Formula (3b-1)

The general formula (3b-1) has a structure in which, at the position in the benzene ring which is a vacant site since $R^{25}$ in the general formula (3) detaches, the $R^{26}$ group (an N-phenyl-substituted indolyl group) adjacent to $R^{25}$ bonds through the linking group X to form a condensed ring.

In the above general formulas (3a-1) to (3a-4), examples of condensed rings formed by bonding to the benzene ring through linking group X include an indenoindane ring (X=methylene), an indenoindole ring (X=a monophenylamino group), indenobenzofuran ring (X=an oxygen atom), an indenobenzothiophene ring (X=a sulfur atom) and so on.

General formulas (3a-1) to (3a-4) and (3b-1) above show structures in which $R^{25}$ to $R^{28}$ form a ring, but $R^{29}$ to $R^{32}$ may form a ring in the same way as in these formulas.

In this invention, specific examples of N-aromatic substituted carbazole compounds represented by the above-described general formula (3) (or general formulas (3a-1) to (3a-4) and (3b-1)) include Compounds (3-1) to (3-23) having the structural formulas shown in FIGS. 23 to 27.

The above N-aromatic substituted indenoindole compound and N-aromatic substituted carbazole compound have excellent properties as host materials for the luminous layer. By using these compounds, either individually or two or more together, in combination with an emitting material to form the luminous layer 6, full advantage is taken of the hole transporting and injecting properties of the indenoacridan derivative included in the above-described hole transport layer 5, making it possible to achieve a high luminous efficiency.

Although the N-aromatic substituted carbazole compound is preferably one represented by the general formula (3), apart from such carbazole compounds represented by the general formula (3), combination use can also be made of carbazole derivatives such as 4,4'-di(N-carbazolyl)biphenyl (CBP), TCTA or mCP.

Within a range that does not detract from the outstanding properties of the above N-aromatic substituted indenoindole compounds and N-aromatic substituted carbazole compounds, combination use can also be made of compounds that have hitherto been used together with emitting materials, including metal complexes of quinolinol derivatives (e.g., $Alq_3$) and various other metal complexes, anthracene derivatives, bis(styryl)benzene derivatives, pyrene derivatives, oxazole derivatives, poly(p-phenylene vinylene) derivatives, thiazole derivatives, benzimidazole derivatives, poly(dialkylfluorene) derivatives and quinazoline derivatives. In addition, combination use can also be made of compounds having electron-transporting properties, such as p-bis(triphenylsilyl)benzene (UGH2) and 2,2',2"-(1,3,5-phenylene)-tris(1-phenyl-1H-benzimidazole) (TPBI).

The emitting material is not particularly limited. One that is known in itself may be used, although the use of a phosphorescent luminous body is especially preferred in this invention.

The phosphorescent luminous body is typically a metal complex of iridium, platinum or the like. Examples of such phosphorescent luminous bodies that are metal complexes include red phosphorescent luminous bodies such as bis(3-methyl-2-phenylquinoline)iridium(III)acetylacetonate (Ir(3'-Mepq)$_2$(acac)), Ir(piq)$_3$ and Btp$_2$Ir(acac), green phosphorescent luminous bodies such as Ir(ppy)$_3$, and blue phosphorescent luminous bodies such as FIrpic and FIr6.

In this invention, of the above phosphorescent luminous bodies, a red phosphorescent luminous body is especially preferred.

In addition, materials which emit delayed fluorescence, including CDCB derivatives such as PIC-TRZ, CC2TA, PXZ-TRZ and 4CzIPN, may be used as the emitting material (see, for example, Appl. Phys. Let., 98, 0833302).

In the invention, the above emitting materials may be used as the dopant, and the above-mentioned N-aromatic substituted indenoindole compound or N-aromatic substituted carbazole compound and other materials may be used as the host material.

To avoid concentration quenching, doping of the host material with a phosphorescence emitting material is preferably carried out by co-vapor deposition in a range of 1 to 30 wt %, based on the entire luminous layer 6.

In this invention, the most preferred luminous layer 6 is one in which a red-emitting dopant (i.e., a red phosphorescent luminous body) is used.

When the luminous layer 6 is formed of a host material and a dopant as described above, dopant materials that may be used include quinacridone, coumarin, rubrene, perylene and derivatives thereof, benzopyran derivatives, rhodamine derivatives and aminostyryl derivatives.

<Electron Transport Layer 7>

In this invention, the electron transport layer 7 provided on the luminous layer 6 may be formed by a known method such as vapor deposition, spin coating or ink-jet printing using a known electron-transporting material.

The electron transport layer may be formed of an electron-transporting material that is known in itself, and use can be made of a metal complex of a quinolinol derivative such as Alq$_3$, complexes of various metals such as zinc, beryllium or aluminum, as well as triazole derivatives, triazine derivatives, oxadiazole derivatives, thiadiazole derivatives, carbodiimide derivatives, quinoxaline derivatives, phenanthroline derivatives, silole derivatives and so on.

Also, in this invention, it is preferable to form the electron transport layer by using an anthracene derivative represented by the following general formula (4) as the electron-transporting material. Such anthracene derivatives have excellent electron injecting and transporting abilities and excellent thin-film stability and durability. By combining an electron transport layer formed using such an anthracene derivative with a hole transport layer that includes the above-described indenoacridan derivative of the general formula (1), holes and electrons can be efficiently injected into the luminous layer 6. Thereby, it is possible to achieve an optimal carrier balance and greatly enhance the characteristics of the organic EL device.

(4)

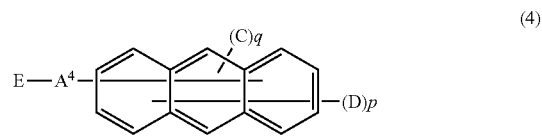

In the formula (4),

A⁴ is a divalent aromatic hydrocarbon group, a divalent aromatic heterocyclic group or a single bond, E is a monovalent aromatic heterocyclic group, C is a monovalent aromatic hydrocarbon group or a monovalent aromatic heterocyclic group, D is a hydrogen atom, a deuterium atom, a fluorine atom, a chlorine atom, a cyano group or an alkyl group having 1 to 6 carbon atoms, and p is the number 7 or 8 and q is the number 1 or 2, with the proviso that the sum of p and q is 9.

As is apparent from the general formula (4), this anthracene derivative has a molecular structure in which the anthracene ring and the group E are linked via a divalent group or a single bond. One or two monovalent aromatic hydrocarbon groups or monovalent aromatic heterocyclic groups (group C) are bonded as substituents to the anthracene ring to which group E is linked.

In this general formula (4), A⁴ represents a single bond or a divalent group, this divalent group being a divalent aromatic hydrocarbon group or a divalent aromatic heterocyclic group. Specific examples, which are the same as those mentioned for A¹ in the general formula (1), are given below.

The divalent aromatic hydrocarbon group is formed of an aromatic hydrocarbon ring having two sites available for bonding. Examples of such aromatic hydrocarbon rings include benzene, biphenyl, terphenyl, tetrakisphenyl, styrene, naphthalene, anthracene, acenaphthylene, fluorene, phenanthrene, indane, pyrene and triphenylene.

The divalent aromatic heterocyclic group is formed of an aromatic heterocycle having two sites available for bonding, Examples of such aromatic heterocycles include pyridine, pyrimidine, triazine, pyrrole, furan, thiophene, quinoline, isoquinoline, benzofuran, benzothiophene, indoline, carbazole, carboline, benzoxazole, benzothiazole, quinoxaline, benzoimidazole, pyrazole, dibenzofuran, dibenzothiophene, naphthyridine, phenanthroline and acridine.

These aromatic hydrocarbon rings and aromatic heterocycles may have substituents that can be introduced thereon without detracting from the outstanding properties of the anthracene derivative.

Such substituents are the same as the substituents that may be present on the monovalent aromatic hydrocarbon groups or monovalent aromatic heterocyclic groups represented by R¹ to R¹⁰ in the above general formula (1).

In the invention, especially preferred divalent groups are those from substituted or unsubstituted benzene rings, biphenyl rings, naphthalene rings and phenanthrene rings.

Also, the group E in the general formula (4) is a monovalent aromatic heterocyclic group. The heterocyclic group is exemplified by triazinyl, pyridyl, pyrimidinyl, furyl, pyrrolyl, thienyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl, naphthyridinyl, phenanthrolinyl, acridinyl, carbolinyl groups and so on.

The monovalent aromatic heterocyclic group in above group E may have substituents which do not detract from the outstanding properties of this anthracene derivative. Such substituents are exemplified by, in addition to a deuterium atom, a cyano group and a nitro group, the following groups.

halogen atoms such as fluorine, chlorine, bromine and iodine atoms;

alkyl groups having 1 to 6 carbon atoms, such as methyl, ethyl, n-propyl, isopropyl, n-butyl, isobutyl, tert-butyl, n-pentyl, isopentyl, neopentyl and n-hexyl groups;

cycloalkyl groups having 5 to 10 carbon atoms, such as cyclopentyl, cyclohexyl, 1-adamantyl and 2-adamantyl groups;

alkyloxy groups having 1 to 6 carbon atoms, such as methyloxy, ethyloxy and propyloxy groups;

cycloalkyloxy groups having 5 to 10 carbon atoms, such as cyclopentyloxy, cyclohexyloxy, 1-adamantyloxy and 2-adamantyloxy groups;

alkenyl groups such as vinyl and allyl groups;

aryloxy groups such as phenyloxy, tolyloxy, biphenylyloxy, naphthyloxy, anthracenyloxy and phenanthrenyloxy groups;

arylalkyloxy groups such as benzyloxy and phenethyloxy groups;

aromatic hydrocarbon groups such as phenyl, biphenylyl, terphenylyl, naphthyl, anthracenyl, phenanthrenyl, fluorenyl, indenyl, pyrenyl, perylenyl, fluoranthenyl and triphenylenyl groups;

aromatic heterocyclic groups such as pyridyl, pyrimidinyl, triazinyl, thienyl, furyl, pyrrolyl, quinolyl, isoquinolyl, benzofuranyl, benzothienyl, indolyl, carbazolyl, benzoxazolyl, benzothiazolyl, quinoxalinyl, benzoimidazolyl, pyrazolyl, dibenzofuranyl, dibenzothienyl and carbolinyl groups;

arylvinyl groups such as styryl and naphthylvinyl groups;

acyl groups such as acetyl and benzoyl groups;

These substituents may be present independently or may be bonded to each other via a single bond, a methylene group which may have a substituent, an oxygen atom or a sulfur atom to form a ring.

In the invention, monovalent aromatic heterocyclic groups that are suitable as above group E include nitrogen-containing aromatic heterocyclic groups such as pyridyl, pyrimidinyl, pyrrolyl, quinolyl, isoquinolyl, indolyl, carbazolyl, benzoxazolyl, benzothiazolyl, quinoxalinyl, benzoimidazolyl, pyrazolyl and carbolinyl groups. Of these, pyridyl, pyrimidinyl, quinolyl, isoquinolyl, indolyl, pyrazolyl, benzoimidazolyl and carbolinyl groups are more preferred.

Also, C in the general formula (4) represents a monovalent aromatic hydrocarbon group or a monovalent aromatic heterocyclic group. These groups are exemplified by the same groups exemplified for R¹ to R¹⁰ in the general formula (1). These monovalent aromatic hydrocarbon groups and monovalent aromatic heterocyclic groups too, as with the above-described aromatic groups represented by R¹ to R¹⁰, may have substituents.

When two such groups C are present on the molecule (q=2 in the formula (4)), the two groups C may be the same or different.

In addition, D in the general formula (4) is a hydrogen atom, a deuterium atom, a fluorine atom, a chlorine atom, a cyano group or an alkyl group having 1 to 6 carbon atoms. Of these, examples of these alkyl groups having 1 to 6 carbon atoms include methyl, ethyl, n-propyl, isopropyl, n-butyl, isobutyl, tert-butyl, n-pentyl, isopentyl, neopentyl and n-hexyl groups.

These alkyl groups too may have a substituent such as a deuterium atom, a fluorine atom, a chlorine atom or a cyano group.

The plurality of groups D that are present may each be the same or different.

In this invention, D is most preferably a hydrogen atom.

In the anthracene derivative of the general formula (4) above, it is preferable for E to be a nitrogen-containing aromatic heterocyclic group and for D to be a hydrogen atom. Such preferred anthracene derivatives are represented in particular by the general formula (4a), (4b) or (4c) below.

Anthracene derivatives represented by the general formula (4a);

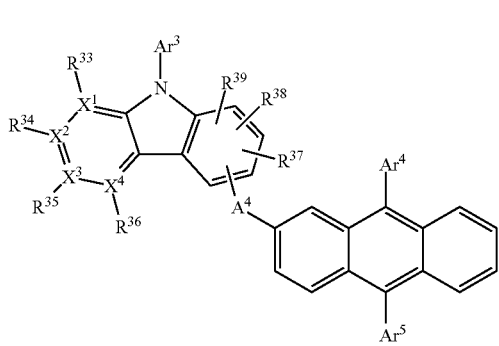

(4a)

In the general formula (4a), $A^4$ is, as in the formula (4), a divalent aromatic hydrocarbon group, a divalent aromatic heterocyclic group or a single bond.

Also, the nitrogen-containing heterocycle having a three-ring structure to which $A^4$ is bonded corresponds to group E in the general formula (4).

$X^2$, $X^3$ and $X^4$ in above formula (4a) are endocyclic elements which make up part of the nitrogen-containing heterocycle and each of which represents a carbon atom or a nitrogen atom, provided that only one of these is a nitrogen atom.

Also $R^{33}$ to $R^{39}$ and $Ar^3$ represent groups that are bonded to this nitrogen-containing heterocycle.

That is, $R^{33}$ to $R^{36}$ are shown as substituents on the ring formed by $X^1$, $X^2$, $X^3$ and $X^4$. However, when this endocyclic element is a nitrogen atom, none of $R^{33}$ to $R^{36}$ (including hydrogen atoms) are bonded to this nitrogen atom. This means that, for example, when $X^1$ is a nitrogen atom, $R^{33}$ does not exist, when $X^2$ is a nitrogen atom, $R^{34}$ does not exist, when $X^3$ is a nitrogen atom, $R^{35}$ does not exist, and when $X^4$ is a nitrogen atom, $R^{36}$ does not exist.

The groups $R^{33}$ to $R^{39}$ bonded to the nitrogen-containing heterocycle each represent a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group or an aryloxy group.

The alkyl group having 1 to 6 carbon atoms is exemplified by the same groups exemplified for D in the general formula (4) above.

Examples of the cycloalkyl group having 5 to 10 carbon atoms include cyclopentyl, cyclohexyl, 1-adamantyl and 2-adamantyl groups.

Examples of the alkenyl group having 2 to 6 carbon atoms include vinyl, allyl, isopropenyl and 2-butenyl groups.

Examples of the alkyloxy group having 1 to 6 carbon atoms include methyloxy, ethyloxy, n-propyloxy, isopropyloxy, n-butyloxy, tert-butyloxy, n-pentyloxy and n-hexyloxy groups.

Examples of the cycloalkyloxy group having 5 to 10 carbon atoms include cyclopentyloxy, cyclohexyloxy, cycloheptyloxy, cyclooctyloxy, 1-adamantyloxy and 2-adamantyloxy groups.

The monovalent aromatic hydrocarbon group and monovalent aromatic heterocyclic group are exemplified by the same groups exemplified for $R^1$ to $R^{10}$ in the general formula (1).

Examples of the aryloxy group include phenyloxy, biphenylyloxy, terphenylyloxy, naphthyloxy, anthracenyloxy, phenanthrenyloxy, fluorenyloxy, indenyloxy, pyrenyloxy and perylenyloxy groups.

The respective groups represented by $R^{33}$ to $R^{39}$ above may have substituents. These substituents are exemplified by, within a range that satisfies the conditions regarding the number of carbons, the same substituents exemplified as those possessed by groups $R^1$ to $R^{10}$ in the general formula (1).

Also, these substituents may each be present independently or may be bonded to each other via a single bond, a methylene group which may have a substituent, an oxygen atom or a sulfur atom to form a ring.

In addition, $Ar^3$ in the above general formula (4a) is a substituent that is bonded to the above nitrogen-containing aromatic ring, and $Ar^4$ and $Ar^5$ correspond to C in the general formula (4) (i.e., q=2).

$Ar^3$ to $Ar^5$ represent a monovalent aromatic hydrocarbon group or a monovalent aromatic heterocyclic group. These groups are exemplified by the same groups exemplified for $R^1$ to $R^{10}$ in the general formula (1). These monovalent aromatic hydrocarbon groups and monovalent aromatic heterocyclic groups too, as with the aromatic groups represented by $R^1$ to $R^{10}$ above, may have substituents.

Specific examples of anthracene derivatives represented by the above general formula (4a) include Compounds (4a-1) to (4a-20) having the structural formulas shown in FIGS. 28 to 31.

Of the anthracene derivatives represented by the general formula (4a) above, those represented by the following general formula (4a') are most preferred.

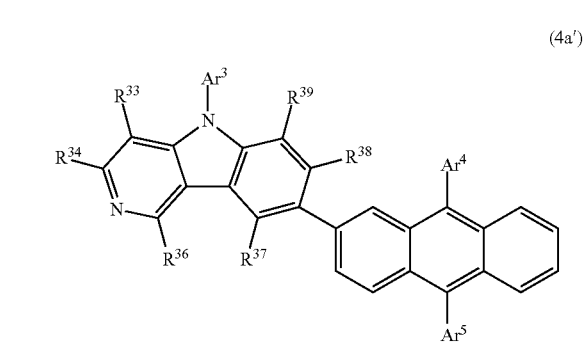

(4a')

In the general formula (4a'), $R^{33}$ to $R^{39}$ and $Ar^3$ to $Ar^5$ have the same meanings as in the general formula (4a).

Anthracene derivatives represented by the general formula (4b);

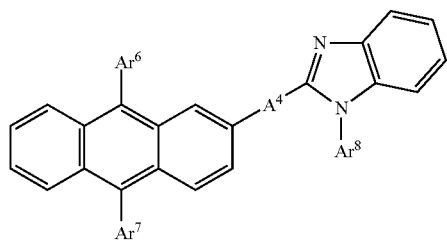

(4b)

In the general formula (4b), $A^4$ is, as in the formula (4), a divalent aromatic hydrocarbon group, a divalent aromatic heterocyclic group or a single bond.

Also, the nitrogen-containing heterocycle to which $A^4$ is bonded corresponds to group E in the general formula (4).

In addition, $Ar^6$ and $Ar^7$ in the general formula (4b) above correspond to C in the general formula (4) (i.e., q=2), and $Ar^8$ is a substituent bonded to the nitrogen-containing aromatic ring.

$Ar^6$ to $Ar^8$ represent a monovalent aromatic hydrocarbon group or a monovalent aromatic heterocyclic group. The examples of these groups are exemplified by the same groups as the monovalent aromatic hydrocarbon groups or monovalent aromatic heterocyclic groups represented by $R^1$ to $R^{10}$ in the general formula (1). Moreover, these monovalent aromatic hydrocarbon groups and monovalent aromatic heterocyclic groups, as with the groups represented by $R^1$ to $R^{10}$ in the general formula (1), may have substituents.

Figure 32:
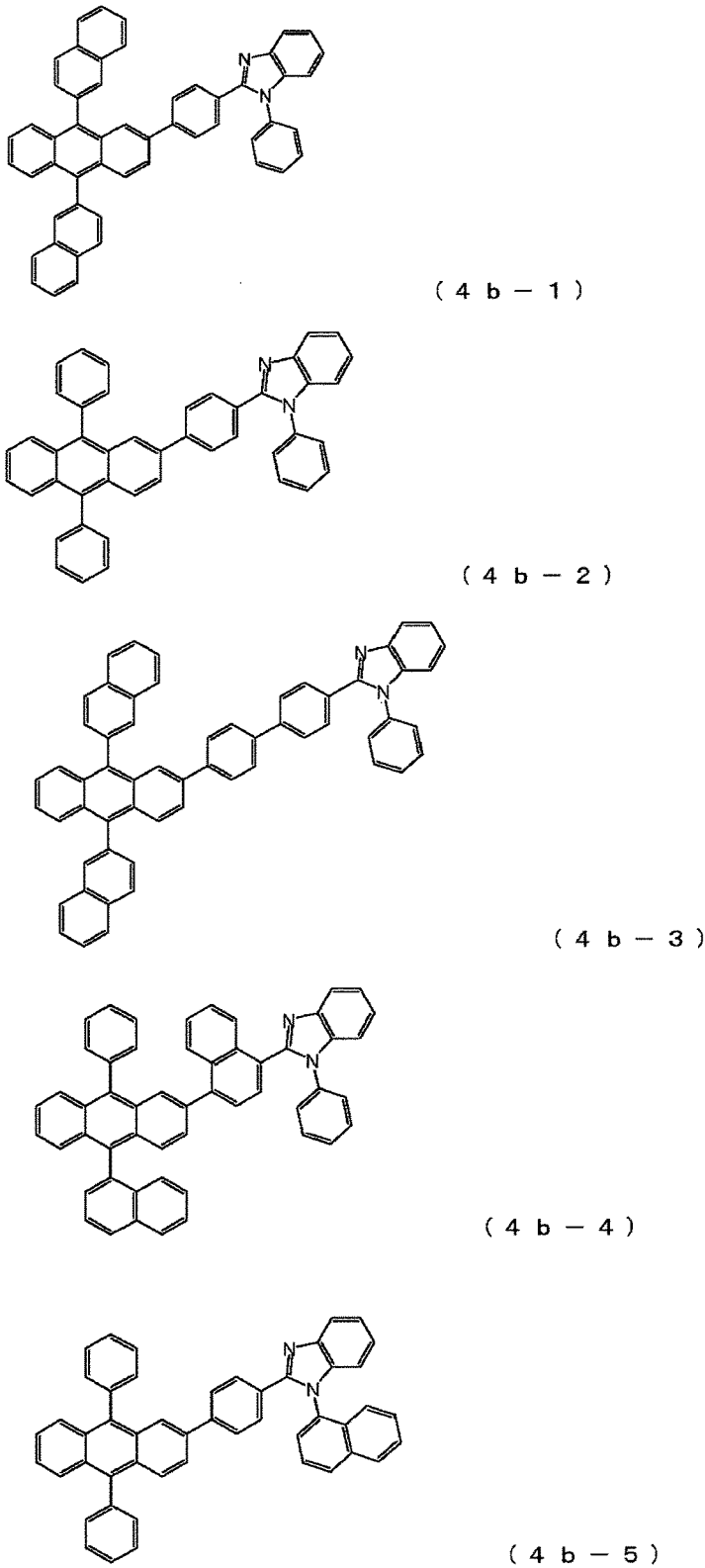
FIG. 32 is a diagram showing the structural formulas of Compound Nos. (4b-1) to (4b-5) that are anthracene derivatives of general formula (4b).
Figure 33:
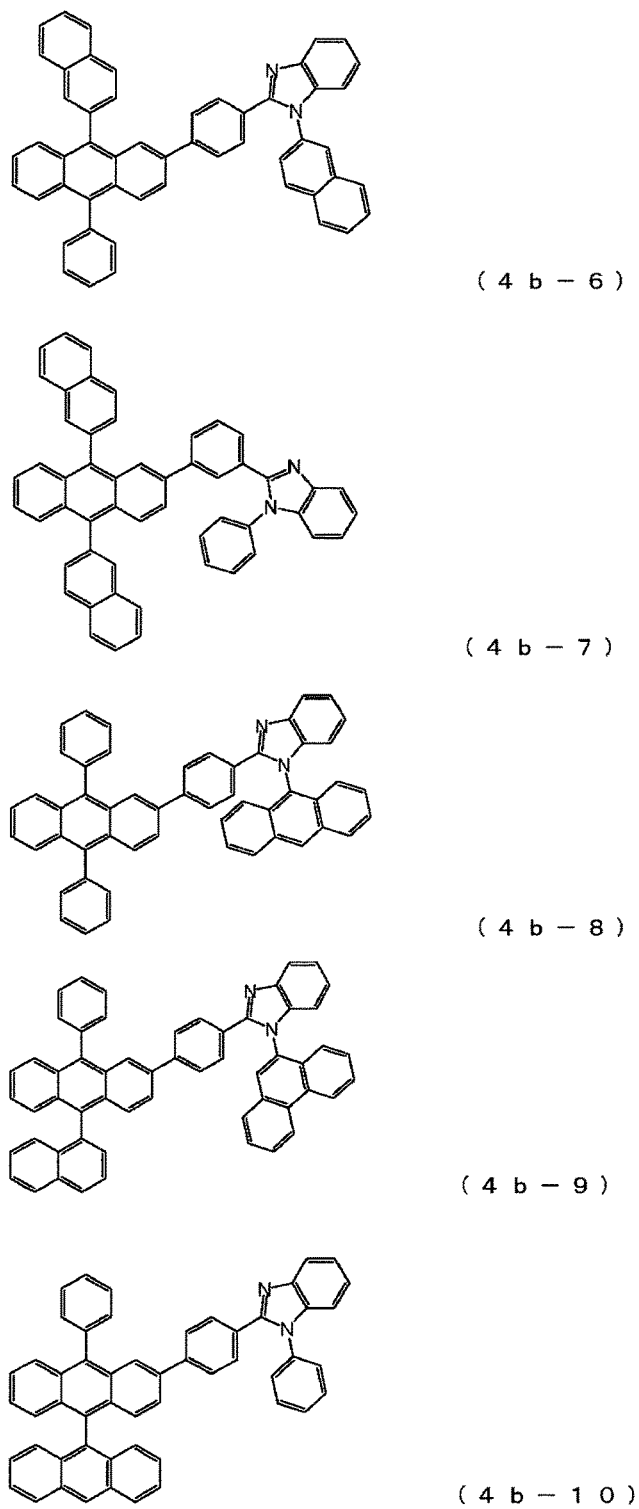
FIG. 33 is a diagram showing the structural formulas of Compound Nos. (4b-6) to (4b-10) that are anthracene derivatives of general formula (4b).
Figure 34:
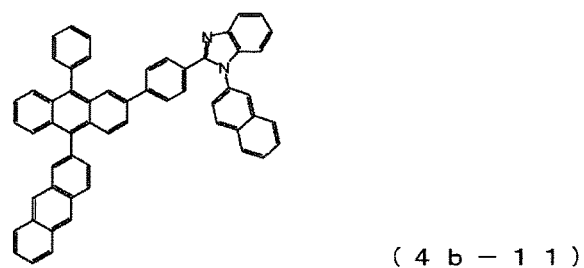
FIG. 34 is a diagram showing the structural formulas of Compound Nos. (4b-11) to (4b-16) that are anthracene derivatives of general formula (4b).
Figure 34:
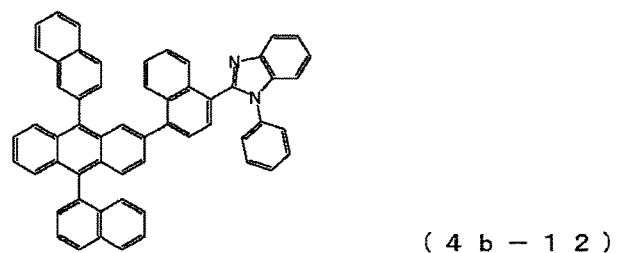
Figure 34:
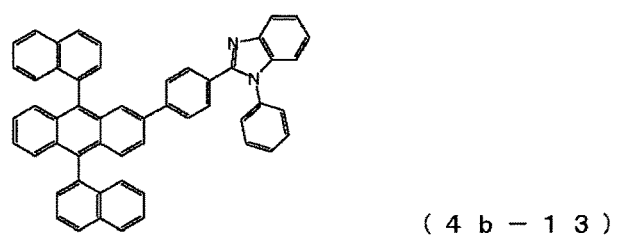
Figure 34:
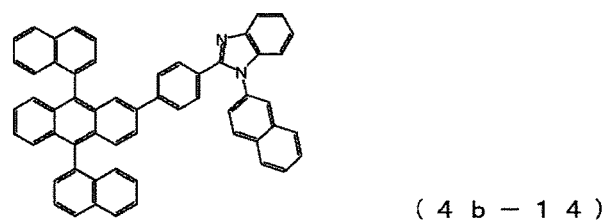
Figure 34:
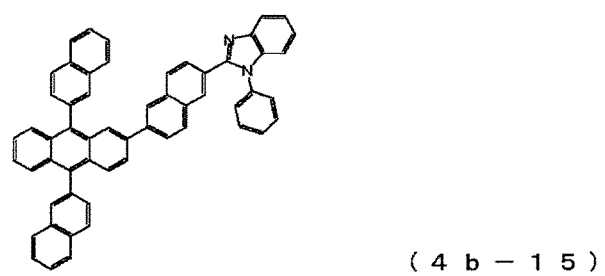
Figure 34:
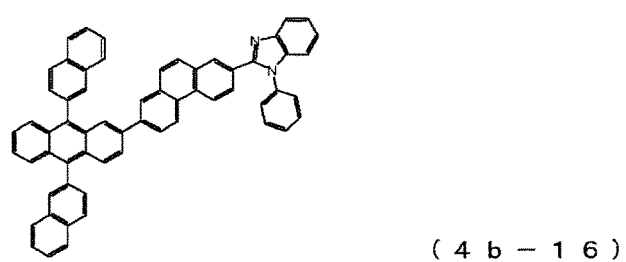
Figure 35:
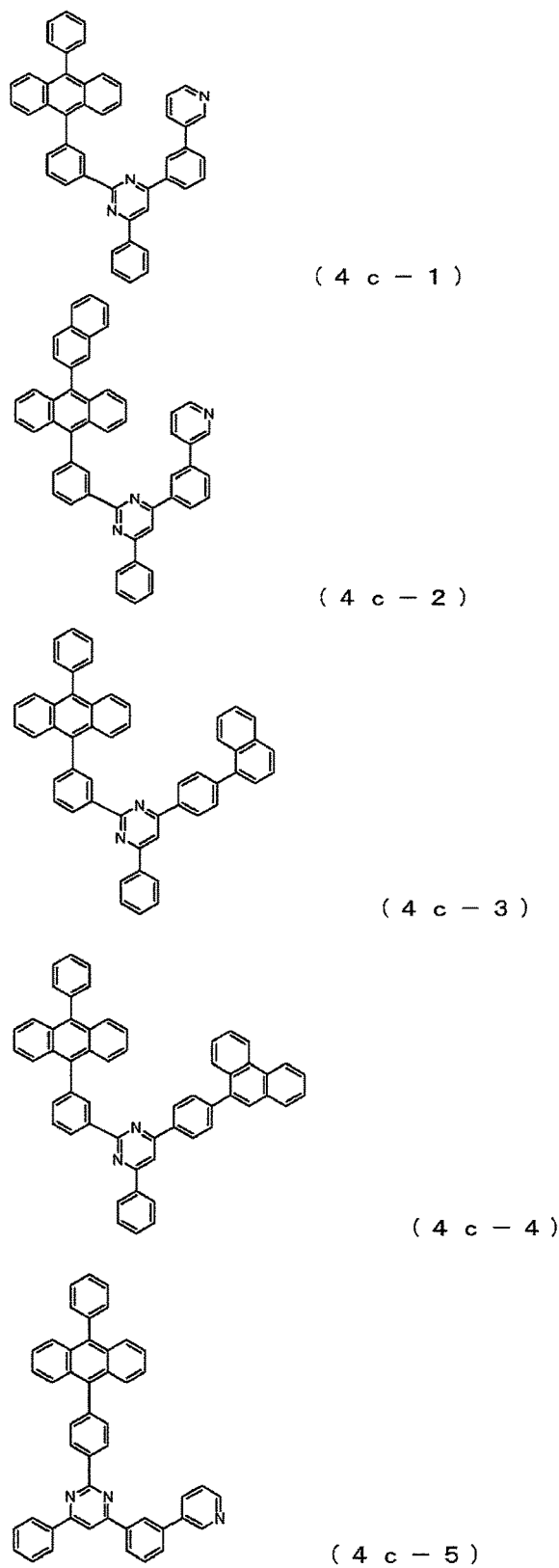
FIG. 35 is a diagram showing the structural formulas of Compound Nos. (4c-1) to (4c-5) that are anthracene derivatives of general formula (4c).
Figure 36:
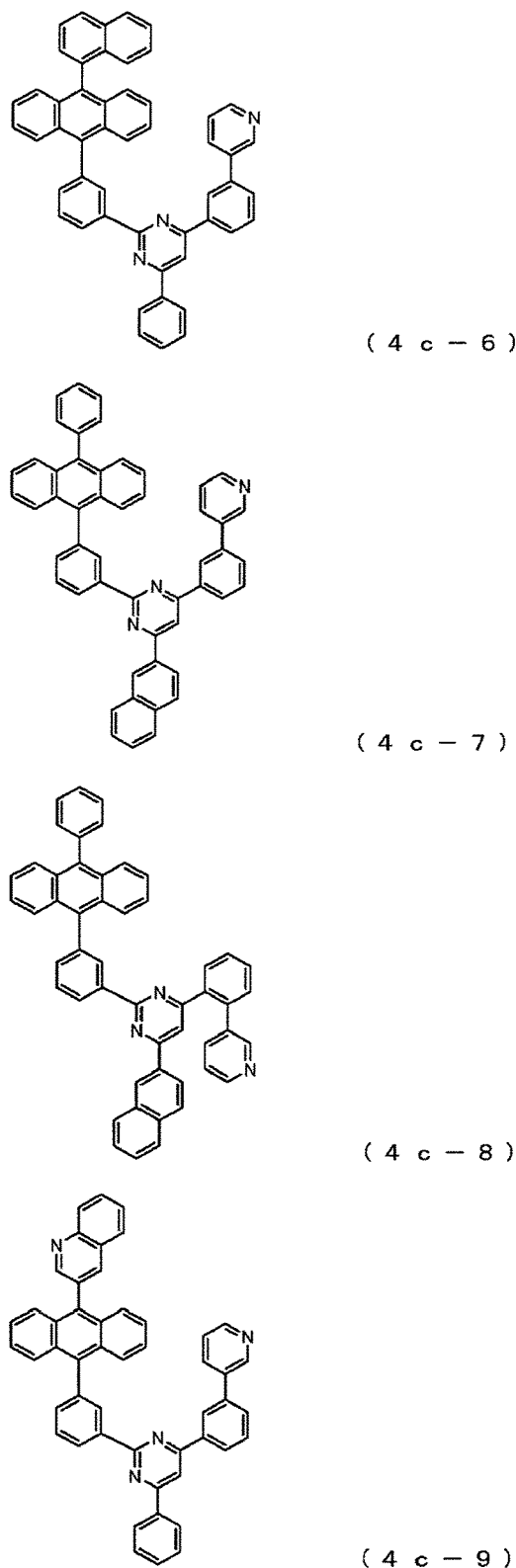
FIG. 36 is a diagram showing the structural formulas of Compound Nos. (4c-6) to (4c-9) that are anthracene derivatives of general formula (4c).
Figure 37:
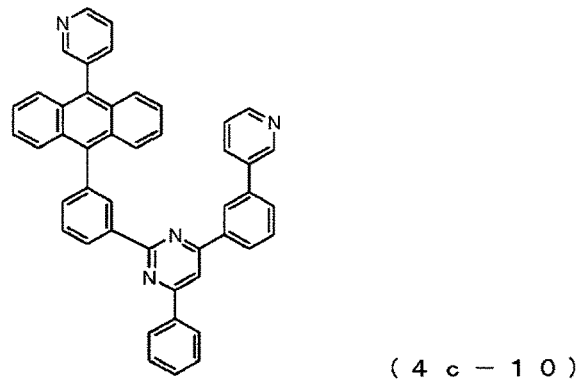
FIG. 37 is a diagram showing the structural formulas of Compound Nos. (4c-10) to (4c-13) that are anthracene derivatives of general formula (4c).
Figure 37:
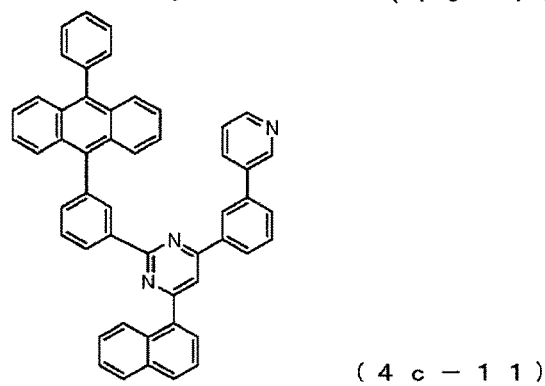
Figure 37:
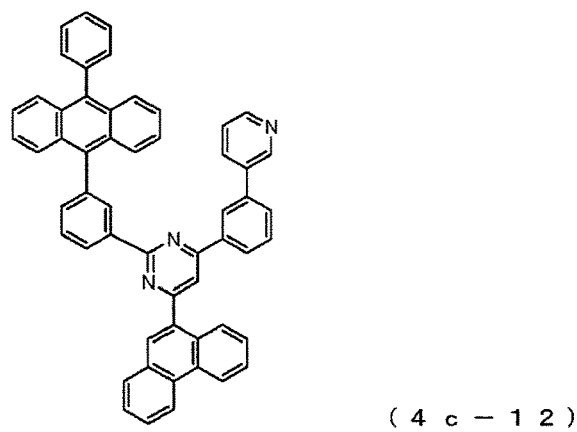
Figure 37:
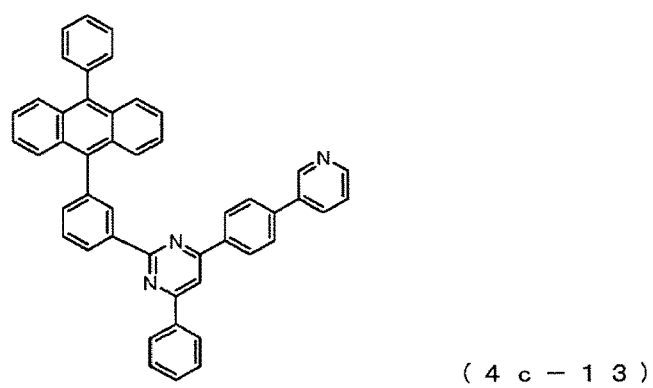
Figure 38:
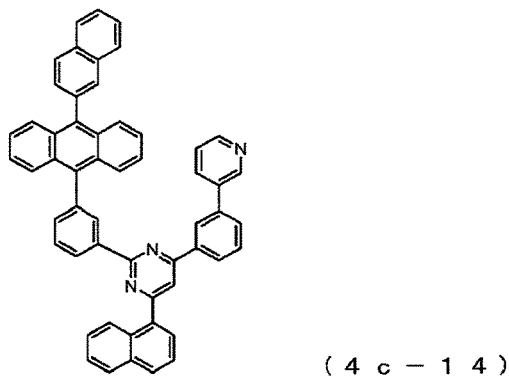
FIG. 38 is a diagram showing the structural formulas of Compound Nos. (4c-14) to (4c-17) that are anthracene derivatives of general formula (4c).
Figure 38:
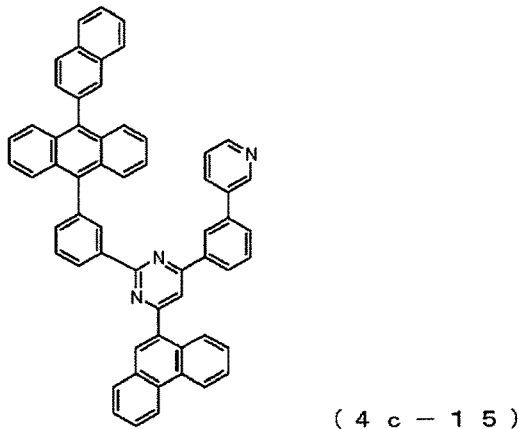
Figure 38:
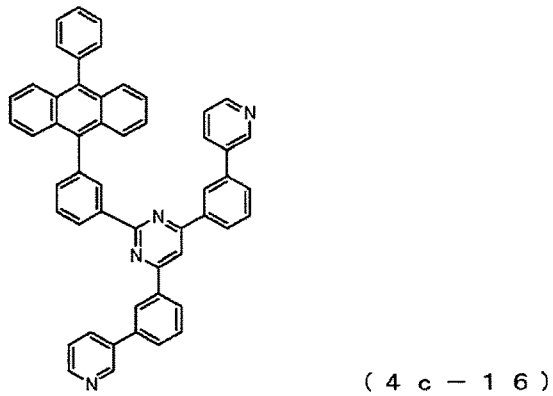
Figure 38:
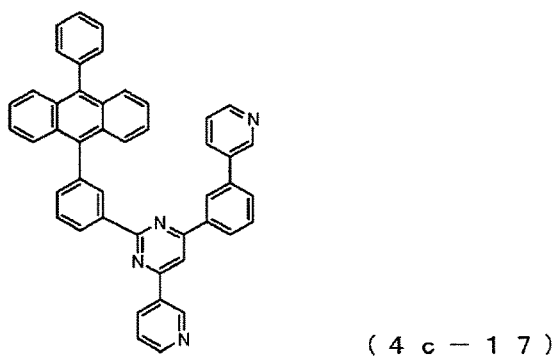
Figure 39:
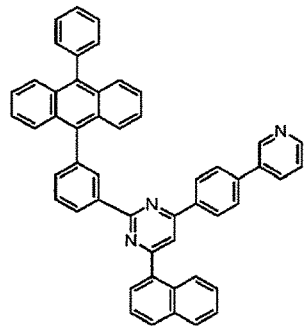
FIG. 39 is a diagram showing the structural formulas of Compound Nos. (4c-18) to (4c-21) that are anthracene derivatives of general formula (4c).
Figure 39:
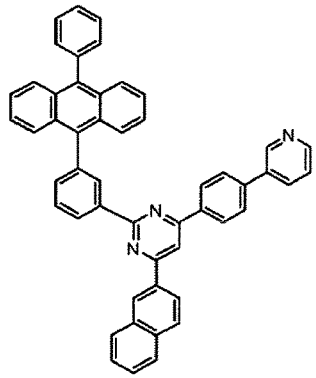
Figure 39:
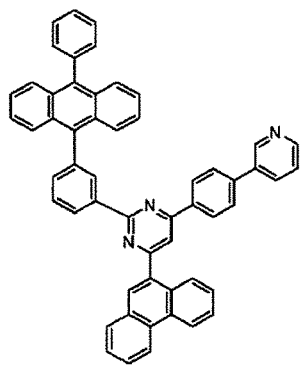
Figure 39:
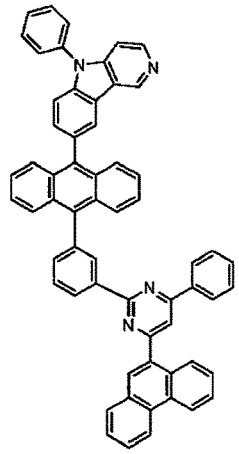
Figure 40:
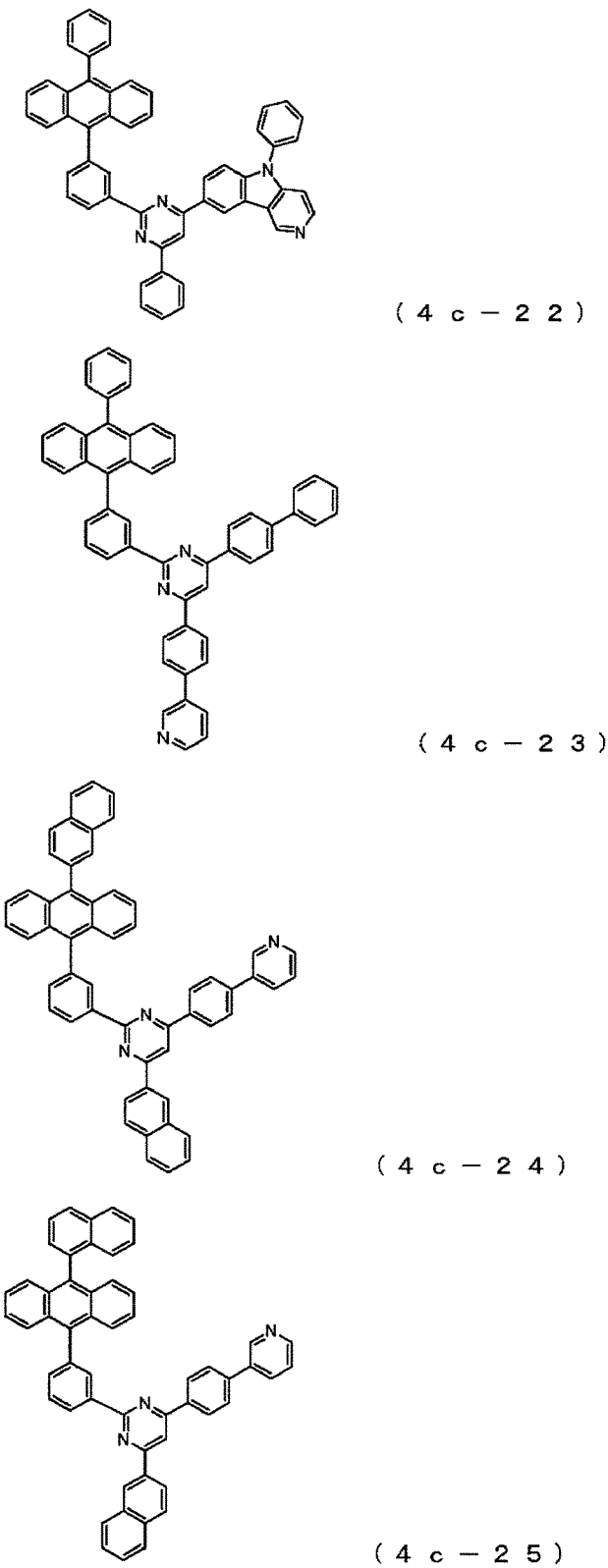
FIG. 40 is a diagram showing the structural formulas of Compound Nos. (4c-22) to (4c-25) that are anthracene derivatives of general formula (4c).
Figure 41:
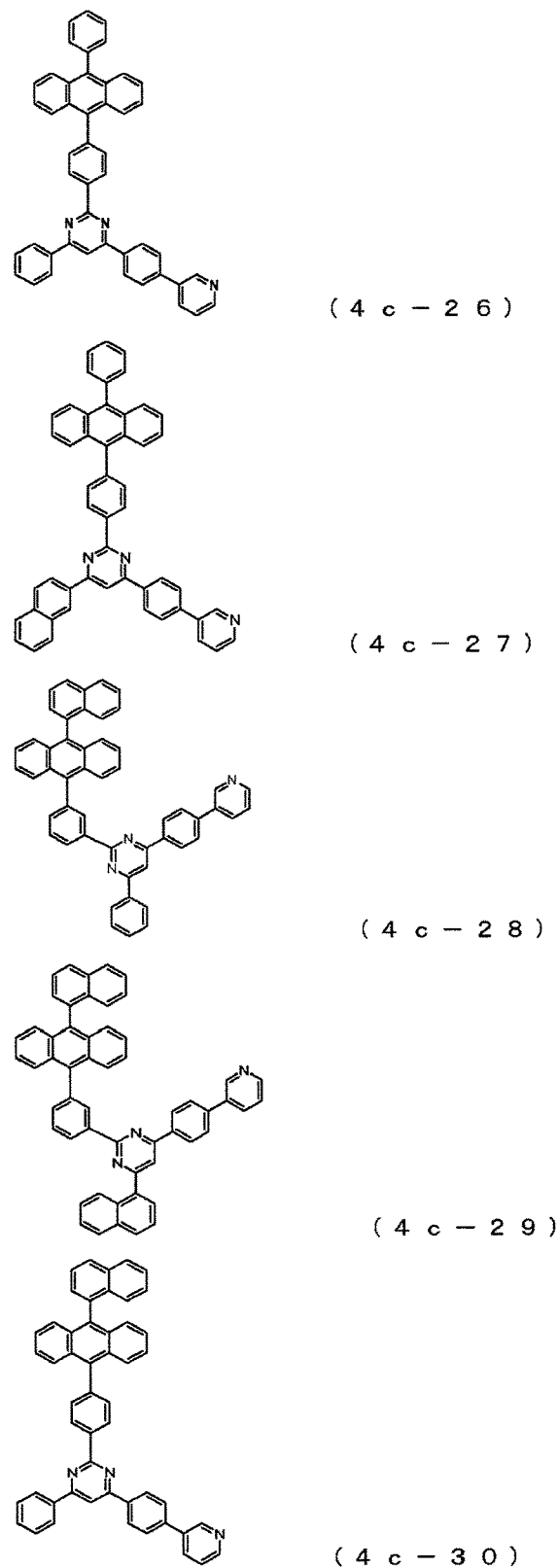
FIG. 41 is a diagram showing the structural formulas of Compound Nos. (4c-26) to (4c-30) that are anthracene derivatives of general formula (4c).
Figure 42:
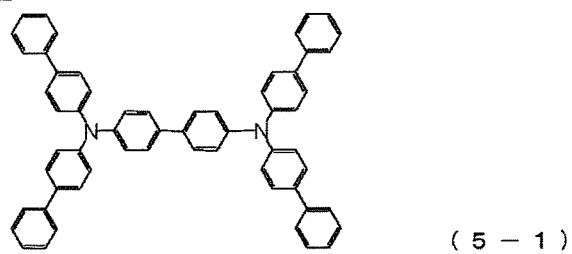
FIG. 42 is a diagram showing the structural formulas of Compound Nos. (5-1) to (5-5) that are triarylamine derivatives of general formula (5).
Figure 42:
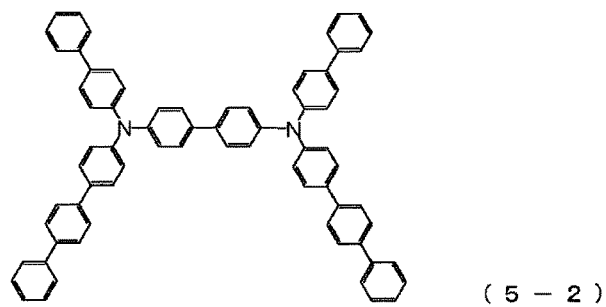
Figure 42:
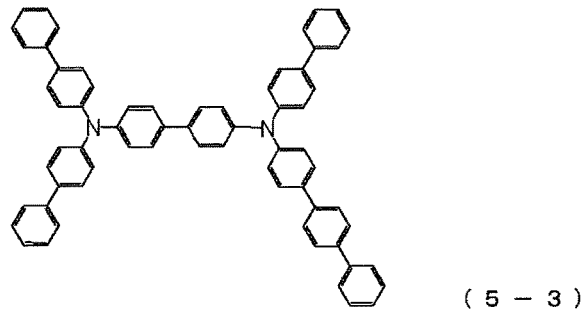
Figure 42:
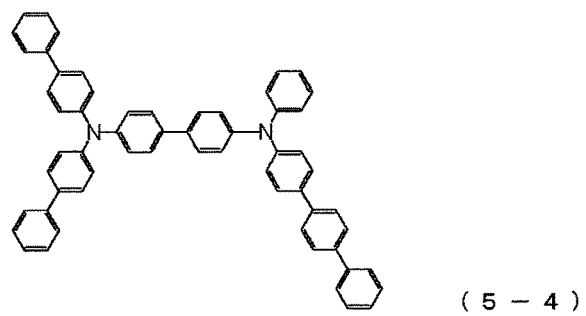
Figure 42:
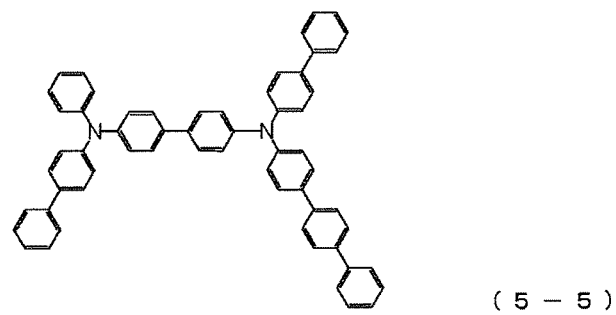
Figure 43:
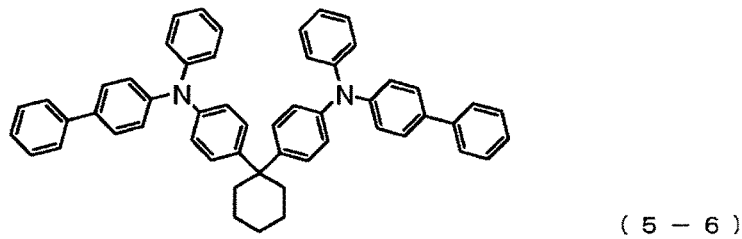
FIG. 43 is a diagram showing the structural formulas of Compound Nos. (5-6) to (5-10) that are triarylamine derivatives of general formula (5).
Figure 43:
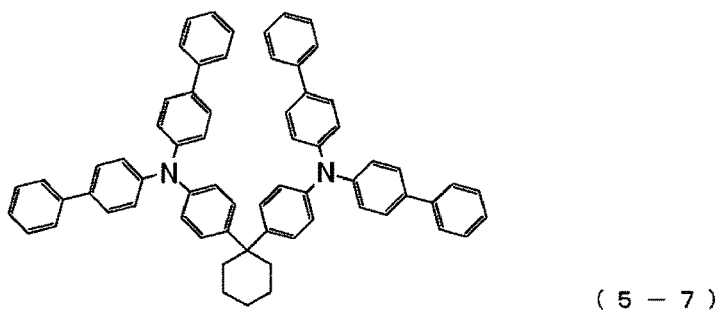
Figure 43:
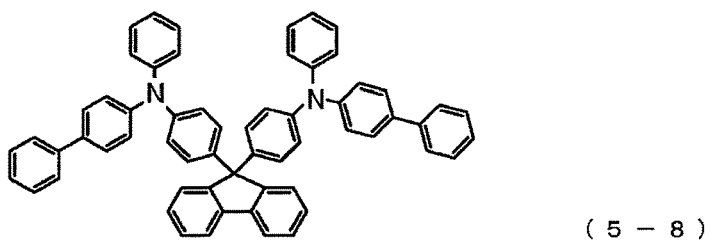
Figure 43:
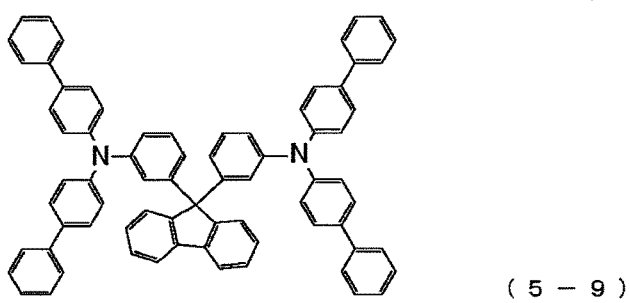
Figure 43:
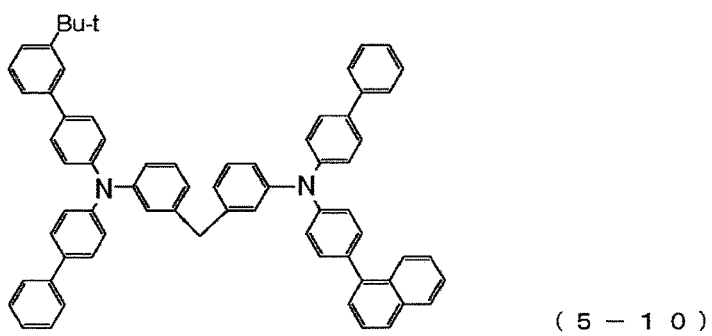
Figure 44:
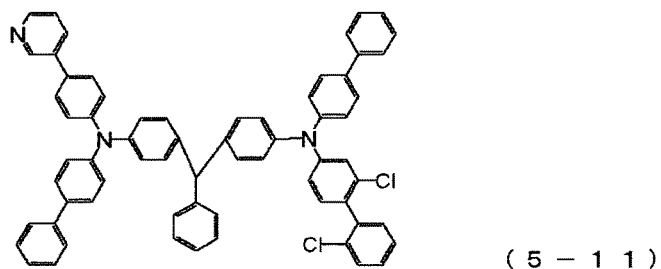
FIG. 44 is a diagram showing the structural formulas of Compound Nos. (5-11) to (5-15) that are triarylamine derivatives of general formula (5).
Figure 44:
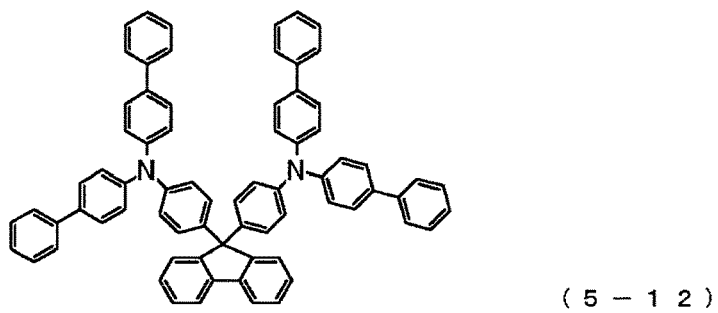
Figure 44:
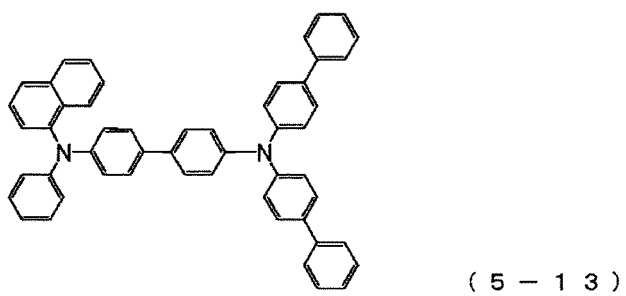
Figure 44:
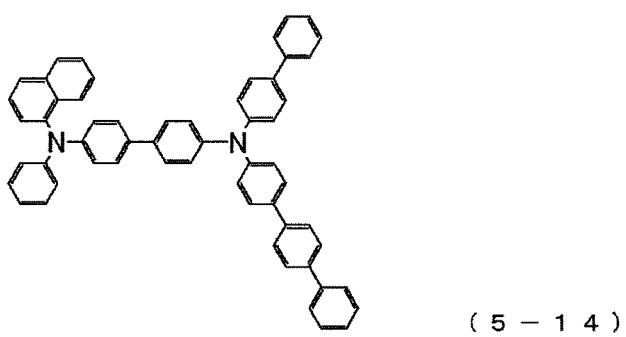
Figure 44:
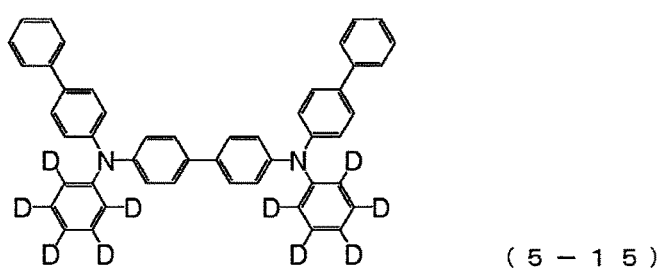
Figure 45:
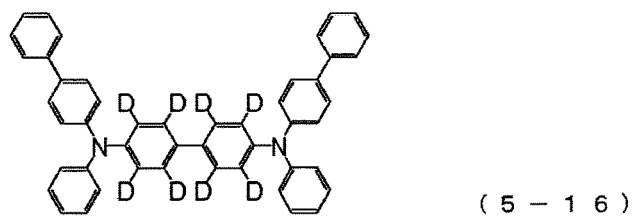
FIG. 45 is a diagram showing the structural formulas of Compound Nos. (5-16) to (5-20) that are triarylamine derivatives of general formula (5).
Figure 45:
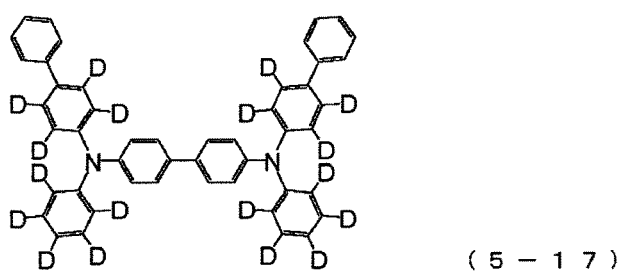
Figure 45:
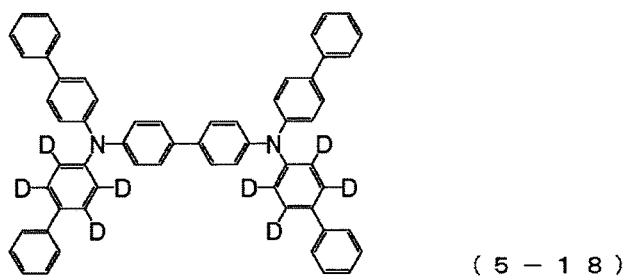
Figure 45:
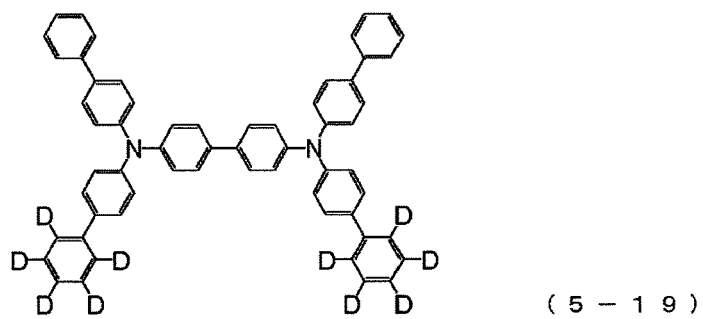
Figure 45:
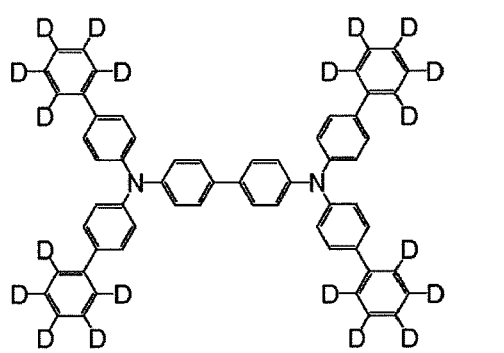
Figure 46:
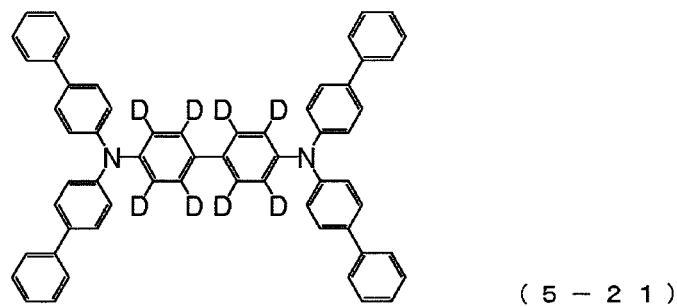
FIG. 46 is a diagram showing the structural formulas of Compound Nos. (5-21) to (5-23) that are triarylamine derivatives of general formula (5).
Figure 46:
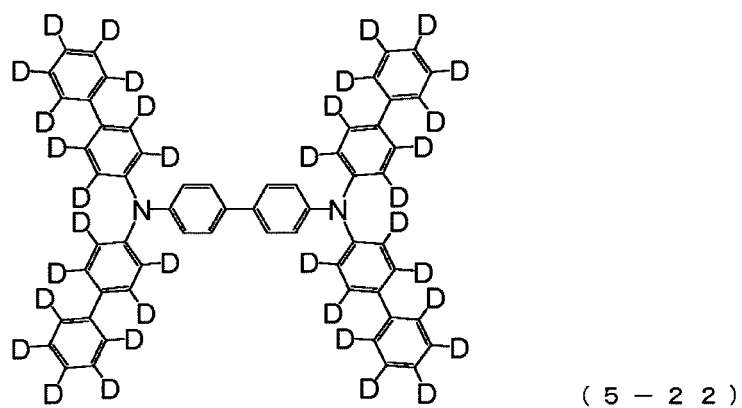
Figure 46:
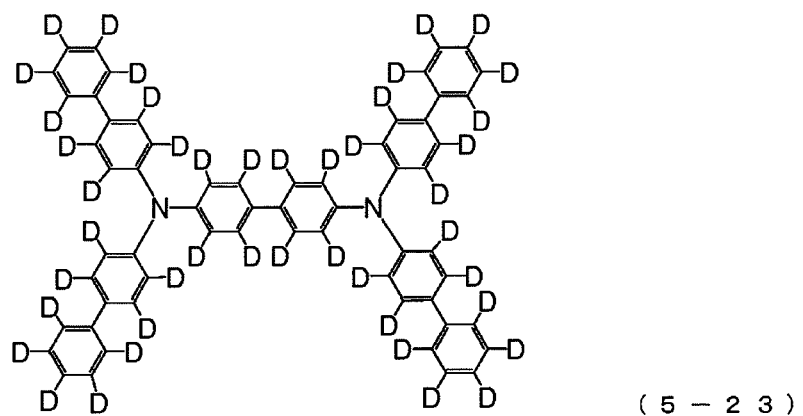

Specific examples of anthracene derivatives represented by the general formula (4b) above include Compounds (4b-1) to (4b-16) having the structural formulas shown in FIGS. 32 to 34.

Anthracene derivatives represented by the general formula (4c);

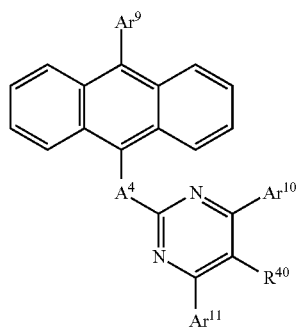

(4c)

In the general formula (4c), $A^4$ is, as in the formula (4), a divalent aromatic hydrocarbon group, a divalent aromatic heterocyclic group or a single bond.

Also, the nitrogen-containing heterocycle to which $A^4$ is bonded corresponds to group E in the general formula (4).

In addition, $Ar^9$ in the general formula (4c) above corresponds to C in the general formula (4) (i.e., q=1), and $Ar^{10}$, $Ar^{11}$ and $R^{40}$ are substituents bonded to the nitrogen-containing aromatic ring.

$Ar^9$ to $Ar^{11}$ represent a monovalent aromatic hydrocarbon group or a monovalent aromatic heterocyclic group. These groups are exemplified by, as with $Ar^6$ to $Ar^8$ above, the same groups exemplified for $R^1$ to $R^{10}$ in the general formula (1). Moreover, these monovalent aromatic hydrocarbon groups and monovalent aromatic heterocyclic groups, as with the $Ar^6$ to $Ar^8$ above, may have substituents.

Also, the $R^{40}$ bonded to the above nitrogen-containing heterocycle, as with $R^{33}$ to $R^{39}$ in the general formula (4a) above, is a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group or an aryloxy group.

These groups represented by $R^{40}$ may each have the same substituents as the groups represented by $R^1$ to $R^{10}$ in the general formula (1). When a plurality of these substituents are present, it is preferable for the plurality of substituents to be present independently, although a plurality of substituents may be bonded to each other via a single bond, a methylene group which may have a substituent, an oxygen atom or a sulfur atom to form a ring.

Specific examples of anthracene derivatives represented by the general formula (4c) above include Compounds (4c-1) to (4c-30) having the structural formulas shown in FIGS. 35 to 41.

In this invention, it is desirable for the electron transport layer to be formed by the above anthracene derivative. The various anthracene derivatives mentioned above as examples can be synthesized by methods that are known in themselves (see, for example, WO 2011/0593000, WO 2003/060956, and South Korean Patent Application Laid-open No. 2013-060956).

These anthracene derivatives may each be used independently, or a plurality of them may be mixed and used to form the electron transport layer to form the electron transport layer.

<Electron Injection Layer 8>

Electron Injection Layer;

An electron injection layer 8 is suitably provided between the cathode 9 and the electron transport layer 7. This electron injection layer 8 may be formed using, for example, an alkali metal salt such as lithium fluoride or cesium fluoride, an alkaline earth metal salt such as magnesium fluoride, or a metal oxide such as aluminum oxide.

<Cathode 9>

In the cathode 9 of the organic EL device of the invention, a metal having a low work function such as aluminum, or an alloy having a lower work function, such as a magnesium-silver alloy, a magnesium-indium alloy or an aluminum-magnesium alloy, may be used as the electrode material.

<Other Layers>

Where necessary, the organic EL device of the invention may have other layers. For example, although not shown in FIG. 1, an electron-blocking layer may be provided between the hole transport layer 5 and the luminous layer 6, and a hole-blocking layer may be provided between the luminous layer 6 and the electron transport layer 7.

The suitably provided layers may be formed of materials that are known in themselves, and are all formed by known methods, such as vapor deposition, spin coating or ink-jet printing, according to the type of material used.

Electron-Blocking Layer;

The electron-blocking layer, although not shown in FIG. 1, is provided between the hole transport layer 5 and the luminous layer 6. It is formed so as to block the passage of electrons from the luminous layer 6 and thereby increase the luminous efficiency. Various compounds having electron-blocking properties can be used as the material to form the electron-blocking layer. Typical examples include the following carbazole derivatives 4,4',4''-tri(N-carbazolyl)triphenylamine (TCTA); 9,9-bis[4-(carbazol-9-yl)phenyl]fluorene; 1,3-bis(carbazol-9-yl)benzene (mCP); and 2,2,-bis(4-carbazol-9-ylphenyl)adamantane (Ad-Cz).

Aside from the above carbazole derivatives, compounds such as 9-[4-(carbazol-9-yl)phenyl]-9-[4-(triphenylsilyl) phenyl]-9H-fluorene which have a triphenylsilyl group and also have on the molecule a triarylamine skeleton can also be used as the material to form the electron-blocking layer.

Hole-Blocking Layer;

The hole-blocking layer, although not shown in FIG. 1, is suitably provided between the electron transport layer 7 and the luminous layer 6. It is formed so as to block the passage of holes from the luminous layer 6 and thereby increase the luminous efficiency. Compounds having a hole-blocking effect, including phenanthroline derivatives such as bathocuproine (BCP), metal complexes of quinolinol derivatives such as aluminum(III) bis(2-methyl-8-quinolinate)-4-phenylphenolate (BAlq), and also various types of rare earth complexes, triazole derivatives, triazine derivatives and oxadiazole derivatives, may be used as the material to form the hole-blocking layer.

Each layer making up the organic EL device of the invention may have a single-layer structure formed of the various above-described materials or may have a multilayer structure obtained by the suitable combination of different materials.

In particular, in this invention, to show the excellent properties of the indenoacridan derivative of the general formula (1) above, it is preferable for the hole transport layer 5 to be given a two-layer structure including a first hole transport layer 5a and a second hole transport layer 5b, as shown in FIG. 1.

A hole transport layer 5 having this two-layer structure is described below.

<Hole Transport Layer 5 with Two-Layer Structure>

In the organic EL device of the invention, an indenoacridan derivative of the general formula (1) is used to form the hole transport layer 5. This indenoacridan derivative-containing hole transport layer 5 preferably has a two-layer structure.

That is, as shown in FIG. 1, it is preferable for the hole transport layer 5 to be given a two-layer structure divided into a first hole transport layer 5a positioned on the anode 2 side and a second hole transport layer 5b positioned on the luminous layer 6 side, and for the indenoacridan derivative of the general formula (1) above to be included in the second hole transport layer 5b. In such a case, a hole-transporting material differing from the indenoacridan derivative used in the second hole transport layer 5b is used to form the first hole transport layer 5a.

When the hole transport layer 5 is divided into two layers as mentioned above, the second hole transport layer 5b on the luminous layer 6 side, along with having hole-transporting properties, also exhibits very high electron-blocking properties. This is because the indenoacridan derivative of the above general formula (1), in addition to exhibiting hole transporting properties, also exhibits high electron-blocking properties. Therefore, by placing the second hole transport layer 5b adjacent to the luminous layer 6 as shown in FIG. 1, a higher carrier balance in the luminous layer 6 can be ensured, which is very advantageous for improving the characteristics of the organic EL device.

In such a two-layer structure, the second hole transport layer 5b is formed of an indenoacridan derivative represented by the general formula (1), but the first hole transport layer 5a is formed of a hole-transporting material that differs from the indenoacridan derivative used to form the second hole transport layer 5b.

As long as this hole-transporting material differs from that used to form the second hole transport layer 5b, this hole-transporting material may be an indenoacridan derivative represented by the general formula (1). However, it is generally preferable for the second hole transport layer 5b to be formed by using tryarylamine derivatives. This is because, although triarylamine derivatives are inferior to the above indenoacridan derivatives in terms of their electron-blocking properties, they have a performance equal to or better than that of indenoacridan derivatives in terms of their hole-transporting properties. This is also because there is not much need for electron-blocking properties in the first hole transport layer 5a which is not in direct contact with the luminous layer 6.

Such triarylamine derivatives have a molecular structure in which two triarylamine skeletons are bonded via a single bond or a divalent hydrocarbon group. The triarylamine derivative has two to six triarylamine skeletons in the molecule.

In this invention, from the standpoint of good thin-film stability and heat resistance and ease of synthesis as well as hole transporting properties, it is preferable to form the first hole transport layer 5a using a triarylamine derivative represented by the following general formula (5) or (6). Such triarylamine derivatives may be used alone, or two or more types may be mixed and used.

Triarylamine derivatives represented by a general formula (5);

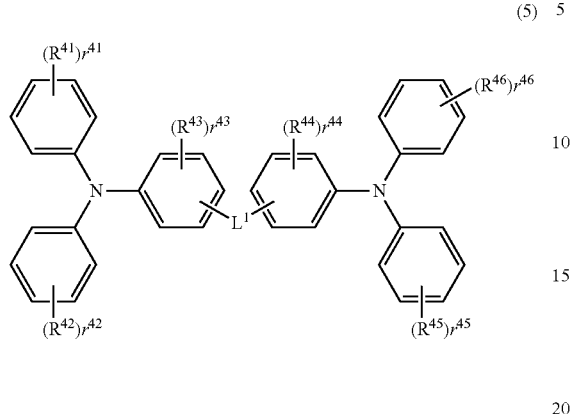

(5)

Triarylamine derivatives represented by this general formula (5) have two triarylamine skeletons.

In the general formula (5), $r^{41}$ to $r^{46}$ are integers indicating the number of, respectively, substituents $R^{41}$ to $R^{46}$ bonded to the aromatic ring. $r^{41}$, $r^{42}$, $r^{45}$ and $r^{46}$ each represent an integer of 0 to 5. $r^{43}$ and $r^{44}$ each represent an integer of 0 to 4.

The substituents $R^{41}$ to $R^{46}$ bonded to the aromatic ring each represent a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, an aralkyl group or an aryloxy group.

When a plurality of these substituents are present on the same benzene ring, it is preferable for the plurality of substituents that are present to be independently present, although such substituents may be bonded to each other via a single bond, a methylene group which may have a substituent, an oxygen atom or a sulfur atom to form a ring. For example, a plurality of substituents may be bonded to form a naphthalene ring.

Specific examples of the alkyl groups, cycloalkyl groups, alkenyl groups, alkyloxy groups, cycloalkyloxy groups, aralkyl groups or aryloxy groups represented by the above substituents $R^{41}$ to $R^{46}$ include the same groups as those exemplified for groups $R^{33}$ to $R^{39}$ in the general formula (4a). Specific examples of the monovalent aromatic hydrocarbon groups or monovalent aromatic heterocyclic groups include the same groups exemplified for groups $R^{1}$ to $R^{10}$ in the general formula (1).

The groups $R^{41}$ to $R^{46}$, as with the groups represented by $R^{33}$ to $R^{39}$ or $R^{1}$ to $R^{10}$, may additionally have substituents. It is preferable for these substituents to be independently present, but these substituents may be bonded to each other via a single bond, a methylene group which may have a substituent, an oxygen atom or a sulfur atom to form a ring.

In the general formula (5), $L^{1}$ is a bridge group which connects two arylamine skeletons, this being a single bond or a divalent group represented by the following structural formula (B), (C), (D), (E), (F) or (G).

(B)

Here, n1 is an integer of 1 to 4.

(C)

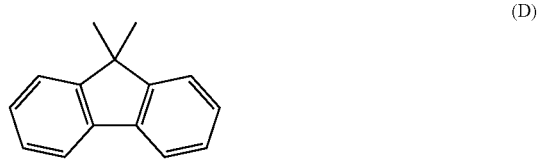

(D)

(E)

(F)

(G)

Specific examples of the triarylamine derivatives of the above general formula (5) include Compounds (5-1) to (5-23) having the structural formulas shown in FIGS. 42 to 46.

Figure 47:
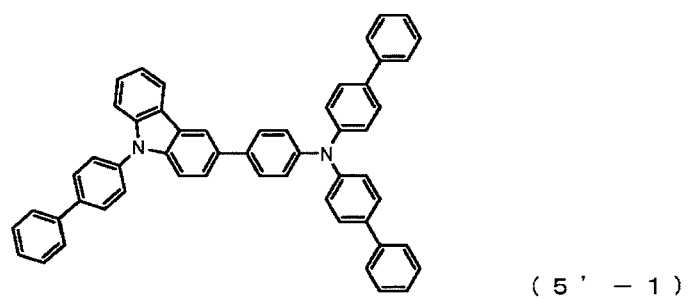
FIG. 47 is a diagram showing the structural formulas of Triarylamine Compound Nos. (5'-1) and (5'-2).
Figure 47:
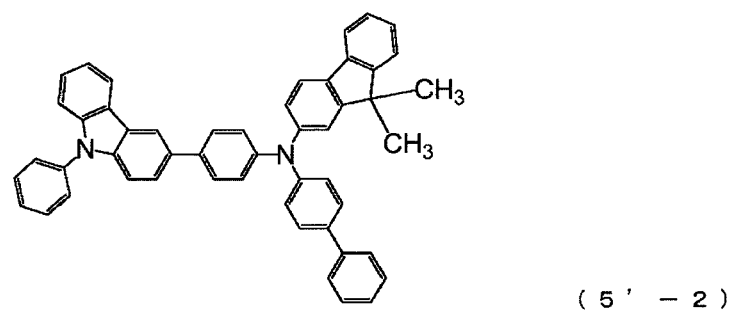
Figure 48:
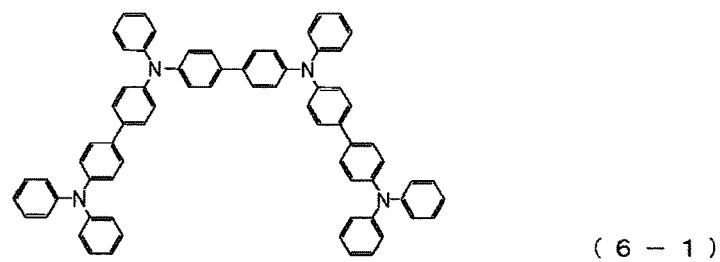
FIG. 48 is a diagram showing the structural formulas of Compound Nos. (6-1) to (6-5) that are triarylamine derivatives of general formula (6).
Figure 48:
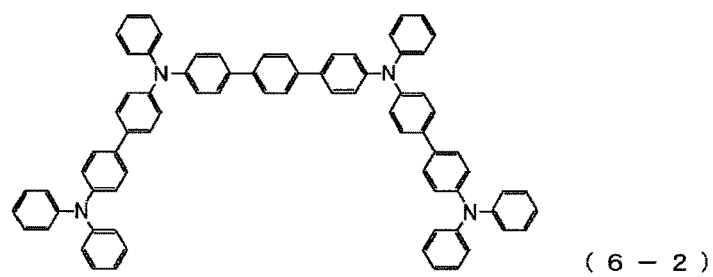
Figure 48:
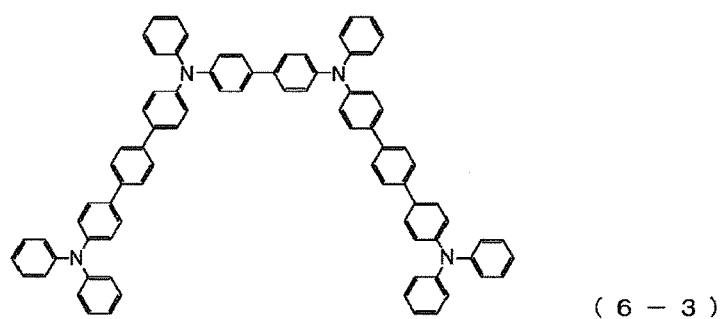
Figure 48:
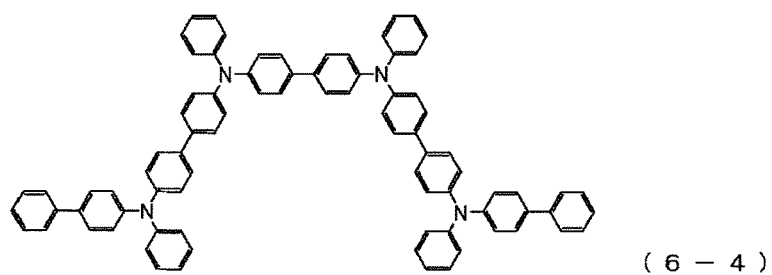
Figure 48:
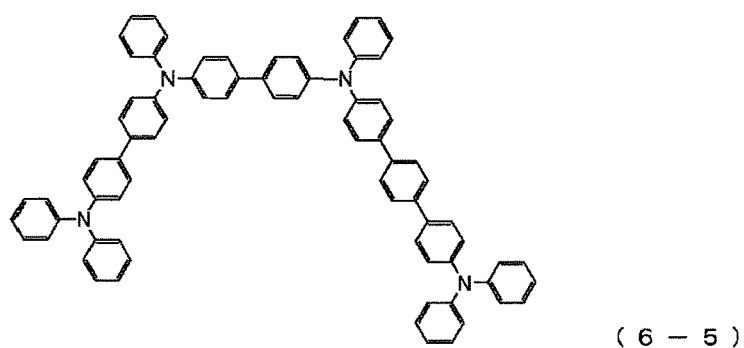
Figure 49:
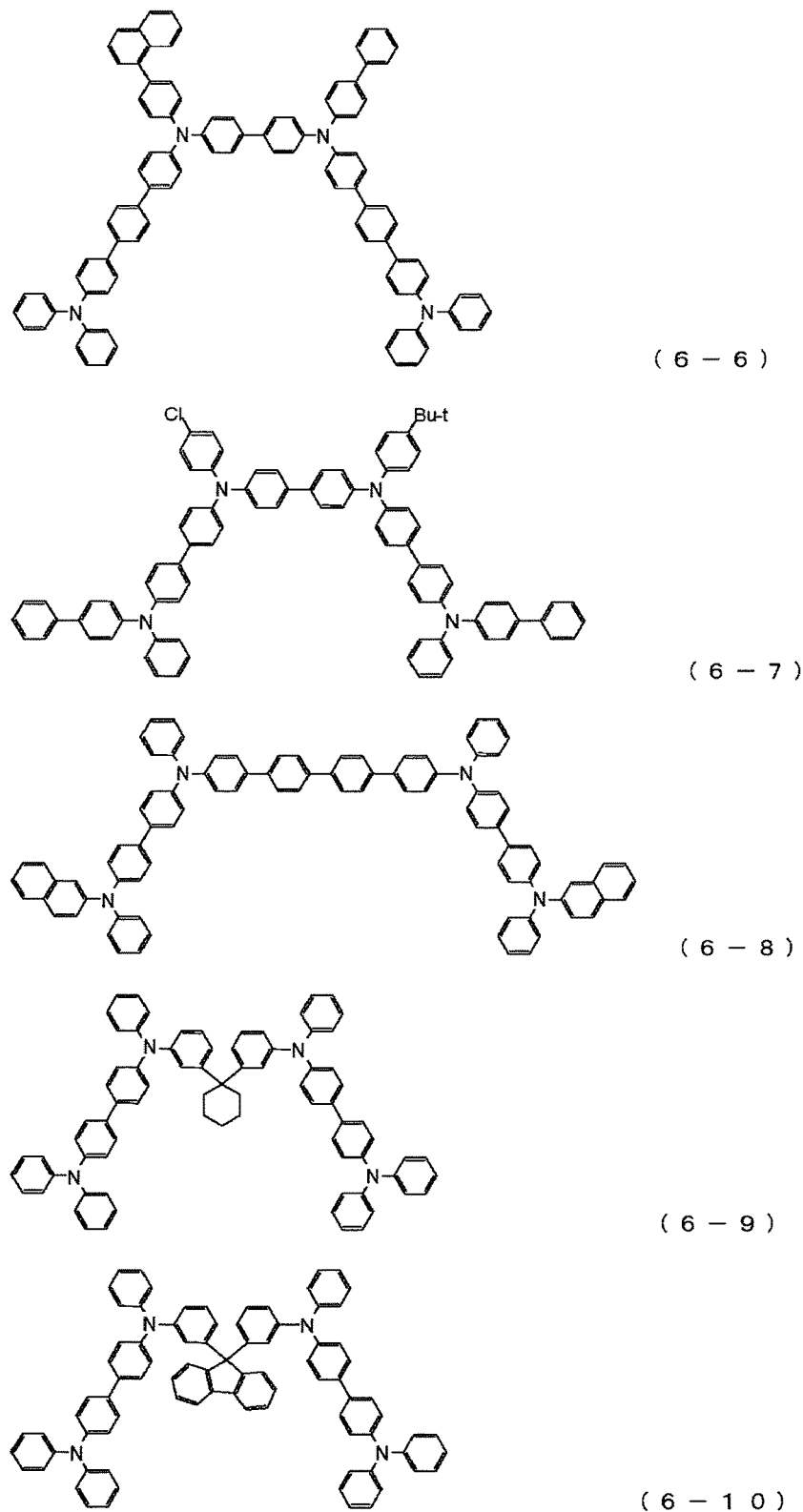
FIG. 49 is a diagram showing the structural formulas of Compound Nos. (6-6) to (6-10) that are triarylamine derivatives of general formula (6).
Figure 50:
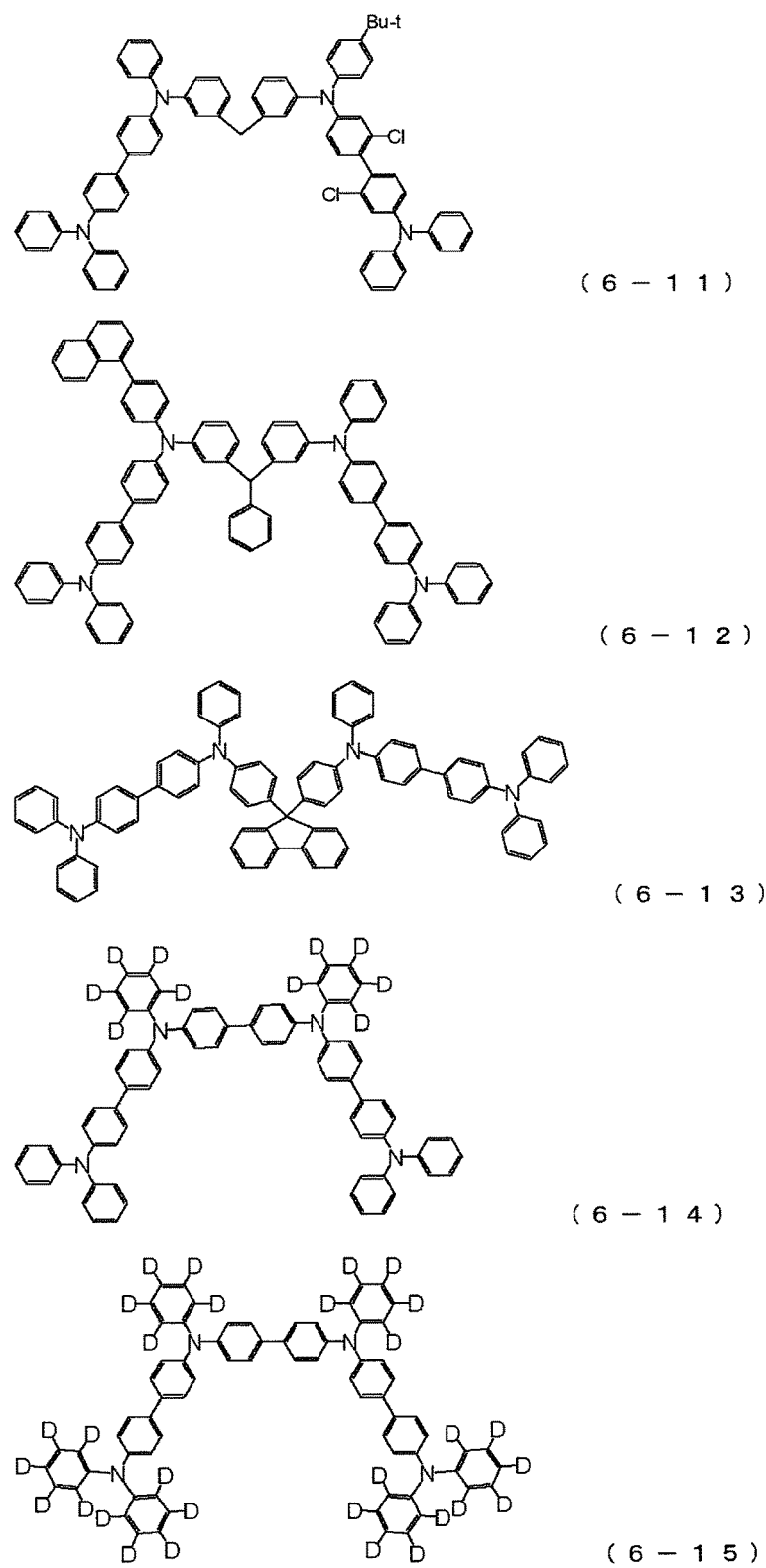
FIG. 50 is a diagram showing the structural formulas of Compound Nos. (6-11) to (6-15) that are triarylamine derivatives of general formula (6).
Figure 51:
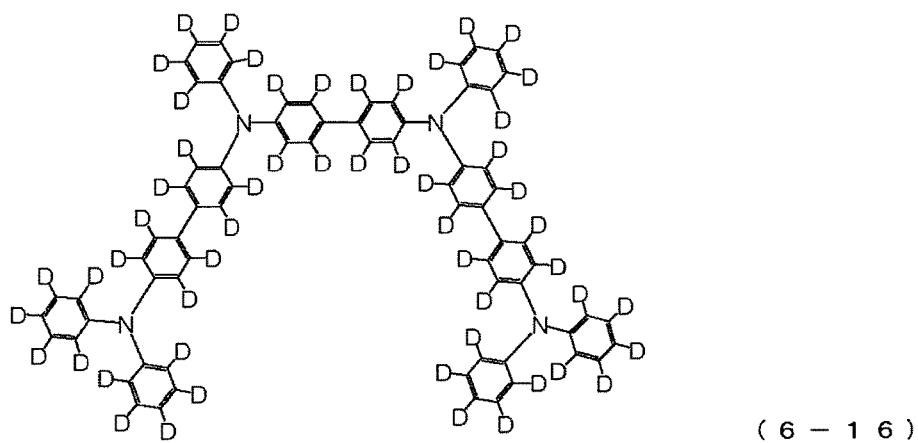
FIG. 51 is a diagram showing the structural formulas of Compound Nos. (6-16) and (6-17) that are triarylamine derivatives of general formula (6).
Figure 51:
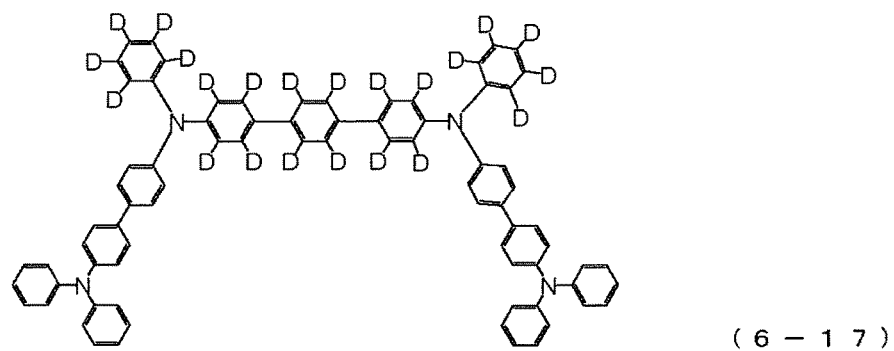

In this invention, aside from compounds represented by the general formula (5), Compounds (5'-1) and (5'-2) having the structural formulas shown in FIG. 47 can also be suitably used to form the first hole transport layer 5a. These compounds are ones in which, of the three phenyl groups bonded to the nitrogen atom on the amino group, two phenyl groups are bonded to each other via a single bond and thereby form a carbazole ring. It can be said that such compounds too have a molecular structure in which, essentially, two triarylamine skeletons are present and bonded each other via a single bond or a divalent hydrocarbon group, that is, they have substantially the same molecular structure as that of the triarylamine derivatives of the general formula (5).

Triarylamine derivatives represented by the general formula (6);

of formulas (C), (D), (E), (F) or (G) in the general formula (5).

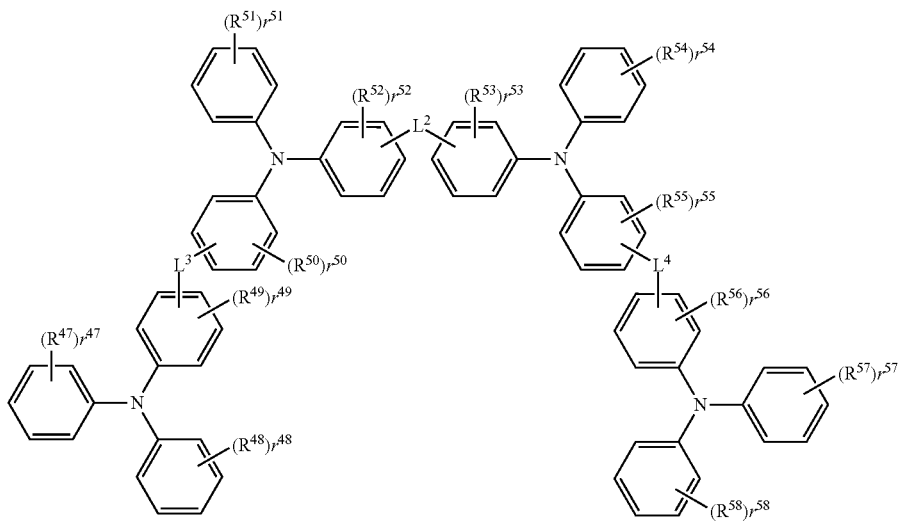

(6)

The triarylamine derivatives of this general formula (6) have four triarylamine skeletons.

In the general formula (6), $r^{47}$ to $r^{58}$ are integers indicating the number of, respectively, substituents $R^{47}$ to $R^{58}$ bonded to the aromatic ring. $r^{47}$, $r^{48}$, $r^{51}$, $r^{54}$, $r^{57}$ and $r^{58}$ each are an integer of 0 to 5.

Also, $r^{49}$, $r^{50}$, $r^{52}$, $r^{53}$, $r^{55}$ and $r^{56}$ each are an integer of 0 to 4.

The substituents $R^{47}$ to $R^{58}$ bonded to the aromatic ring are each a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, an aralkyl group or an aryloxy group.

When a plurality of these substituents are present on the same benzene ring, the plurality of substituents present are preferably independently present, although they may be bonded to each other via a single bond, a methylene group which may have a substituent, an oxygen atom or a sulfur atom to form a ring. For example, a plurality of substituents may be bonded together to form a naphthalene ring.

The above groups represented by substituents $R^{47}$ to $R^{58}$ can be exemplified by the same groups exemplified for groups $R^{41}$ to $R^{46}$ in the general formula (5). Moreover, as with these groups $R^{41}$ to $R^{46}$, they may have substituents. It is preferable for the substituents to be independently present, but they may be bonded to each other via a single bond, a methylene group which may have a substituent, an oxygen atom or a sulfur atom to form a ring.

In the general formula (6), $L^2$ to $L^4$ are bridge groups which connect two arylamine skeletons. They may be single bonds, divalent groups represented by the following structural formula (B'), or the same groups as the divalent groups

(B')

Here, n2 is an integer from 1 to 3.

The triarylamine derivatives of the general formula (6) above are exemplified by Compounds (6-1) to (6-17) having the structural formulas shown in FIGS. 48 to 51.

In this invention, the various triarylamine derivatives which are exemplified above can be synthesized by methods that are known in themselves (see, for example, Japanese Patent Application Laid-open No. H7-126615, Japanese Patent Application Laid-open No. H8-048656 and Japanese Patent Application Laid-open No. 2005-108804).

The thickness t1 of the first hole transport layer 5a formed using the above triarylamine derivative and the thickness t2 of the second hole transport layer 5b formed using an indenoacridan derivative of the general formula (1) have a total thickness (t1+t2) which is preferably in the range of 20 to 300 nm, more preferably in the range of 50 to 200 nm, and even more preferably in the range of 50 to 150 nm.

In the organic EL device of the invention having the above-described structure, because organic EL device materials having excellent hole and electron injecting and transporting abilities and excellent thin-film stability and durability are assembled while taking into consideration the carrier balance, compared with conventional organic EL devices, the hole-transporting efficiency from the hole transport layer to the luminous layer is improved, and the electron-transporting efficiency from the electron transport layer to the luminous layer is also improved. Moreover, when the hole transport layer is given a two-layer structure including a first hole transport layer and a second hole transport layer, the carrier balance is further improved, the luminous efficiency is further increased, and the driving voltage is further lowered, the durability of the organic EL device is improved.

Thus according to this invention, it is possible to achieve organic EL devices having a high efficiency, a low driving voltage and a long life.

EXAMPLES

This invention is illustrated by the following experimental examples.

Example 1

<Synthesis of Indenoacridan Compound 1-1>
Step 1;

| | |
|---|---|
| A nitrogen-purged reactor was charged with methyl 2-aminobenzoate | 35.4 g, |
| 2-iodo-9,9-dimethyl-9H-fluorene | 50.0 g, |
| tert-butoxysodium | 22.51 g and |
| xylene | 500 mL. |

Nitrogen gas was passed through the reactor for one hour. Next,

| | |
|---|---|
| tris(dibenzylideneacetone)dipalladium(0) | 2.9 g and |
| a toluene solution of tri-tert-butylphosphine (50%, w/v) | 3.8 g | were added, and the reactor contents were stirred for 5 hours at 115° C. The system was cooled to room temperature and water and toluene were added. Liquid separation was carried out and the organic layer was collected.

The organic layer was dried over anhydrous magnesium sulfate and then concentrated under reduced pressure, giving a crude product. The crude product was purified by column chromatography (carrier:silica gel, eluant:toluene/n-hexane), giving 25.8 g (yield, 48%) of methyl 2-{(9,9-dimethyl-9H-fluoren-2-yl)amino}benzoate as a yellow powder.

Step 2;

A large amount of methyl 2-{(9,9-dimethyl-9H-fluoren-2-yl)amino}benzoate yellow powder (abbreviated below as "methyl benzoate derivative") was synthesized as described above, and the following synthesis was carried out.

| | |
|---|---|
| A nitrogen-purged reactor was charged with the methyl benzoate derivative obtained above | 31.0 g and |
| THF | 310 mL. |

Then, 108 mL of a THF solution of methylmagnesium chloride (3 mol/L) was added dropwise thereto. After stirring for 1 hour at room temperature, 300 mL of an aqueous solution of 20% ammonium chloride was added, extraction was carried out using toluene, and the organic layer was collected. The organic layer was dried over anhydrous magnesium sulfate and then concentrated under reduced pressure, giving 31.0 g (yield, 100%) of 2-[2-{(9,9-dimethyl-9H-fluoren-2-yl)amino}phenyl]propan-2-ol as a light-yellow oily matter.

Step 3;

| | |
|---|---|
| A nitrogen-purged reactor was charged with the light-yellow oily matter obtained above | 31.0 g and |
| phosphoric acid | 62 mL. |

Then, the reactor contents were stirred for 2 hours at room temperature. Next, 300 mL of toluene and 300 mL of water were added and stirred. The precipitate that formed was collected by filtration, giving 26.2 g (yield, 89%) of 7,7,13,13-tetramethyl-7,13-dihydro-5H-indeno[1,2-b]acridine as a light yellow powder.

Step 4;

| | |
|---|---|
| A nitrogen-purged reactor was charged with the acridine obtained in Step 3 as a light-yellow powder | 8.0 g, |
| 2-(4-bromophenyl)-9,9-dimethylfluorene | 9.4 g, |
| tert-butoxysodium | 4.6 g and |
| toluene | 100 mL. |

Then, nitrogen gas was passed through the reactor for 1 hour. Next,

| | |
|---|---|
| palladium(II) acetate | 0.2 g and |
| a toluene solution of tri-tert-butylphosphine (50%, w/v) | 0.2 g | were added, followed by heated and stirred for 15 hours at 100° C.

The system was then cooled to room temperature and 100 mL of water was added, then, an extraction operation using toluene was carried out and the organic layer was collected. The organic layer was dried over anhydrous magnesium sulfate and then concentrated under reduced pressure, giving a crude product. The crude product was purified by column chromatography (carrier:silica gel, eluant:toluene/n-hexane), giving as a white powder 6.4 g (yield, 43%) of Indenoacridan Compound 1-1 having the structural formula shown below.

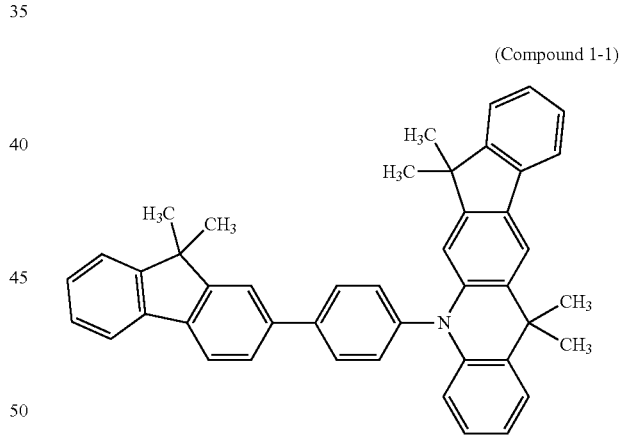

(Compound 1-1)

Figure 2:
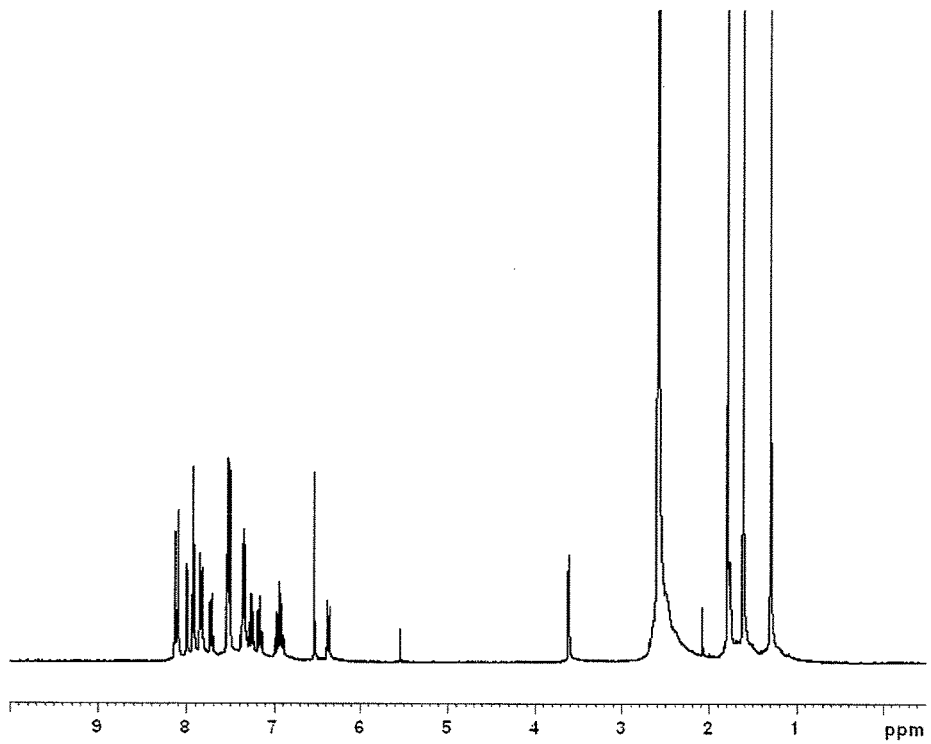
FIG. 2 is a ¹H-NMR chart of Compound (1-1) synthesized in Example 1.

The structure of the obtained white powder was identified using NMR. The NMR chart is shown in FIG. 2.

The following 39 hydrogen signals were detected in $^1$H-NMR (THF-$d_8$).

δ (ppm)=8.11 (2H)
8.00 (1H)
7.92 (2H)
7.83 (2H)
7.72 (1H)
7.48-7.58 (4H)
7.30-7.40 (3H)
7.27 (1H)
7.17 (1H)
6.89-7.00 (2H)
6.53 (1H)

6.38 (1H)
1.78 (6H)
1.58 (6H)
1.28 (6H)

Example 2

<Synthesis of Indenoacridan Compound 1-3>

The following synthesis was carried out using the 7,7,13,13-tetramethyl-7,13-dihydro-5H-indeno[1,2-b]acridine obtained in Step 3 of Example 1.

| A nitrogen-purged reactor was charged with the acridine | 9.0 g, |
| 2-(3-bromophenyl)-9,9-dimethylfluorene | 10.4 g, |
| tert-butoxysodium | 5.3 g and |
| toluene | 100 mL. |

Nitrogen gas was passed through the reactor for one hour. Next,

| palladium(II) acetate | 0.3 g and |
| a toluene solution of tri-tert-butylphosphine (50%, w/v) | 0.3 g | were added, followed by heated and stirred for 15 hours at 100° C.

The system was cooled to room temperature and 100 mL of water was added, then, an extraction operation was carried out using toluene, and the organic layer was collected. The organic layer was dried over anhydrous magnesium sulfate and then concentrated under reduced pressure, giving a crude product. The crude product was purified by column chromatography (carrier:silica gel, eluant:toluene/n-hexane), giving as a white powder 7.0 g (yield, 43%) of Indenoacridan Compound 1-3 having the structural formula shown below.

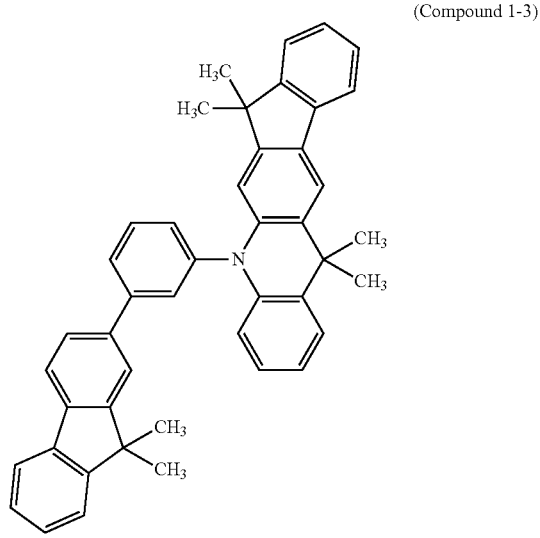 [SMILES: CC1(C)c2ccccc2-c2ccc(-c3cccc(N4c5ccccc5C(C)(C)c5cc6c(cc54)C(C)(C)c4ccccc4-6)c3)cc21]

(Compound 1-3)

Figure 3:
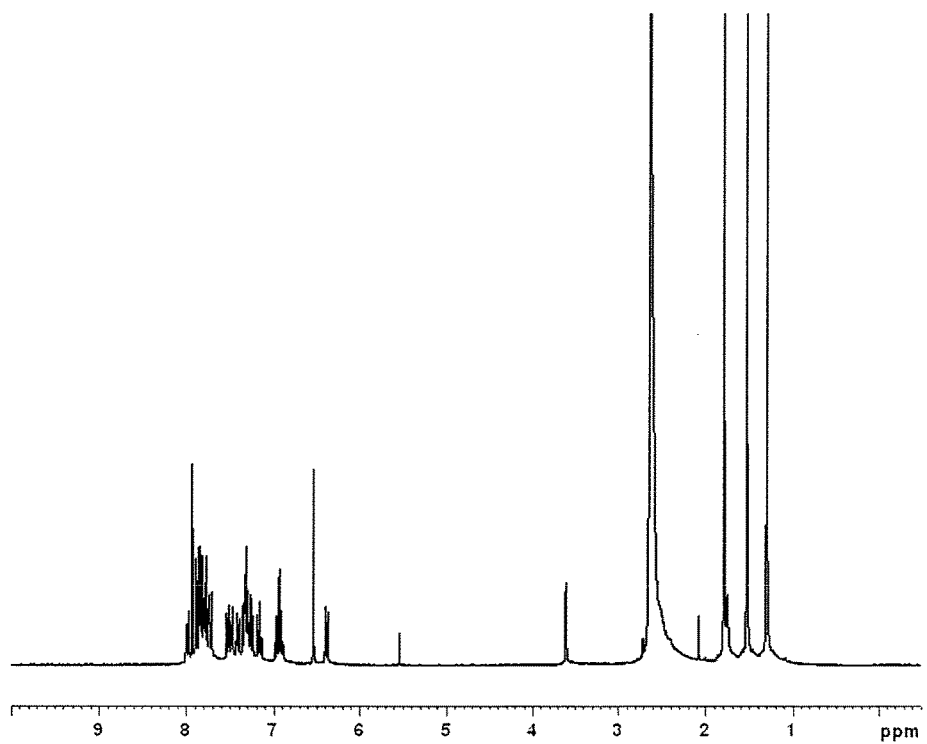
FIG. 3 is a ¹H-NMR chart of Compound (1-3) synthesized in Example 2.

The structure of the obtained white powder was identified using NMR. The NMR chart is shown in FIG. 3.

The following 39 hydrogen signals were detected in $^1$H-NMR (THF-$d_8$).
δ (ppm)=7.99 (1H)
7.93 (1H)
7.70-7.90 (7H)
7.45-7.56 (2H)
7.41 (1H)
7.22-7.39 (4H)
7.16 (1H)
6.88-7.00 (2H)
6.53 (1H)
6.38 (1H)
1.78 (6H)
1.58 (6H)
1.28 (6H)

Example 3

<Synthesis of Indenoacridan Compound 1-4>

The following synthesis was carried out using the 7,7,13,13-tetramethyl-7,13-dihydro-5H-indeno[1,2-b]acridine obtained in Step 3 of Example 1.

| A nitrogen-purged reactor was charged with the acridine | 8.0 g, |
| tert-butoxysodium | 4.6 g and |
| toluene | 100 mL. |

Nitrogen gas was passed through the reactor for one hour. Next,

| palladium(II) acetate | 0.2 g and |
| a toluene solution of tri-tert-butylphosphine (50%, w/v) | 0.2 g | were added, followed by heated and stirred for 14 hours at 100° C.

The system was cooled to room temperature and 100 mL of water was added, then, an extraction operation was carried out using toluene, and the organic layer was collected. The organic layer was dried over anhydrous magnesium sulfate and then concentrated under reduced pressure, giving a crude product. The crude product was purified by column chromatography (carrier:silica gel, eluant:toluene/n-hexane), giving as a white powder 6.1 g (yield, 41%) of Indenoacridan Compound 1-4 having the structural formula shown below.

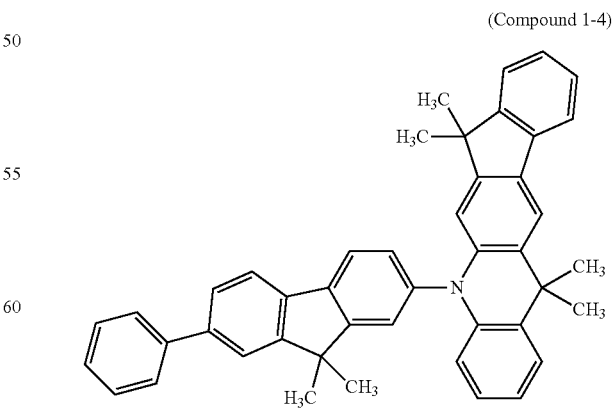

(Compound 1-4)

Figure 4:
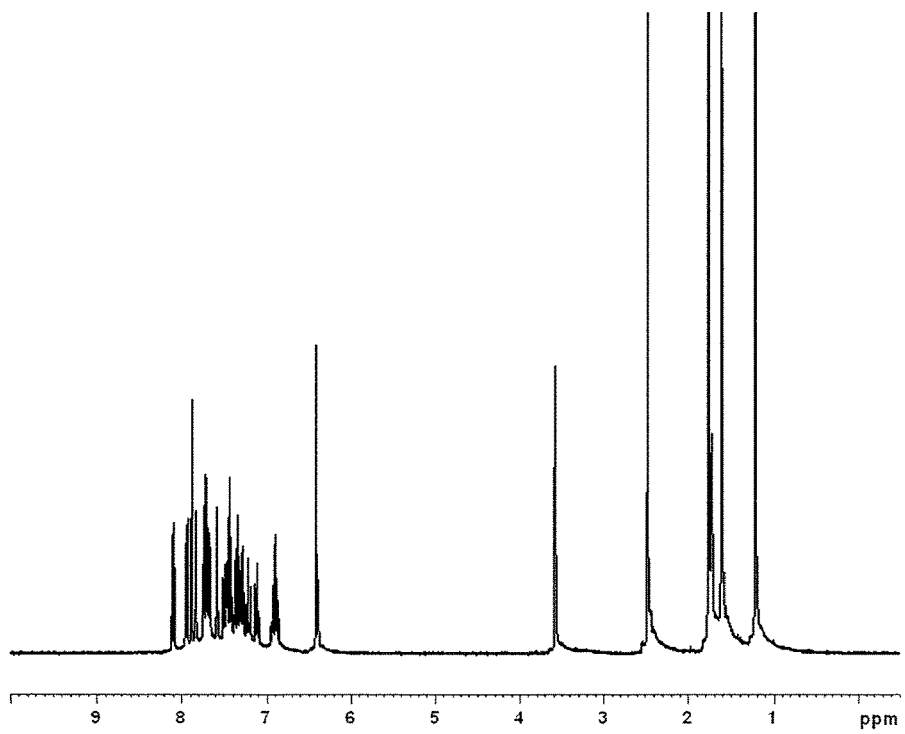
FIG. 4 is a ¹H-NMR chart of Compound (1-4) synthesized in Example 3.

The structure of the obtained white powder was identified using NMR. The NMR chart is shown in FIG. 4.

The following 39 hydrogen signals were detected in $^1$H-NMR (THF-$d_8$).
δ (ppm)=8.11 (1H)
7.95 (1H)
7.89 (1H)
7.83 (1H)
7.62-7.76 (4H)
7.58 (1H)
7.40-7.52 (3H)
7.28-7.40 (3H)
7.22 (1H)
7.12 (1H)
6.84-6.96 (2H)
6.38-6.43 (2H)
1.77 (6H)
1.61 (6H)
1.22 (6H)

Example 4

<Synthesis of Indenoacridan Compound 1-5>
The following synthesis was carried out using the 7,7,13,13-tetramethyl-7,13-dihydro-5H-indeno[1,2-b]acridine obtained in Step 3 of Example 1.

| | |
|---|---|
| A nitrogen-purged reactor was charged with the acridine | 8.0 g, |
| 2-bromo-7-(9,9-dimethylfluoren-2-yl)-9,9-dimethylfluorene | 11.5 g, |
| tert-butoxysodium | 3.5 g and |
| toluene | 100 mL. |

Nitrogen gas was passed through the reactor for one hour. Next,

| | |
|---|---|
| palladium(II) acetate | 0.3 g and |
| a toluene solution of tri-tert-butylphosphine (50%, w/v) | 0.2 g | were added, followed by heated and stirred for 15 hours at 100° C.

The system was cooled to room temperature and 100 mL of water was added, then, an extraction operation was carried out using toluene, and the organic layer was collected. The organic layer was dried over anhydrous magnesium sulfate and then concentrated under reduced pressure, giving a crude product. The crude product was purified by column chromatography (carrier:silica gel, eluant:toluene/n-hexane), giving as a white powder 5.2 g (yield, 29%) of Indenoacridan Compound 1-5 having the structural formula shown below.

Figure 5:
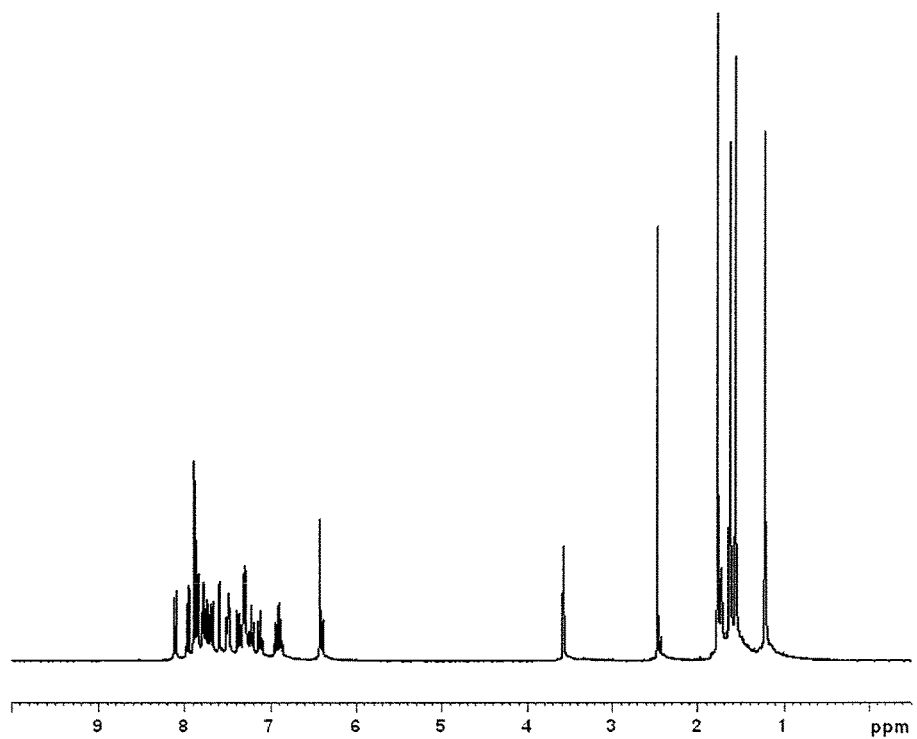
FIG. 5 is a ¹H-NMR chart of Compound (1-5) synthesized in Example 4.

The structure of the obtained white powder was identified using NMR. The NMR chart is shown in FIG. 5.
The following 47 hydrogen signals were detected in $^1$H-NMR (THF-$d_8$).
δ (ppm)=8.12 (1H)
7.97 (1H)
7.82-7.91 (4H)
7.65-7.82 (4H)
7.59 (1H)
7.45-7.55 (2H)
7.17-7.40 (5H)
7.12 (1H)
6.85-6.97 (2H)
6.39-6.46 (2H)
1.77 (6H)
1.63 (6H)
1.57 (6H)
1.22 (6H)

Example 5

<Synthesis of Indenoacridan Compound 1-6>
The following synthesis was carried out using the 7,7,13,13-tetramethyl-7,13-dihydro-5H-indeno[1,2-b]acridine obtained in Step 3 of Example 1.

| | |
|---|---|
| A nitrogen-purged reactor was charged with the acridine | 5.3 g, |
| 2-(4-bromophenyl-1-yl)-7-phenyl-9,9-dimethylfluorene | 7.0 g, |
| tert-butoxysodium | 3.1 g and |
| toluene | 100 mL. |

Nitrogen gas was passed through the reactor for one hour. Next,

| | |
|---|---|
| palladium(II) acetate | 0.2 g and |
| a toluene solution of tri-tert-butylphosphine (50%, w/v) | 0.2 g | were added, followed by heated and stirred for 14 hours at 100° C.

The system was cooled to room temperature and 100 mL of water was added, then, an extraction operation was carried out using toluene, and the organic layer was collected. The organic layer was dried over anhydrous magnesium sulfate and then concentrated under reduced pressure, giving a crude product. The crude product was purified by column chromatography (carrier:silica gel, eluant:toluene/n-hexane), giving as a white powder 6.5 g (yield, 59%) of Compound 1-6 having the structural formula shown below.

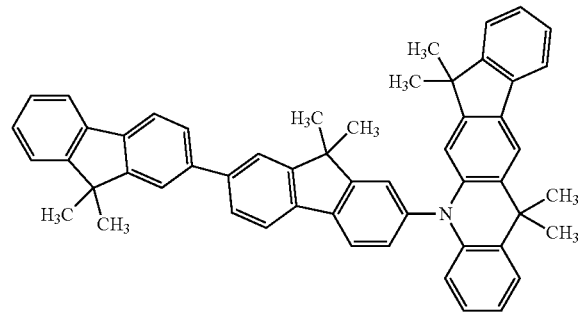

(Compound 1-5)

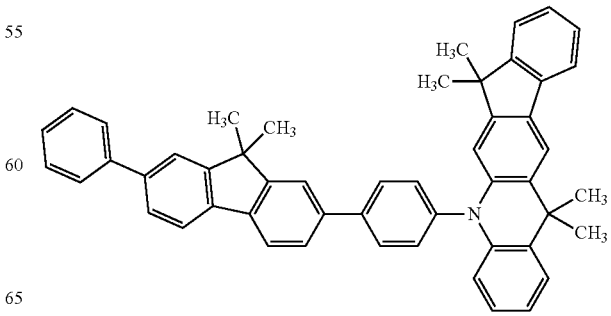

(Compound 1-6)

Figure 6:
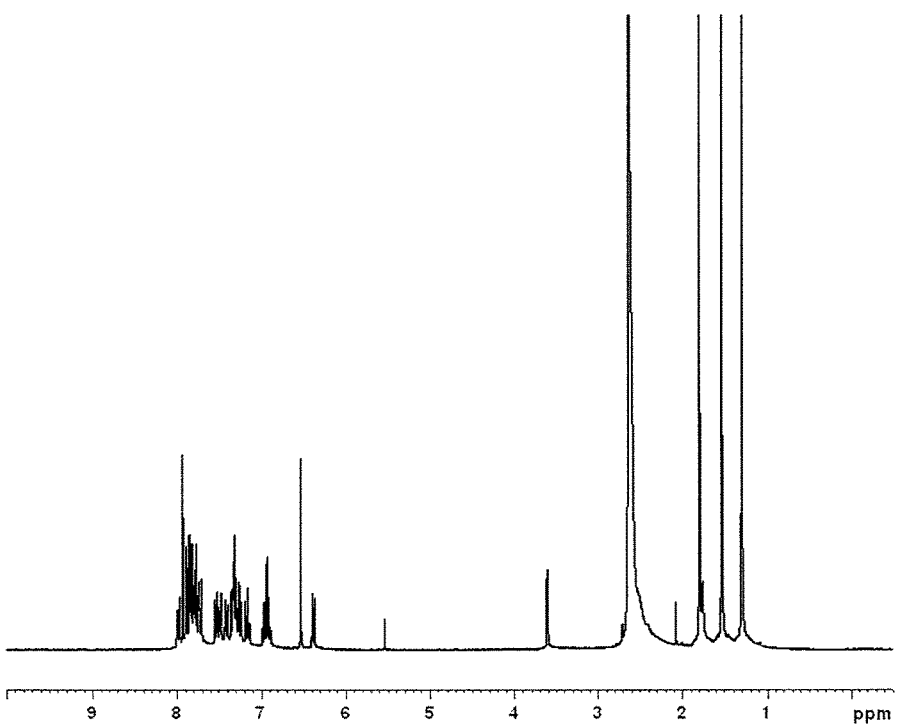
FIG. 6 is a ¹H-NMR chart of Compound (1-6) synthesized in Example 5.

The structure of the obtained white powder was identified using NMR. The NMR chart is shown in FIG. 6.

The following 43 hydrogen signals were detected in $^1$H-NMR (THF-$d_8$).

δ (ppm)=8.09 (2H)
7.99 (1H)
7.73-7.94 (5H)
7.60-7.73 (4H)
7.37-7.53 (5H)
7.28-7.37 (2H)
7.23 (1H)
7.13 (1H)
6.85-6.97 (2H)
6.51 (1H)
6.35 (1H)
1.76 (6H)
1.65 (6H)
1.27 (6H)

Example 6

<Synthesis of Indenoacridan Compound 1-7>

The following synthesis was carried out using the 7,7,13,13-tetramethyl-7,13-dihydro-5H-indeno[1,2-b]acridine obtained in Step 3 of Example 1.

| | |
|---|---|
| A nitrogen-purged reactor was charged with the acridine | 7.5 g, |
| 2-bromo-7-(naphthyl-1-yl)-9,9-dimethylfluorene | 10.1 g, |
| tert-butoxysodium | 4.4 g and |
| toluene | 100 mL. |

Nitrogen gas was passed through the reactor for one hour. Next,

| | |
|---|---|
| palladium(II) acetate | 0.2 g and |
| a toluene solution of tri-tert-butylphosphine (50%, w/v) | 0.2 g | were added, followed by heated and stirred for 14 hours at 100° C.

The system was cooled to room temperature and 100 mL of water was added, then, an extraction operation was carried out using toluene, and the organic layer was collected. The organic layer was dried over anhydrous magnesium sulfate and then concentrated under reduced pressure, giving a crude product. The crude product was purified by column chromatography (carrier:silica gel, eluant:toluene/n-hexane), giving as a white powder 6.7 g (yield, 45%) of Indenoacridan Compound 1-7 having the structural formula shown below.

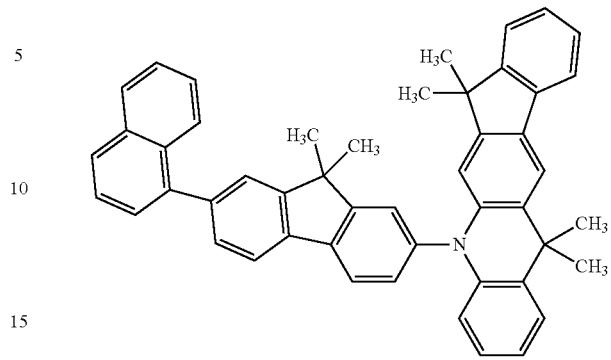

(Compound 1-7)

Figure 7:
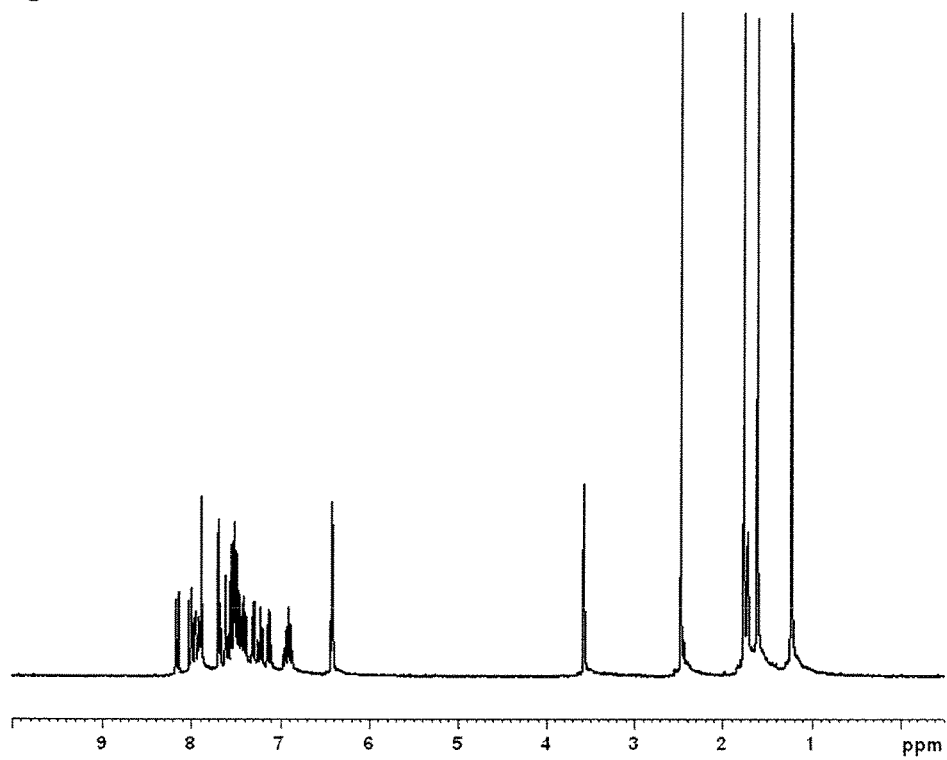
FIG. 7 is a ¹H-NMR chart of Compound (1-7) synthesized in Example 6.

The structure of the obtained white powder was identified using NMR. The NMR chart is shown in FIG. 7.

The following 41 hydrogen signals were detected in $^1$H-NMR (THF-$d_8$).

δ (ppm)=8.16 (1H)
7.85-8.05 (5H)
7.65-7.72 (2H)
7.35-7.64 (8H)
7.31 (1H)
7.23 (1H)
7.13 (1H)
6.85-6.98 (2H)
6.39-6.46 (2H)
1.77 (6H)
1.62 (6H)
1.24 (6H)

Example 7

<Synthesis of Indenoacridan Compound 1-8>

The following synthesis was carried out using the 7,7,13,13-tetramethyl-7,13-dihydro-5H-indeno[1,2-b]acridine obtained in Step 3 of Example 1.

| | |
|---|---|
| A nitrogen-purged reactor was charged with the acridine | 9.0 g, |
| 1-bromo-4-phenylnaphthalene | 9.4 g, |
| tert-butoxysodium | 5.2 g and |
| toluene | 100 mL. |

Nitrogen gas was passed through the reactor for one hour. Next,

| | |
|---|---|
| palladium(II) acetate | 0.3 g and |
| a toluene solution of tri-tert-butylphosphine (50%, w/v) | 0.3 g | were added, followed by heated and stirred for 16 hours at 100° C.

The system was cooled to room temperature and 100 mL of water was added, then, an extraction operation was carried out using toluene, and the organic layer was collected. The organic layer was dried over anhydrous magnesium sulfate and then concentrated under reduced pressure, giving a crude product. The crude product was purified by column chromatography (carrier:silica gel, eluant:toluene/n-hexane), giving as a white powder 4.3 g (yield, 29%) of Indenoacridan Compound 1-8 having the structural formula shown below.

(Compound 1-8)

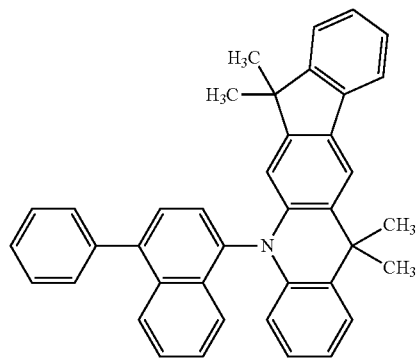

Figure 8:
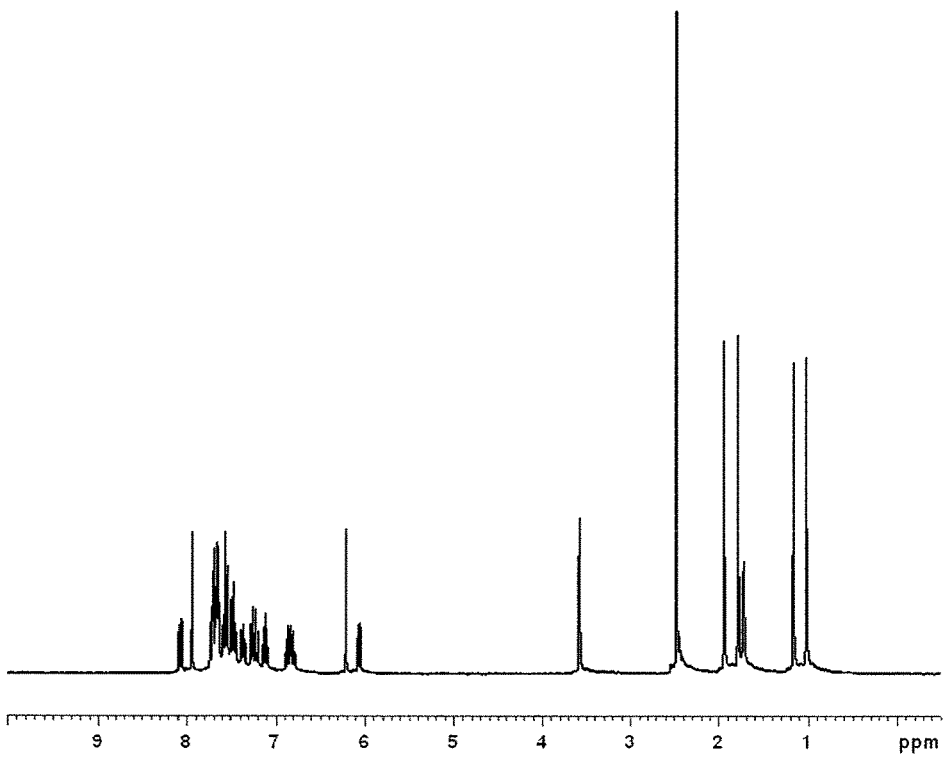
FIG. 8 is a ¹H-NMR chart of Compound (1-8) synthesized in Example 7.

The structure of the obtained white powder was identified using NMR. The NMR chart is shown in FIG. 8.
The following 33 hydrogen signals were detected in $^1$H-NMR (THF-$d_8$).
δ (ppm)=8.07 (1H)
7.95 (1H)
7.62-7.75 (6H)
7.52-7.60 (3H)
7.48 (2H)
7.36 (1H)
7.18-7.30 (2H)
7.11 (1H)
6.78-6.90 (2H)
6.22 (1H)
6.06 (1H)
1.94 (3H)
1.79 (3H)
1.17 (3H)
1.02 (3H)

Example 8

<Synthesis of Indenoacridan Compound 1-9>

The following synthesis was carried out using the 7,7,13,13-tetramethyl-7,13-dihydro-5H-indeno[1,2-b]acridine obtained in Step 3 of Example 1.

| A nitrogen-purged reactor was charged with the acridine | 9.5 g, |
|---|---|
| 1-bromo-4,1':2',1''-terphenyl | 9.9 g, |
| tert-butoxysodium | 5.6 g and |
| toluene | 100 mL. |

Nitrogen gas was passed through the reactor for one hour. Next,

| palladium(II) acetate | 0.3 g and |
|---|---|
| a toluene solution of tri-tert-butylphosphine (50%, w/v) | 0.3 g | were added, followed by heated and stirred for 16 hours at 100° C.
The system was cooled to room temperature and 100 mL of water was added, then, an extraction operation was carried out using toluene, and the organic layer was collected. The organic layer was dried over anhydrous magnesium sulfate and then concentrated under reduced pressure, giving a crude product. The crude product was purified by column chromatography (carrier:silica gel, eluant:toluene/n-hexane), giving as a white powder 4.2 g (yield, 27%) of Indenoacridan Compound 1-9 having the structural formula shown below.

(Compound 1-9)

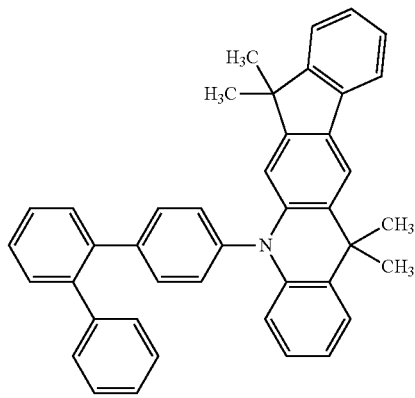

Figure 9:
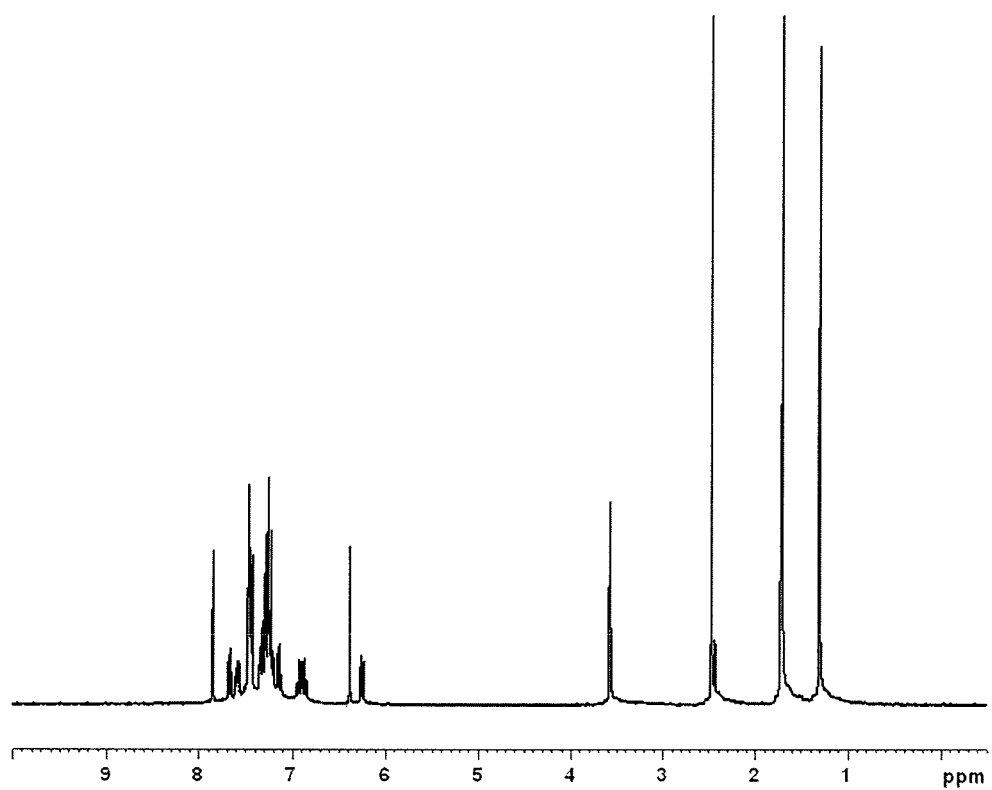
FIG. 9 is a ¹H-NMR chart of Compound (1-9) synthesized in Example 8.
Figure 10:
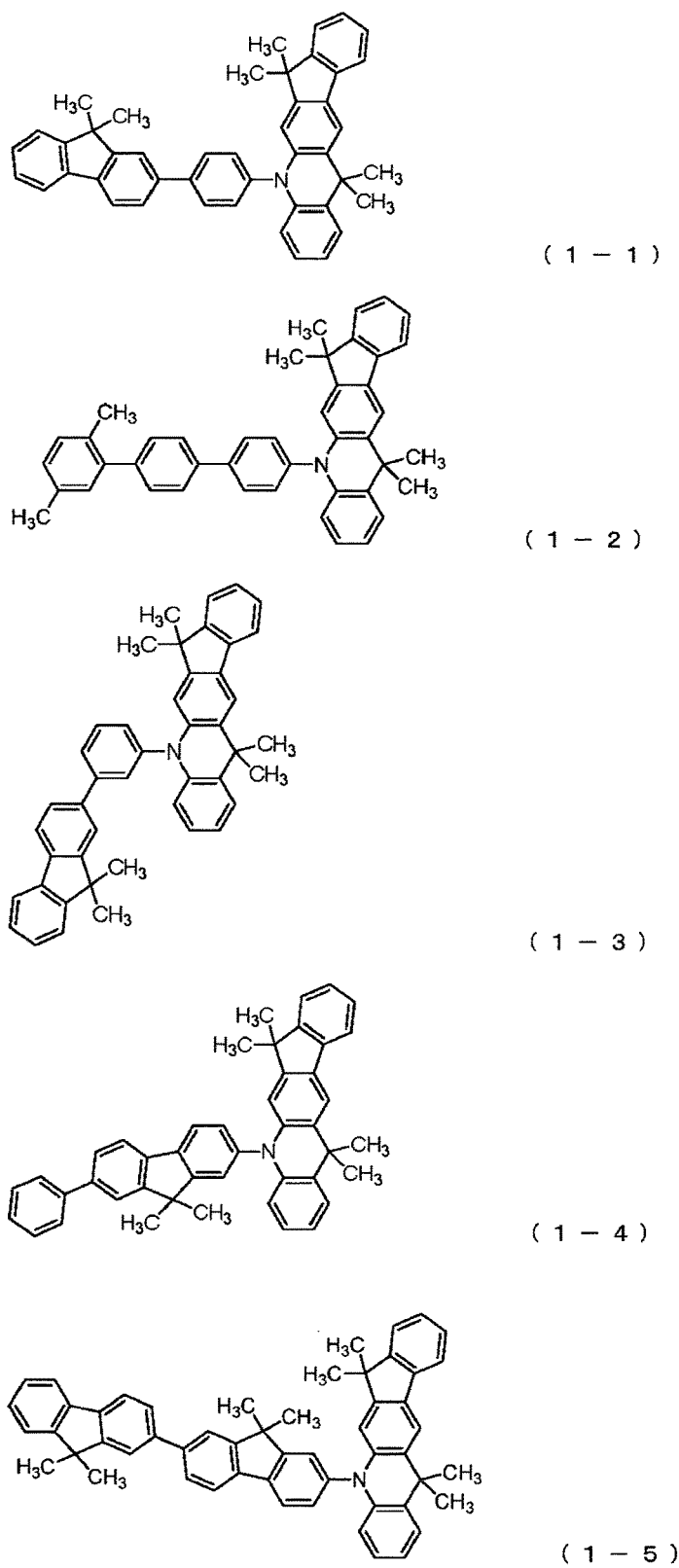
FIG. 10 is a diagram showing the structural formulas of Compound Nos. (1-1) to (1-5) that are indenoacridan derivatives of general formula (1).
Figure 11:
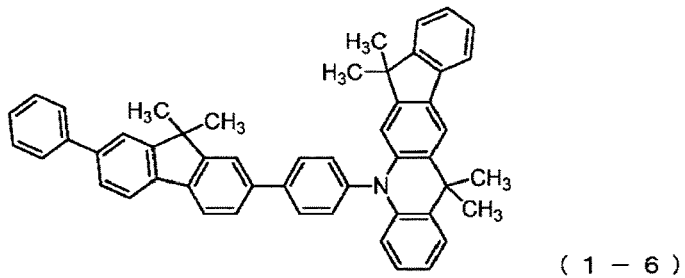
FIG. 11 is a diagram showing the structural formulas of Compound Nos. (1-6) to (1-10) that are indenoacridan derivatives of general formula (1).
Figure 11:
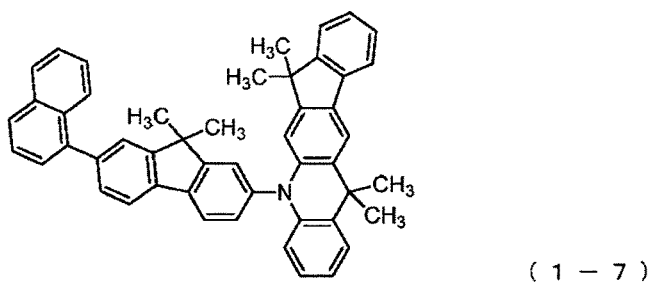
Figure 11:
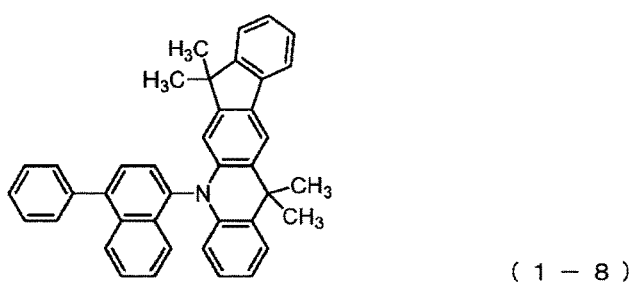
Figure 11:
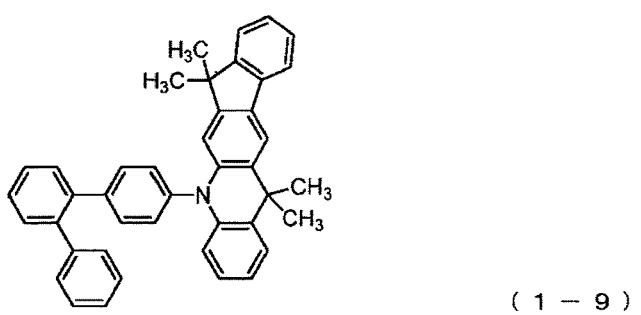
Figure 11:
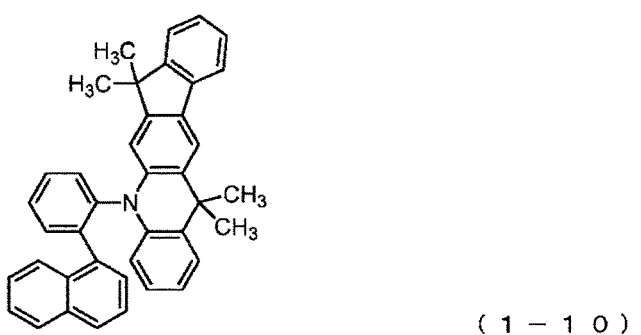
Figure 12:
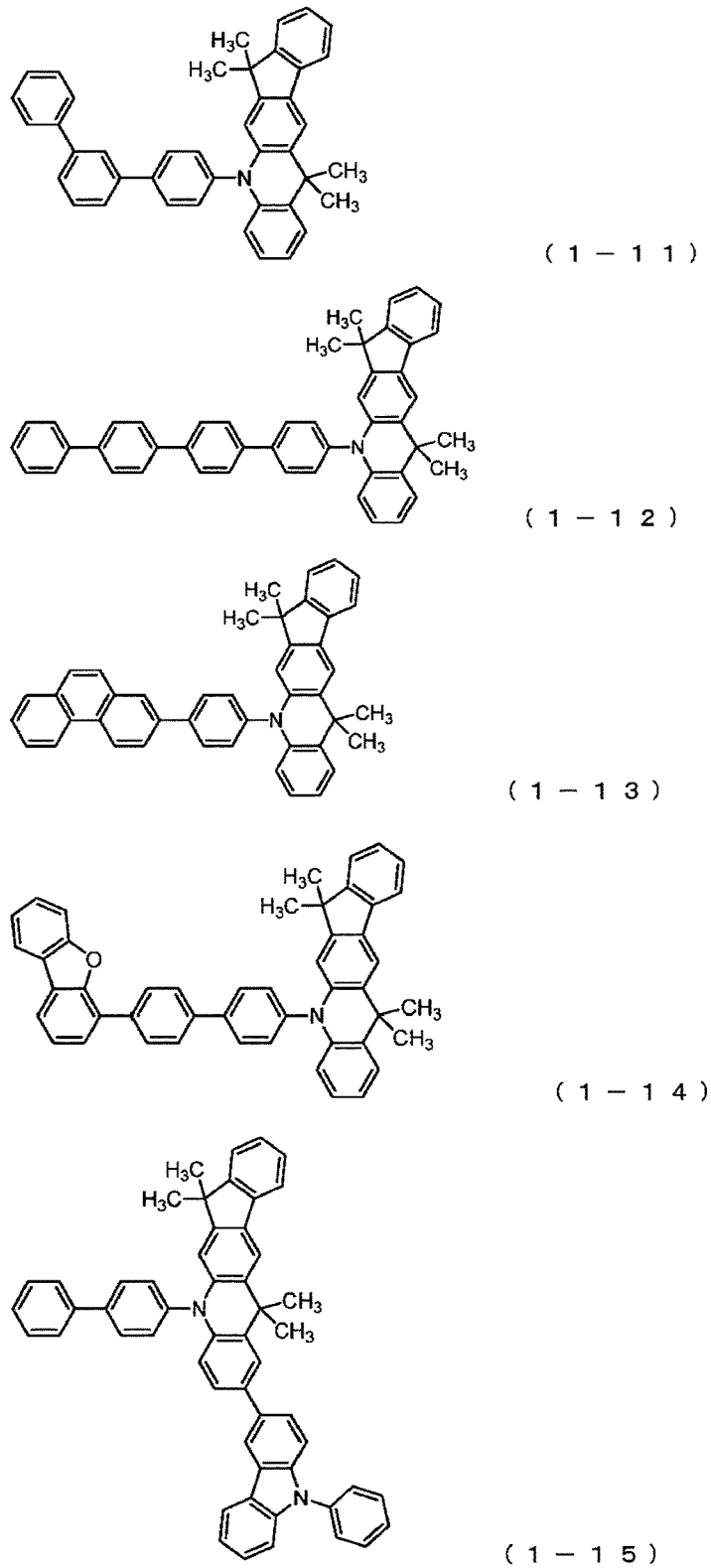
FIG. 12 is a diagram showing the structural formulas of Compound Nos. (1-11) to (1-15) that are indenoacridan derivatives of general formula (1).
Figure 13:
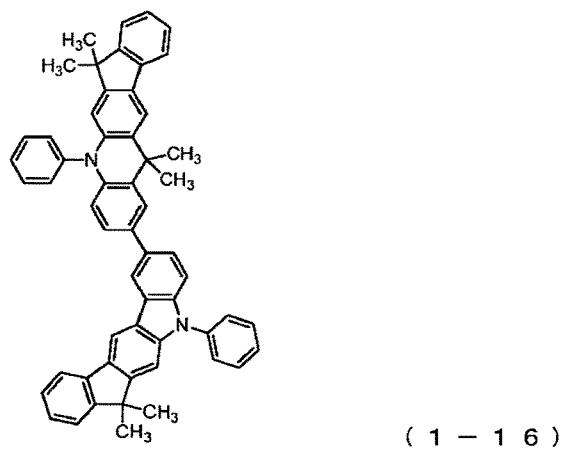
FIG. 13 is a diagram showing the structural formulas of Compound Nos. (1-16) to (1-19) that are indenoacridan derivatives of general formula (1).
Figure 13:
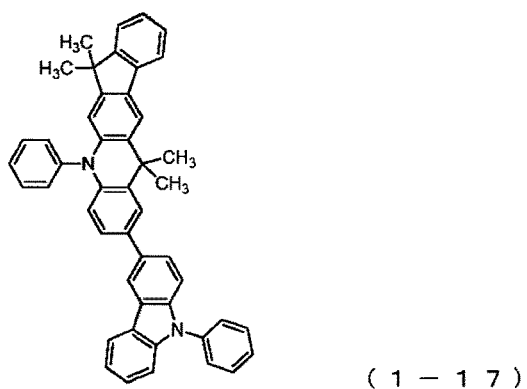
Figure 13:
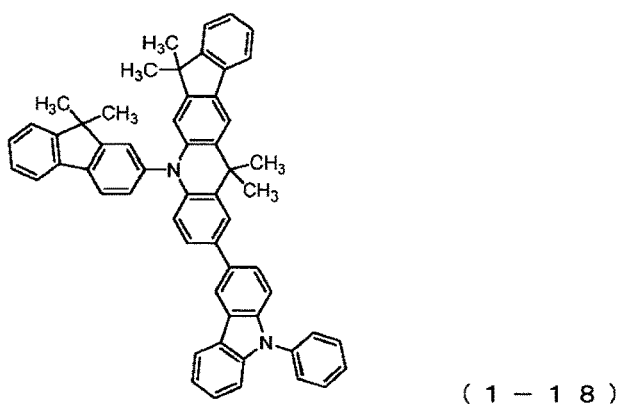
Figure 13:
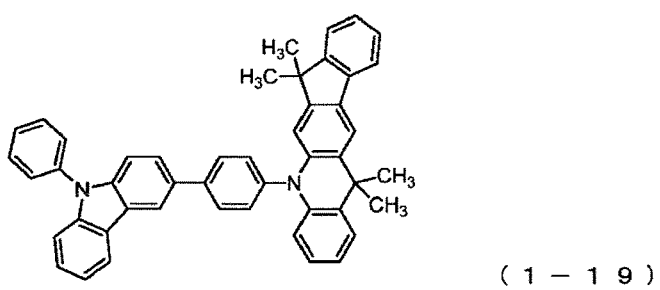
Figure 14:
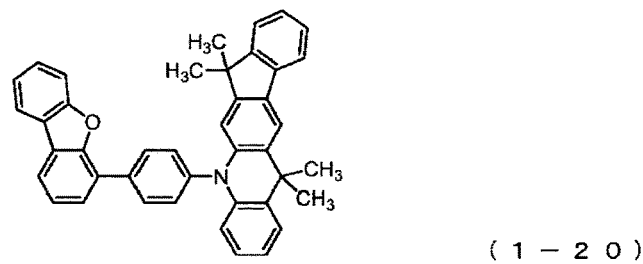
FIG. 14 is a diagram showing the structural formulas of Compound Nos. (1-20) to (1-24) that are indenoacridan derivatives of general formula (1).
Figure 14:
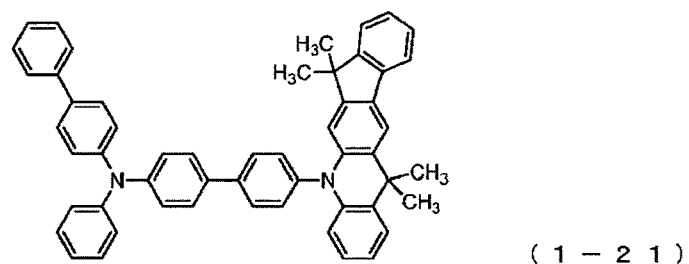
Figure 14:
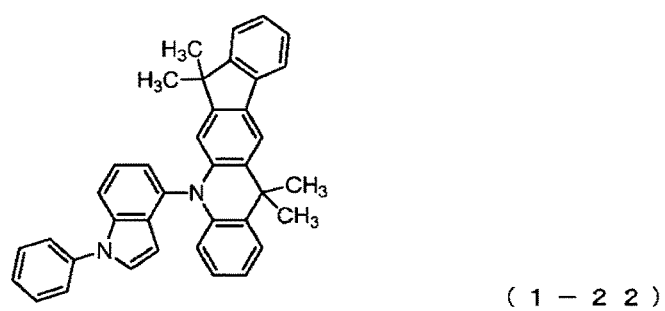
Figure 14:
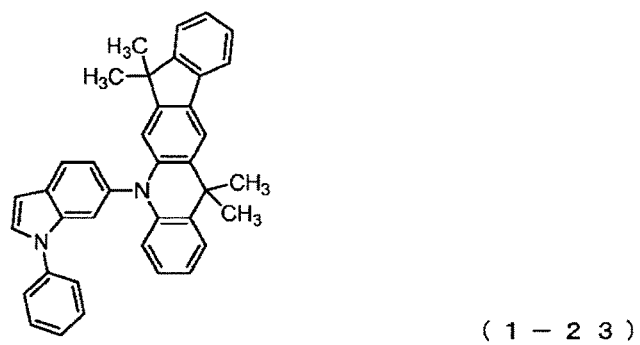
Figure 14:
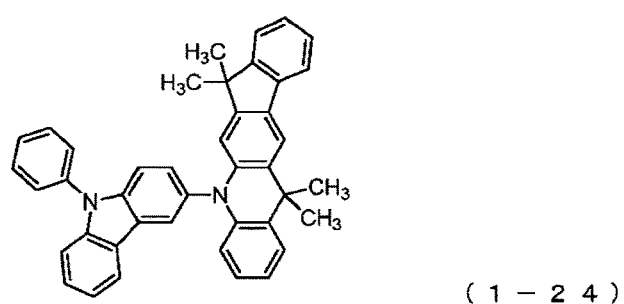
Figure 15:
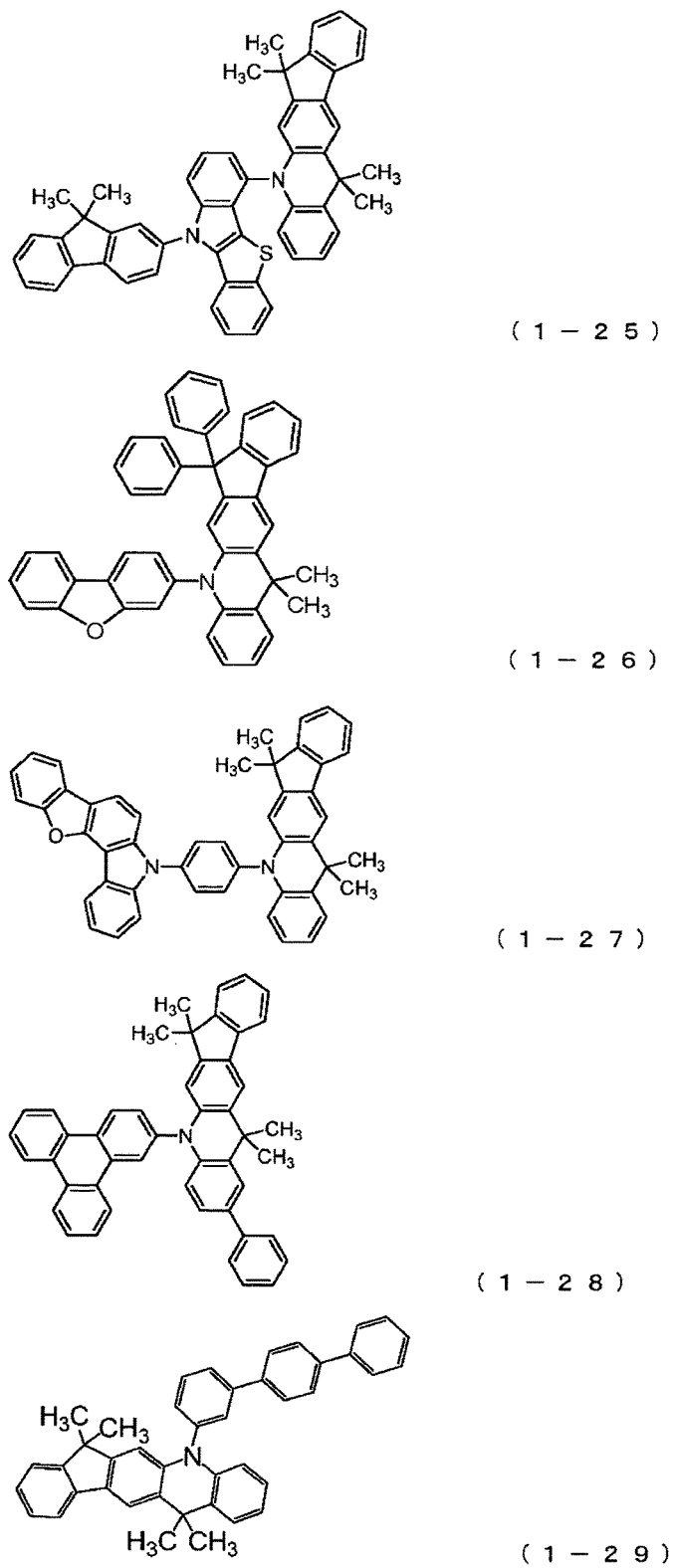
FIG. 15 is a diagram showing the structural formulas of Compound Nos. (1-25) to (1-29) that are indenoacridan derivatives of general formula (1).
Figure 16:
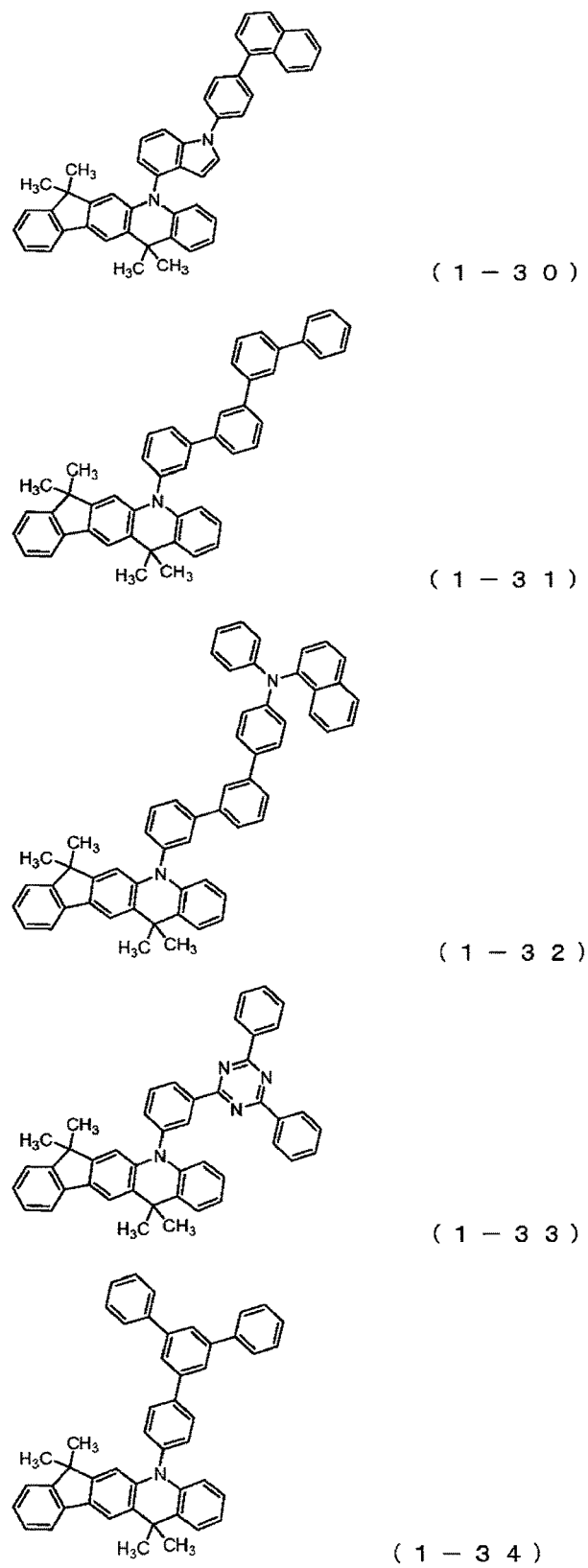
FIG. 16 is a diagram showing the structural formulas of Compound Nos. (1-30) to (1-34) that are indenoacridan derivatives of general formula (1).
Figure 17:
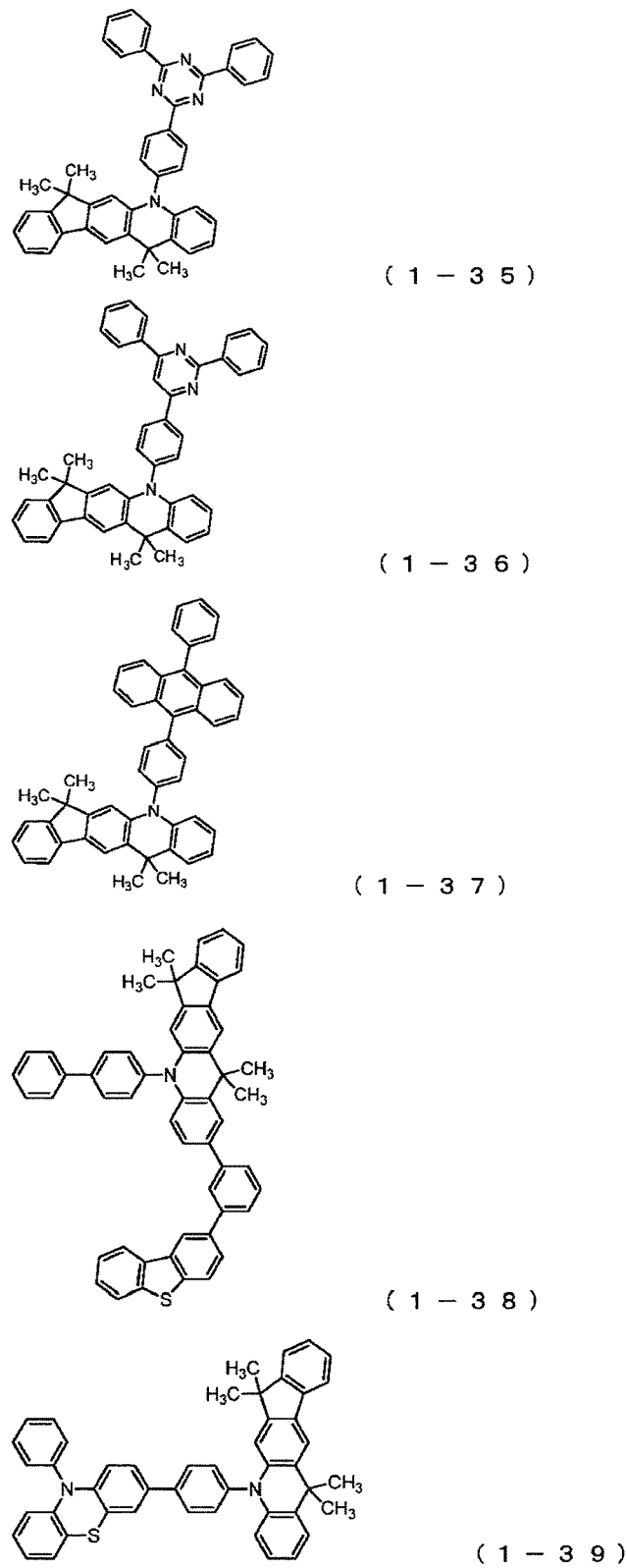
FIG. 17 is a diagram showing the structural formulas of Compound Nos. (1-35) to (1-39) that are indenoacridan derivatives of general formula (1).
Figure 18:
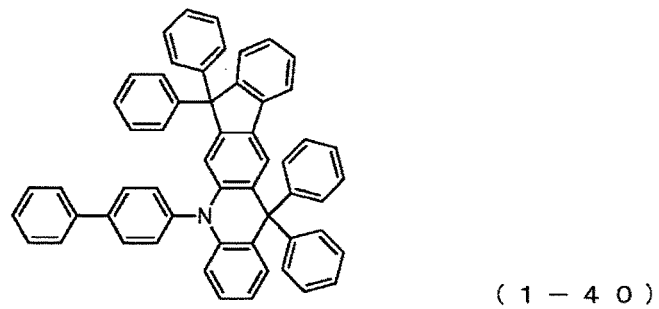
FIG. 18 is a diagram showing the structural formulas of Compound Nos. (1-40) to (1-44) that are indenoacridan derivatives of general formula (1).
Figure 18:
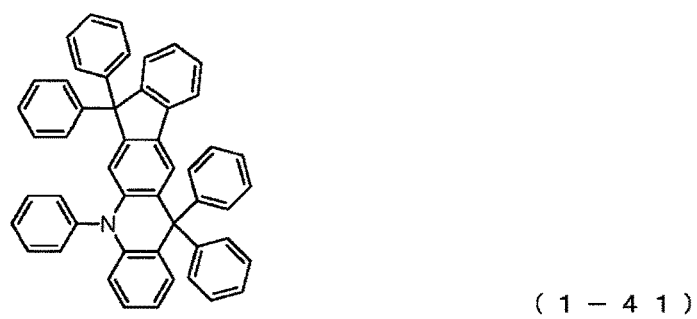
Figure 18:
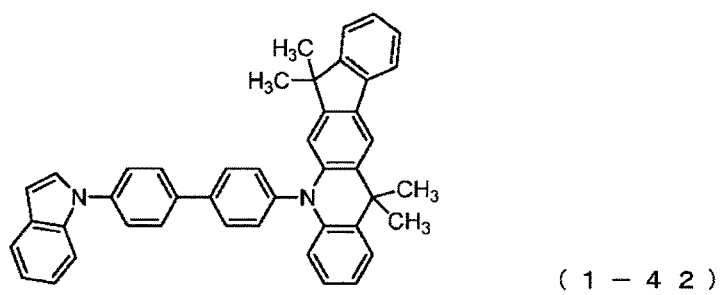
Figure 18:
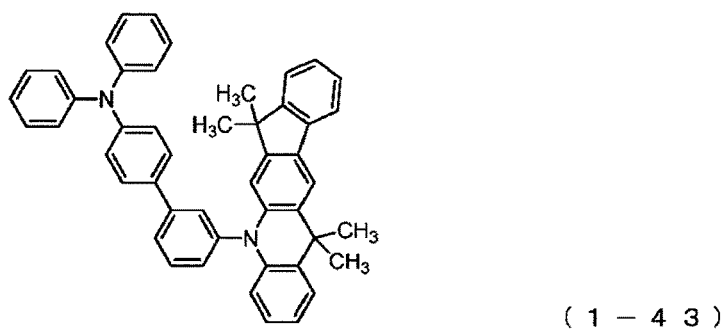
Figure 18:
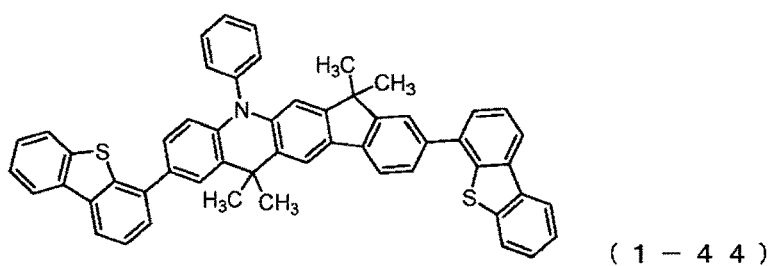
Figure 19:
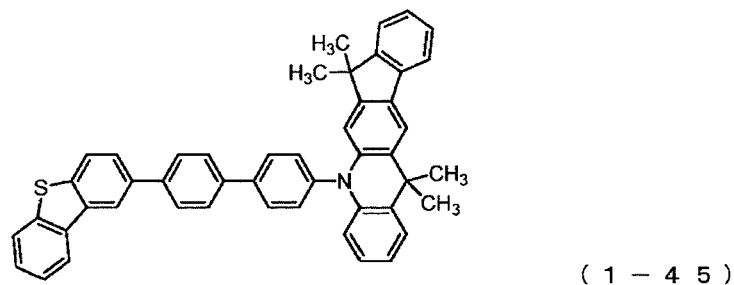
FIG. 19 is a diagram showing the structural formulas of Compound Nos. (1-45) to (1-47) that are indenoacridan derivatives of general formula (1).
Figure 19:
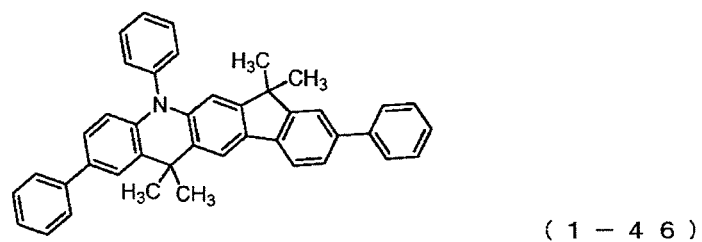
Figure 19:
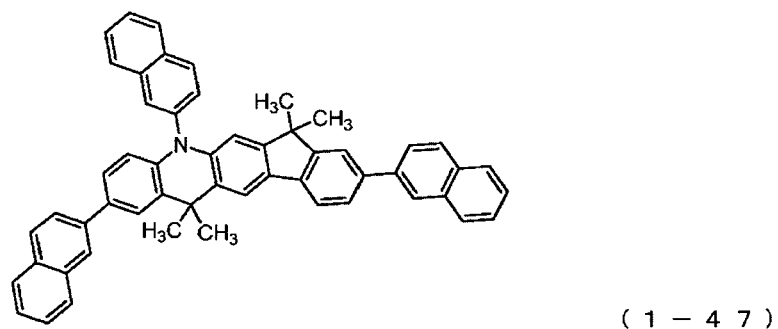

The structure of the obtained white powder was identified using NMR. The NMR chart is shown in FIG. 9.
The following 35 hydrogen signals were detected in $^1$H-NMR (THF-$d_8$).
δ (ppm)=7.89 (1H)
7.67 (1H)
7.59 (1H)
7.42-7.50 (6H)
7.10-7.38 (10H)
6.83-6.97 (2H)
6.39 (1H)
6.25 (1H)
2.48 (6H)
1.31 (6H)

Example 9

The glass transition temperature of the indenoacridan compounds obtained in Examples 1 to 8 was determined with a high-sensitivity differential scanning calorimeter (DSC 3100SA, from Bruker AXS K.K.). The results were as follows.

| | Glass transition temperature |
|---|---|
| Example 1 (Compound 1-1) | 126° C. |
| Example 2 (Compound 1-3) | 116° C. |
| Example 3 (Compound 1-4) | 127° C. |
| Example 4 (Compound 1-5) | 154° C. |
| Example 5 (Compound 1-6) | 141° C. |
| Example 6 (Compound 1-7) | 143° C. |
| Example 7 (Compound 1-8) | 115° C. |
| Example 8 (Compound 1-9) | 167° C. |

From the above results, the indenoacridan derivatives resented by the general formula (1) have the glass transition temperature of 100° C. or above, in particular 110° C. or above, and so it is apparent that the thin-film state is stable.

Example 10

Using the indenoacridan compounds obtained in Examples 1 to 8, vapor-deposited films having a thickness of 100 nm were produced on ITO substrates, and the work functions were measured using an ionization potential measuring device (PYS-202, from Sumitomo Heavy Industries, Ltd.).

The results were as follows.

|  | Working function |
| --- | --- |
| Example 1 (Compound 1-1) | 5.66 eV |
| Example 2 (Compound 1-3) | 5.68 eV |
| Example 3 (Compound 1-4) | 5.66 eV |
| Example 4 (Compound 1-5) | 5.68 eV |
| Example 5 (Compound 1-6) | 5.69 eV |
| Example 6 (Compound 1-7) | 5.67 eV |
| Example 7 (Compound 1-8) | 5.68 eV |
| Example 8 (Compound 1-9) | 5.69 eV |

From the above results, the indenoacridan derivatives represented by the general formula (1) demonstrate suitable energy levels compared with the work functions of 5.54 eV possessed by typical hole-transporting materials such as NPD and TPD, and thus have good hole-transporting abilities.

Example 11

<Synthesis of N-Aromatic Substituted Indenoindole Compound 2-1>

| A nitrogen-purged reactor was charged with | 4.9 g, |
| --- | --- |
| 7,7-dimethyl-7,12-dihydrobenzo[4,5]-thieno[3,2-g]indeno[1,2-b]indole | |
| 2-chloro-4-phenylquinazoline | 5.7 g, |
| tris(dibenzylideneacetone)dipalladium | 0.3 g, |
| tri-tert-butylphosphonium tetrafluoroborate | 0.4 g, |
| tert-butoxysodium | 4.0 g and |
| xylene | 74 mL. |

This was followed by heated and stirred for 12 hours under refluxing.

The system was cooled to room temperature and ethyl acetate and water were added, then, a liquid separation operation was carried out and the organic layer was collected. The organic layer was concentrated, and purification was carried out by column chromatography, giving as a powder 3.0 g (yield, 38%) of 7,7-dimethyl-12-(4-phenylquinazolin-2-yl)-7,12-dihydrobenzo[4,5]thieno[3,2-g]indeno[1,2-b]indole (Compound 2-1) having the structural formula shown below.

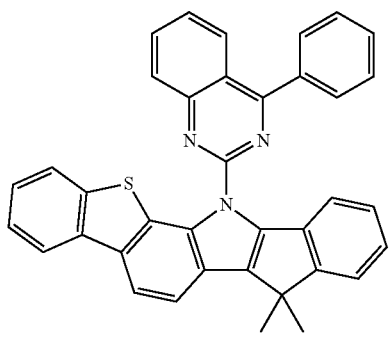

(2-1)

Example 12

<Synthesis of N-Aromatic Substituted Indenoindole Compound 2-2>

The reaction was carried out under the same conditions as in Example 11 except that 2-chloro-4-phenylbenzo[h]quinazoline was used instead of 2-chloro-4-phenylquinazoline, thereby giving as a powder 3.2 g (yield, 38%) of 7,7-dimethyl-12-(4-phenylbenzo[h]quinazolin-2-yl)-7,12-dihydrobenzo[4,5]thieno[3,2-g]indeno[1,2-b]indole (Compound 2-2) having the structural formula shown below.

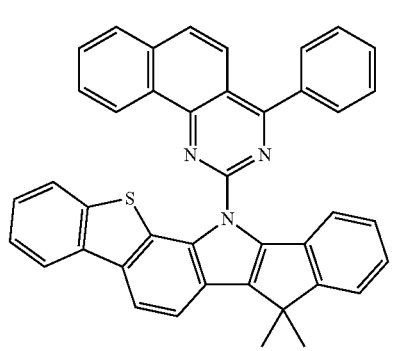

(2-2)

Example 13

<Synthesis of N-Aromatic Substituted Indenoindole Compound 2-3>

The reaction was carried out under the same conditions as in Example 11 except that 2-chloro-4,7-diphenylquinazoline was used instead of 2-chloro-4-phenylquinazoline, thereby giving as a powder 3.3 g (yield, 38%) of 12-(4,7-diphenylquinazolin-2-yl)-7,7-dimethyl-7,12-dihydrobenzo[4,5]thieno[3,2-g]indeno[1,2-b]indole (Compound 2-3) having the structural formula shown below.

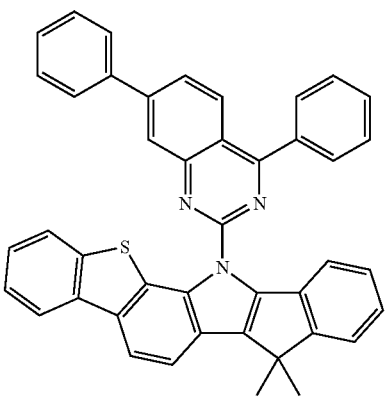

(2-3)

Example 14

<Synthesis of N-Aromatic Substituted Indenoindole Compound 2-4>

The reaction was carried out under the same conditions as in Example 11 except that 2-chloro-4,6-diphenylquinazoline was used instead of 2-chloro-4-phenylquinazoline, thereby giving as a powder 3.3 g (yield, 38%) of 12-(4,6-diphenylquinazolin-2-yl)-7,7-dimethyl-7,12-dihydrobenzo[4,5]thieno[3,2-g]indeno[1,2-b]indole (Compound 2-4) having the structural formula shown below.

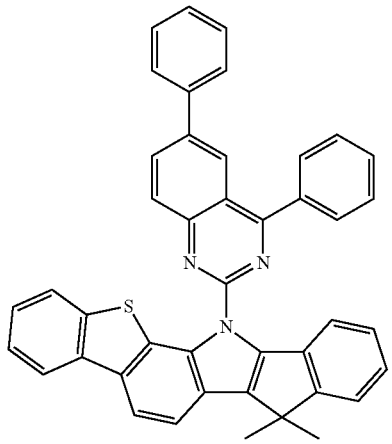

(2-4)

Example 15

<Synthesis of N-Aromatic Substituted Indenoindole Compound 2-5>

The reaction was carried out under the same conditions as in Example 11 except that 13,13-dimethyl-8,13-dihydrobenzo[4,5]thieno[3,2-e]indeno[1,2-b]indole was used instead of 7,7-dimethyl-7,12-dihydrobenzo[4,5]thieno[3,2-g]indeno[1,2-b]indole, thereby giving as a powder 3.0 g (yield, 38%) of 13,13-dimethyl-8-(4-phenylquinazolin-2-yl)-8,13-dihydrobenzo[4,5]thieno[3,2-e]indeno[1,2-b]indole (Compound 2-5) having the structural formula shown below.

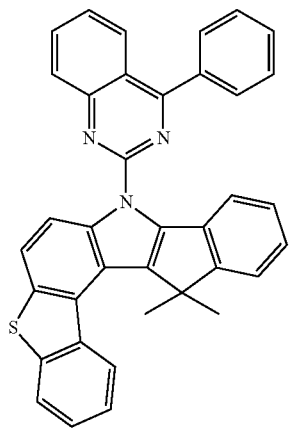

(2-5)

Example 16

<Synthesis of N-Aromatic Substituted Indenoindole Compound 2-6>

The reaction was carried out under the same conditions as in Example 15 except that 2-chloro-4,6-diphenylquinazoline was used instead of 2-chloro-4-phenylquinazoline, thereby giving as a powder 3.3 g (yield, 38%) of 8-(4,6-diphenylquinazolin-2-yl)-13,13-dimethyl-8,13-dihydro benzo[4,5]thieno[3,2-e]indeno[1,2-b]indole (Compound 2-6) having the structural formula shown below.

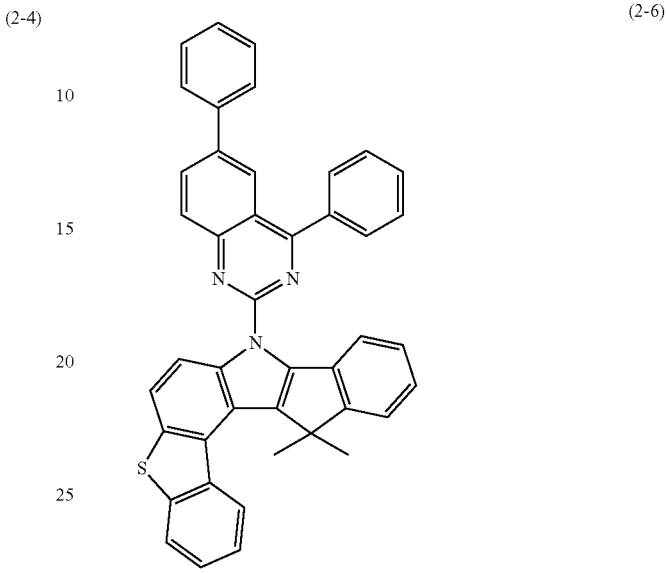

(2-6)

Example 17

<Synthesis of N-Aromatic Substituted Indenoindole Compound 2-7>

The reaction was carried out under the same conditions as in Example 11 except that 7,7,13,13-tetramethyl-7,13-dihydro-5H-diindeno[1,2-b:1',2'-f]indole was used instead of 7,7-dimethyl-7,12-dihydrobenzo[4,5]thieno[3,2-g]indeno[1,2-b]indole, thereby giving as a powder 3.0 g (yield, 38%) of 7,7,13,13-tetramethyl-5-(4-phenylquinazolin-2-yl)-7,13-dihydro-5H-diindeno[1,2-b:1',2'-f]indole (Compound 2-7) having the structural formula shown below.

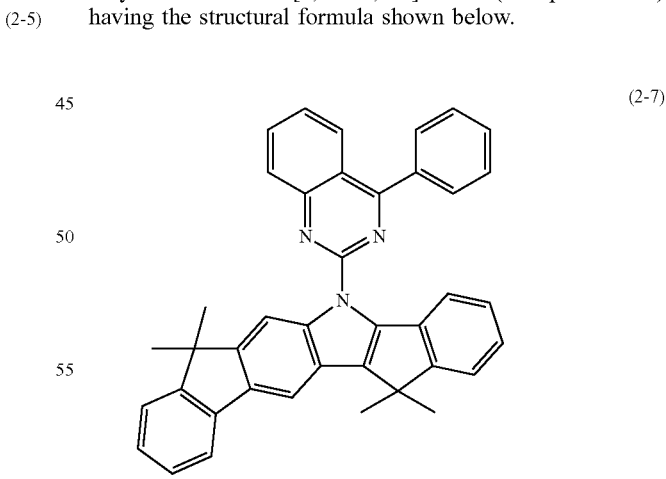

(2-7)

Example 18

<Synthesis of N-Aromatic Substituted Indenoindole Compound 2-8>

The reaction was carried out under the same conditions as in Example 17 except that 2-(3-bromophenyl)-4-phenylquinazoline was used instead of 2-chloro-4-phenylquinazoline, thereby giving as a powder 3.4 g (yield, 38%) of 7,7,13,13-tetramethyl-5-[3-(4-phenylquinazolin-2-yl)phenyl]-7,13-dihydro-5H-diindeno[1,2-b:1',2'-f]indole (Compound 2-8) having the structural formula shown below.

(2-8)

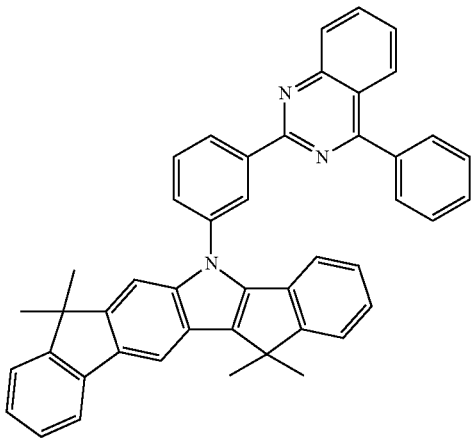

Example 19

<Synthesis of N-Aromatic Substituted Indenoindole Compound 2-9>

The reaction was carried out under the same conditions as in Example 12 except that 7,7-dimethyl-7,12-dihydrobenzofuro[3,2-g]indeno[1,2-b]indole was used instead of 7,7-dimethyl-7,12-dihydrobenzo[4,5]thieno[3,2-g]indeno[1,2-b]indole, thereby giving as a powder 3.0 g (yield, 38%) of 7,7-dimethyl-12-(4-phenylbenzo[h]quinazolin-2-yl)-7,12-dihydrobenzofuro[3,2-g]indeno[1,2-b]indole (Compound 2-9) having the structural formula shown below.

(2-9)

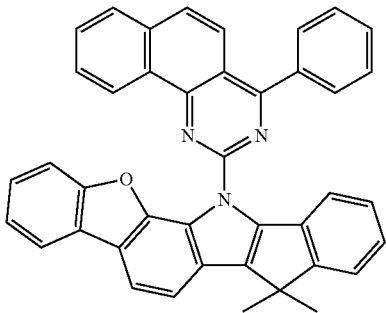

Example 20

<Synthesis of N-Aromatic Substituted Indenoindole Compound 2-10>

The reaction was carried out under the same conditions as in Example 19 except that 2-chloro-4,6-diphenylbenzo[h]quinazoline was used instead of 2-chloro-4-phenylbenzo[h]quinazoline, thereby giving as a powder 3.5 g (yield, 38%) of 12-(4,6-diphenylbenzo[h]quinazolin-2-yl)-7,7-dimethyl-7,12-dihydrobenzofuro[3,2-g]indeno[1,2-b]indole (Compound 2-10) having the structural formula shown below.

(2-10)

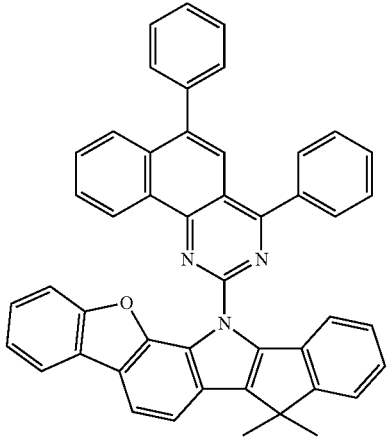

Example 21

<Synthesis of N-Aromatic Substituted Indenoindole Compound 2-11>

The reaction was carried out under the same conditions as in Example 11 except that 13,13-dimethyl-8,13-dihydrobenzofuro[3,2-e]indeno[1,2-b]indole was used instead of 7,7-dimethyl-7,12-dihydrobenzo[4,5]thieno[3,2-g]indeno[1,2-b]indole, thereby giving as a powder 3.0 g (yield, 38%) of 13,13-dimethyl-8-(4-phenylquinazolin-2-yl)-8,13-dihydrobenzofuro[3,2-e]indeno[1,2-b]indole (Compound 2-11) having the structural formula shown below.

(2-11)

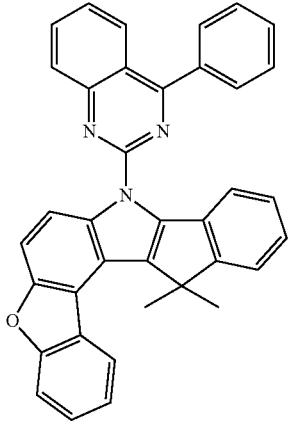

Example 22

<Synthesis of N-Aromatic Substituted Indenoindole Compound 2-12>

The reaction was carried out under the same conditions as in Example 21 except that 2-chloro-4,6-diphenylquinazoline was used instead of 2-chloro-4-phenylquinazoline, thereby giving as a powder 3.2 g (yield, 38%) of 13,13-dimethyl-8-(4,6-diphenylquinazolin-2-yl)-8,13-dihydrobenzofuro[3,2-e]indeno[1,2-b]indole (Compound 2-12) having the structural formula shown below.

(2-12)

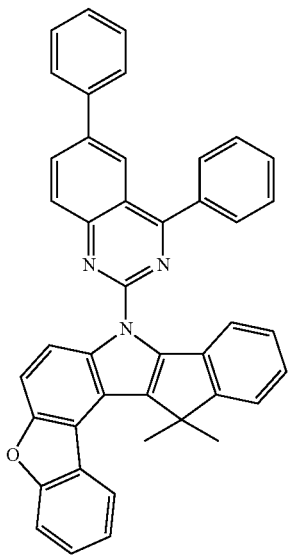

Example 23

<Synthesis of N-Aromatic Substituted Carbazole Compound 3-1>

The reaction was carried out under the same conditions as in Example 22 except that 7,7-dimethyl-7,13-dihydroindeno[2',1':4,5]thieno[2,3-a]carbazole was used instead of 13,13-dimethyl-8,13-dihydrobenzofuro[3,2-e]indeno[1,2-b]indole, thereby giving as a powder 7.0 g (yield, 38%) of 13-(4,6-diphenylquinazolin-2-yl)-7,7-dimethyl-7,13-dihydroindeno[2',1':4,5]thieno[2,3-a]carbazole (Compound 3-1) having the structural formula shown below.

(3-1)

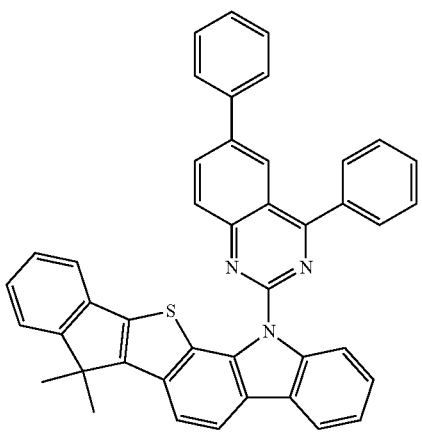

Example 24

<Synthesis of N-Aromatic Substituted Carbazole Compound 3-2>

The reaction was carried out under the same conditions as in Example 23 except that 4-(biphenyl-4-yl)-2-chloroquinazoline was used instead of 2-chloro-4,6-diphenylquinazoline, thereby giving as a powder 6.7 g (yield, 37%) of 13-[4-(biphenyl-4-yl)quinazolin-2-yl]-7,7-dimethyl-7,13-dihydroindeno[2',1':4,5]thieno[2,3-a]carbazole (Compound 3-2) having the structural formula shown below.

(3-2)

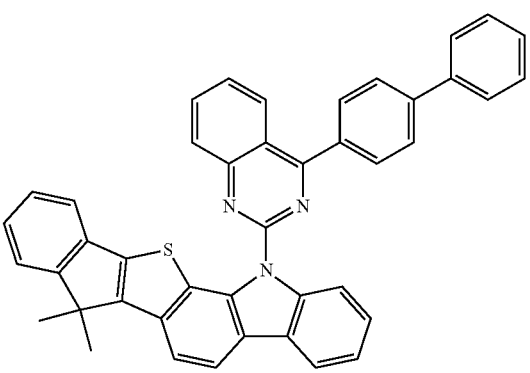

Example 25

<Synthesis of N-Aromatic Substituted Carbazole Compound 3-3>

The reaction was carried out under the same conditions as in Example 23 except that 2-chloro-4-(phenyl-$d_5$)quinazoline was used instead of 2-chloro-4,6-diphenylquinazoline, thereby giving as a powder 8.4 g (yield, 32%) of 7,7-dimethyl-13-[4-(phenyl-$d_5$)quinazolin-2-yl]-7,13-dihydroindeno[2',1':4,5]thieno[2,3-a]carbazole (Compound 3-3).

(3-3)

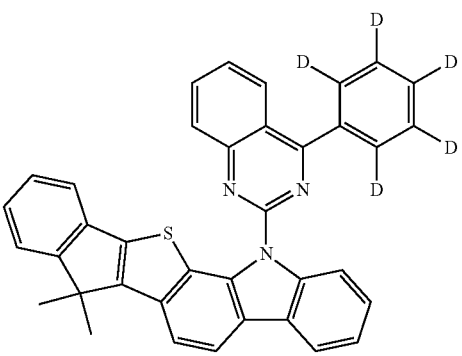

Example 26

<Synthesis of N-Aromatic Substituted Carbazole Compound 3-4>

The reaction was carried out under the same conditions as in Example 23 except that 2-(4-bromophenyl)-4-phenylquinazoline was used instead of 2-chloro-4,6-diphenylquinazoline, thereby giving as a powder 5.2 g (yield, 28%) of 7,7-dimethyl-13-[4-(4-phenylquinazolin-2-yl)phenyl]-7,13-dihydroindeno[2',1':4,5]thieno[2,3-a]carbazole (Compound 3-4).

(3-4)

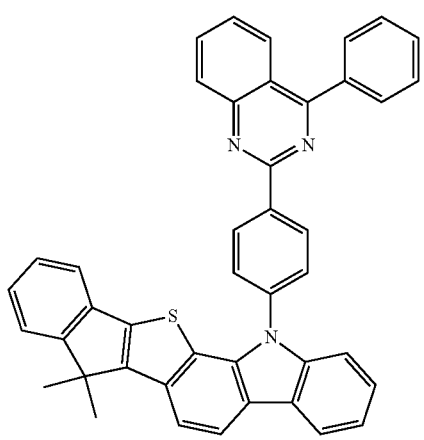

Example 27

<Synthesis of N-Aromatic Substituted Carbazole Compound 3-5>

The reaction was carried out under the same conditions as in Example 23 except that 2-(3-bromophenyl)-4-phenylquinazoline was used instead of 2-chloro-4,6-diphenylquinazoline, thereby giving as a powder 8.4 g (yield, 32%) of 7,7-dimethyl-13-[3-(4-phenylquinazolin-2-yl)phenyl]-7,13-dihydroindeno[2',1':4,5]thieno[2,3-a]carbazole (Compound 3-5).

(3-5)

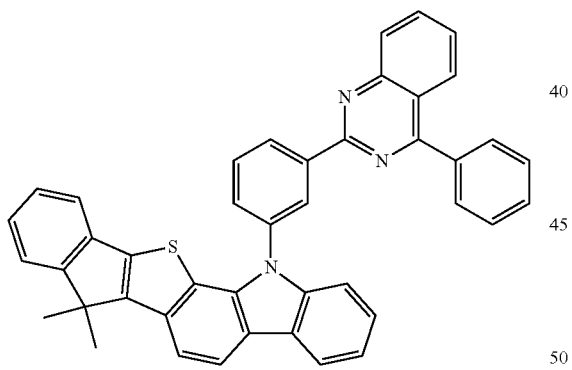

Example 28

<Synthesis of N-Aromatic Substituted Carbazole Compound 3-6>

The reaction was carried out under the same conditions as in Example 23 except that 2-chloro-4-phenylbenzo[h]quinazoline was used instead of 2-chloro-4,6-diphenylquinazoline, thereby giving as a powder 8.4 g (yield, 32%) of 7,7-dimethyl-13-(4-phenylbenzo[h]quinazolin-2-yl)-7,13-dihydroindeno[2',1':4,5]thieno[2,3-a]carbazole (Compound 3-6).

(3-6)

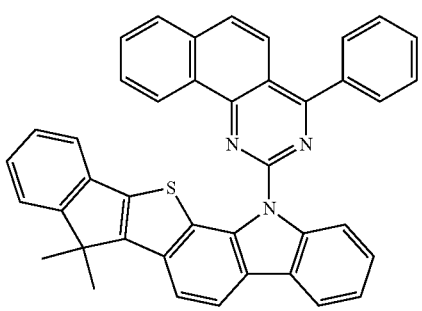

Example 29

<Synthesis of N-Aromatic Substituted Carbazole Compound 3-7>

The reaction was carried out under the same conditions as in Example 28 except that 8,8-dimethyl-5,8-dihydroindeno[2',1':4,5]thieno[3,2-c]carbazole was used instead of 7,7-dimethyl-7,13-dihydroindeno[2',1':4,5]thieno[2,3-a]carbazole, thereby giving as a powder 9.3 g (yield, 35%) of 8,8-dimethyl-5-(4-phenylbenzo[h]quinazolin-2-yl)-5,8-dihydroindeno[2',1':4,5]thieno[3,2-c]carbazole (Compound 3-7).

(3-7)

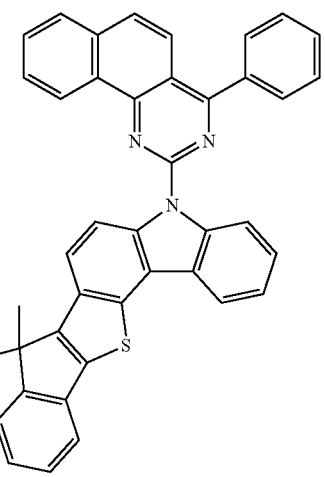

Example 30

<Synthesis of N-Aromatic Substituted Carbazole Compound 3-8>

The reaction was carried out under the same conditions as in Example 11 except that 7,7-dimethyl-7,13-dihydroindeno[2',1':4,5]furo[2,3-a]carbazole was used instead of 7,7-dimethyl-7,12-dihydrobenzo[4,5]thieno[3,2-g]indeno[1,2-b]indole, thereby giving as a powder 6.2 g (yield, 32%) of 7,7-dimethyl-13-(4-phenylquinazolin-2-yl)-7,13-dihydroindeno[2',1':4,5]furo[2,3-a]carbazole (Compound 3-8).

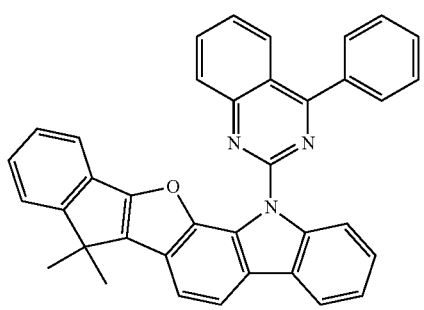

(3-8)

Example 31

<Synthesis of N-Aromatic Substituted Carbazole Compound 3-9>

The reaction was carried out under the same conditions as in Example 30 except that 2-chloro-4-phenylbenzo[h]quinazoline was used instead of 2-chloro-4-phenylquinazoline, thereby giving as a powder 8.6 g (yield, 30%) of 7,7-dimethyl-13-(4-phenylbenzo[h]quinazolin-2-yl)-7,13-dihydroindeno[2',1':4,5]furo[2,3-a]carbazole (Compound 3-9).

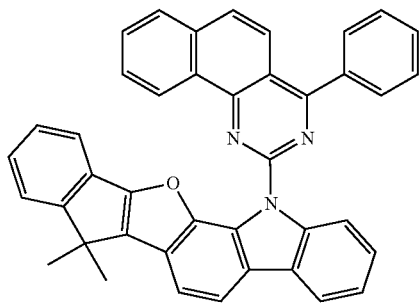

(3-9)

Example 32

<Synthesis of N-Aromatic Substituted Carbazole Compound 3-10>

The reaction was carried out under the same conditions as in Example 30 except that 2-chloro-4,6-diphenylquinazoline was used instead of 2-chloro-4-phenylquinazoline, thereby giving as a powder 7.2 g (yield, 29%) of 13-(4,6-diphenylquinazolin-2-yl)-7,7-dimethyl-7,13-diydroindeno[2',1'4,5]furo[2,3-a]carbazole (Compound 3-10).

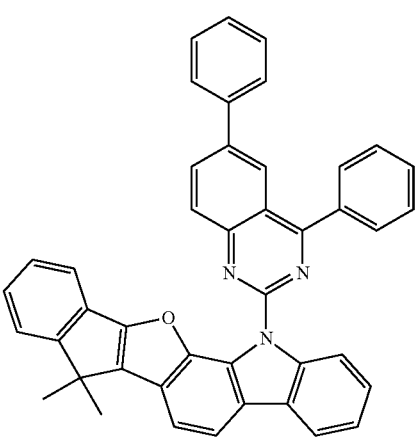

(3-10)

Example 33

<Synthesis of N-Aromatic Substituted Carbazole Compound 3-11>

The reaction was carried out under the same conditions as in Example 11 except that 7,7-diphenyl-7,13-dihydroindeno[2',1':4,5]thieno[2,3-a]carbazole was used instead of 7,7-dimethyl-7,12-dihydrobenzo[4,5]thieno[3,2-g]indeno[1,2-b]indole, thereby giving as a powder 6.7 g (yield, 37%) of 7,7-diphenyl-13-(4-phenylquinazolin-2-yl)-7,13-dihydroindeno[2',1':4,5]thieno[2,3-a]carbazole (Compound 3-11).

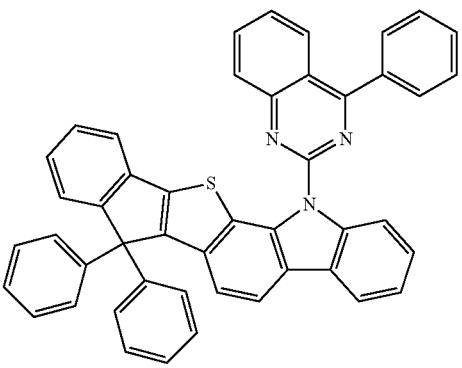

(3-11)

Example 34

<Synthesis of N-Aromatic Substituted Carbazole Compound 3-12>

The reaction was carried out under the same conditions as in Example 11 except that 9,9-dimethyl-9,15-dihydrobenzo[a]indeno[2',1':4,5]thieno[3,2-i]carbazole was used instead of 7,7-dimethyl-7,12-dihydrobenzo[4,5]thieno[3,2-g]indeno[1,2-b]indole, thereby giving as a powder 4.8 g (yield, 42%) of 9,9-dimethyl-15-(4-phenylquinazolin-2-yl)-9,15-dihydrobenzo[a]indeno[2',1':4,5]thieno[3,2-i]carbazole (Compound 3-12).

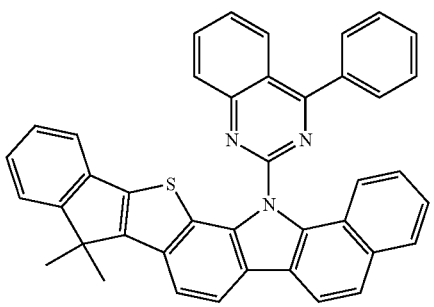

(3-12)

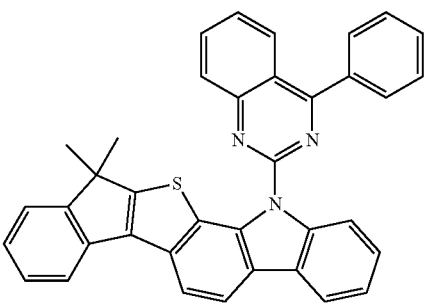

(3-14)

Example 35

<Synthesis of N-Aromatic Substituted Carbazole Compound 3-13>

The reaction was carried out under the same conditions as in Example 11 except that 7-phenyl-7,13-dihydroindolo[2', 3':4,5]thieno[2,3-a]carbazole was used instead of 7,7-dimethyl-7,12-dihydrobenzo[4,5]thieno[3,2-g]indeno[1,2-b]indole, thereby giving as a powder 4.3 g (yield, 43%) of 7-phenyl-13-(4-phenylquinazolin-2-yl)-7,13-dihydroindolo[2',3': 4,5]thieno[2,3-a]carbazole (Compound 3-13).

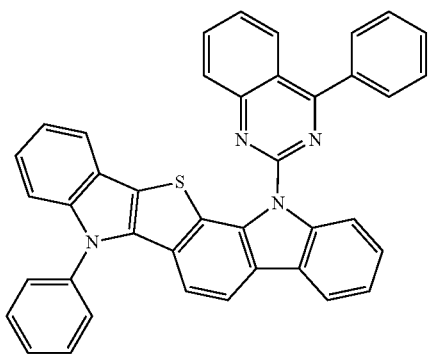

(3-13)

Example 36

<Synthesis of N-Aromatic Substituted Carbazole Compound 3-14>

The reaction was carried out under the same conditions as in Example 11 except that 12,12-dimethyl-1,12-dihydroindeno[1',2':4,5]thieno[2,3-a]carbazole was used instead of 7,7-dimethyl-7,12-dihydrobenzo[4,5]thieno[3,2-g]indeno[1,2-b]indole, thereby giving as a powder 6.3 g (yield, 44%) of 12,12-dimethyl-1-(4-phenylquinazolin-2-yl)-1,12-dihydroindeno[1',2':4,5]thieno[2,3-a]carbazole (Compound 3-14).

<Synthesis of N-Aromatic Substituted Carbazole Compound 3-15>

The reaction was carried out under the same conditions as in Example 23 except that 2-bromonaphthalene was used instead of 2-chloro-4,6-diphenylquinazoline, thereby giving as a powder 5.4 g (yield, 47%) of 7,7-dimethyl-13-(naphthalen-2-yl)-7,13-dihydroindeno[2',1':4,5]thieno[2,3-a]carbazole (Compound 3-15).

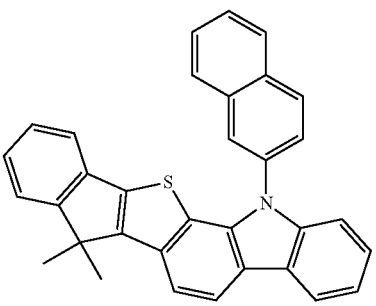

(3-15)

Example 38

An organic EL device having the device construction shown in FIG. 1 was fabricated by vapor deposition according to the following procedure.

First, an ITO-coated glass substrate in which an ITO electrode (transparent anode 2) with a film thickness of 150 nm was formed on a glass substrate (transparent substrate 1) was prepared.

This glass substrate 1 was ultrasonically cleaned for 20 minutes in isopropyl alcohol, and then dried for 10 minutes on a hot plate heated to 200° C. UV/ozone treatment was subsequently carried out for 15 minutes. Then, this ITO-coated glass substrate was attached inside a vacuum vapor deposition device, and pressure was reduced to 0.001 Pa or less.

Next, the compound of the structural formula shown below (HIM-1) was formed to a film thickness of 5 nm as the hole injection layer 3 so as to cover the transparent anode 2.

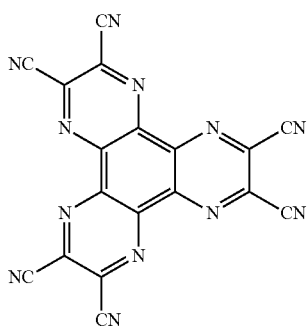

(HIM-1)

On this hole injection layer 3, Arylamine Compound (5-1) of the following structural formula having two triphenylamine structures in the molecule was used to form a first hole transport layer 5a having a film thickness of 60 nm.

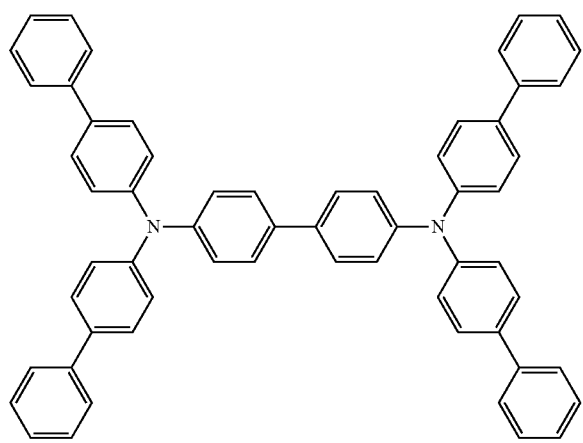

(5-1)

On the first hole transport layer 5a thus formed, Indenoacridan Compound (1-1) synthesized in Example 1 was used to form a second hole transport layer 5b having a film thickness of 5 nm.

On this second hole transport layer 5b, Compound EMD-1 of the structural formula shown below and N-Aromatic Substituted Indenoindole Compound (2-2) synthesized in Example 12 were binary vapor deposited at deposition rates such that the deposition rate ratio of EMD-1: Compound (2-2)=5:95, thereby forming a luminous layer 6 having a film thickness of 20 nm.

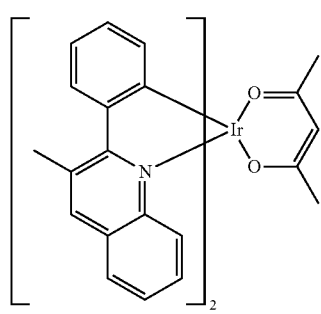

(EMD-1)

On the luminous layer 6 thus formed, Anthracene Derivative (4a-1) of the structural formula shown below and ETM-1 of the structural formula shown below were binary vapor deposited at deposition rates such that the deposition rate ratio of Anthracene Derivative (4a-1):ETM-1=50:50, thereby forming an electron transport layer 7 having a film thickness of 30 nm.

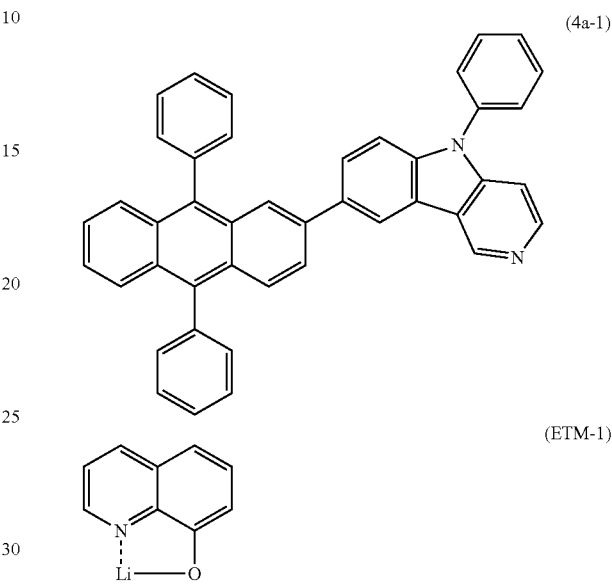

(4a-1)

(ETM-1)

Using lithium fluoride, an electron injection layer 8 having a film thickness of 1 nm was formed on the electron transport layer 7.

Finally, a cathode 9 was formed by vapor depositing 100 nm of aluminum.

The produced organic EL device was measured for the characteristics exhibited at normal temperature in the atmosphere.

The layer construction of this organic EL device is shown in Table 1, and the measured emission characteristics when direct-current voltage was applied to the organic EL device are shown in Table 3.

The device life was measured as the time until the luminance attenuated to 6,790 cd/m$^2$ (corresponding to 97% when the initial luminance is 100%:97% attenuation) when constant-current driving was carried out at an emission luminance at the start of light emission (initial brightness) set to 7,000 cd/m$^2$.

Example 39

Aside from using Indenoacridan Compound (1-3) synthesized in Example 2 to form a second hole transport layer 5b having a film thickness of 5 nm, an organic EL device was fabricated in the same way as in Example 38.

The layer construction of this organic EL device is shown in Table 1. The measured emission characteristics when direct-current voltage was applied to this organic EL device are shown in Table 3.

Example 40

Aside from using Indenoacridan Compound (1-4) synthesized in Example 3 to form a second hole transport layer 5b having a film thickness of 5 nm, an organic EL device was fabricated in the same way as in Example 38.

The layer construction of this organic EL device is shown in Table 1. The measured emission characteristics when direct-current voltage was applied to this organic EL device are shown in Table 3.

Example 41

Aside from using Indenoacridan Compound (1-5) synthesized in Example 4 to form a second hole transport layer 5b having a film thickness of 5 nm, an organic EL device was fabricated in the same way as in Example 38.

The layer construction of this organic EL device is shown in Table 1. The measured emission characteristics when direct-current voltage was applied to this organic EL device are shown in Table 3.

Example 42

Aside from using Indenoacridan Compound (1-6) synthesized in Example 5 to form a second hole transport layer 5b having a film thickness of 5 nm, an organic EL device was fabricated in the same way as in Example 38.

The layer construction of this organic EL device is shown in Table 1. The measured emission characteristics when direct-current voltage was applied to this organic EL device are shown in Table 3.

Example 43

Aside from using Indenoacridan Compound (1-7) synthesized in Example 6 to form a second hole transport layer 5b having a film thickness of 5 nm, an organic EL device was fabricated in the same way as in Example 38.

The layer construction of this organic EL device is shown in Table 1. The measured emission characteristics when direct-current voltage was applied to this organic EL device are shown in Table 3.

Example 44

An organic EL device was fabricated under the same conditions as in Example 38 except that N-Aromatic Substituted Carbazole Compound (3-9) synthesized in Example 31 was used and binary vapor deposition of this Compound (3-9) and EMD-1 was carried out at deposition rates such that the deposition rate ratio of EMD-1:Compound (3-9)=5:95 to form a luminous layer 6 having a film thickness of 20 nm.

The layer construction of this organic EL device is shown in Table 1. The measured emission characteristics when direct-current voltage was applied to this organic EL device are shown in Table 3.

Example 45

Aside from using Indenoacridan Compound (1-3) synthesized in Example 2 to form a second hole transport layer 5b having a film thickness of 5 nm, an organic EL device was fabricated in the same way as in Example 44.

The layer construction of this organic EL device is shown in Table 1. The measured emission characteristics when direct-current voltage was applied to this organic EL device are shown in Table 3.

Example 46

Aside from using Indenoacridan Compound (1-4) synthesized in Example 3 to forma second hole transport layer 5b having a film thickness of 5 nm, an organic EL device was fabricated in the same way as in Example 44.

The layer construction of this organic EL device is shown in Table 1. The measured emission characteristics when direct-current voltage was applied to this organic EL device are shown in Table 3.

Example 47

Aside from using Indenoacridan Compound (1-5) synthesized in Example 4 to form a second hole transport layer 5b having a film thickness of 5 nm, an organic EL device was fabricated in the same way as in Example 44.

The layer construction of this organic EL device is shown in Table 1. The measured emission characteristics when direct-current voltage was applied to this organic EL device are shown in Table 3.

Example 48

Aside from using Indenoacridan Compound (1-6) synthesized in Example 5 to form a second hole transport layer 5b having a film thickness of 5 nm, an organic EL device was fabricated in the same way as in Example 44.

The layer construction of this organic EL device is shown in Table 1. The measured emission characteristics when direct-current voltage was applied to this organic EL device are shown in Table 3.

Example 49

Aside from using Indenoacridan Compound (1-7) synthesized in Example 6 to form a second hole transport layer 5b having a film thickness of 5 nm, an organic EL device was fabricated in the same way as in Example 44.

The layer construction of this organic EL device is shown in Table 1. The measured emission characteristics when direct-current voltage was applied to this organic EL device are shown in Table 3.

Example 50

An organic EL device was fabricated under the same conditions as in Example 38 except that the N-Aromatic Substituted Carbazole Compound (3-16) represented by the structural formula shown below was used and binary vapor deposition of this Compound (3-16) and EMD-1 was carried out at deposition rates such that the deposition rate ratio of EMD-1:Compound (3-16)=5:95 to form a luminous layer 6 having a film thickness of 20 nm.

(3-16)

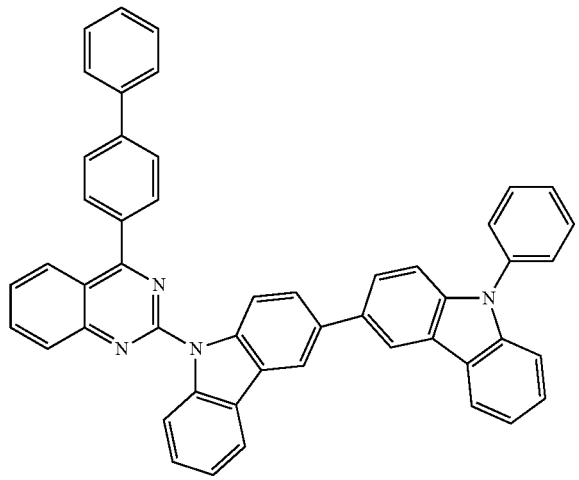

The layer construction of this organic EL device is shown in Table 2. The measured emission characteristics when direct-current voltage was applied to this organic EL device are shown in Table 4.

Example 51

Aside from using Indenoacridan Compound (1-3) synthesized in Example 2 to form a second hole transport layer 5b having a film thickness of 5 nm, an organic EL device was fabricated in the same way as in Example 50.

The layer construction of this organic EL device is shown in Table 2. The measured emission characteristics when direct-current voltage was applied to this organic EL device are shown in Table 4.

Example 52

Aside from using Indenoacridan Compound (1-4) synthesized in Example 3 to form a second hole transport layer 5b having a film thickness of 5 nm, an organic EL device was fabricated in the same way as in Example 50.

The layer construction of this organic EL device is shown in Table 2. The measured emission characteristics when direct-current voltage was applied to this organic EL device are shown in Table 4.

Example 53

Aside from using Indenoacridan Compound (1-5) synthesized in Example 4 to form a second hole transport layer 5b having a film thickness of 5 nm, an organic EL device was fabricated in the same way as in Example 50.

The layer construction of this organic EL device is shown in Table 2. The measured emission characteristics when direct-current voltage was applied to this organic EL device are shown in Table 4.

Example 54

Aside from using Indenoacridan Compound (1-6) synthesized in Example 5 to form a second hole transport layer 5b having a film thickness of 5 nm, an organic EL device was fabricated in the same way as in Example 50.

The layer construction of this organic EL device is shown in Table 2. The measured emission characteristics when direct-current voltage was applied to this organic EL device are shown in Table 4.

Example 55

Aside from using Indenoacridan Compound (1-7) synthesized in Example 6 to form a second hole transport layer 5b having a film thickness of 5 nm, an organic EL device was fabricated in the same way as in Example 50.

The layer construction of this organic EL device is shown in Table 2. The measured emission characteristics when direct-current voltage was applied to this organic EL device are shown in Table 4.

Comparative Example 1

An organic EL device was fabricated under the same conditions as in Example 38 except that the Arylamine Compound (5'-2) represented by the structural formula shown below was used to form a first hole transport layer 5a having a layer thickness of 60 nm and this Arylamine Compound (5'-2) was used to form a second hole transport layer 5b having a film thickness of 5 nm.

(5'-2)

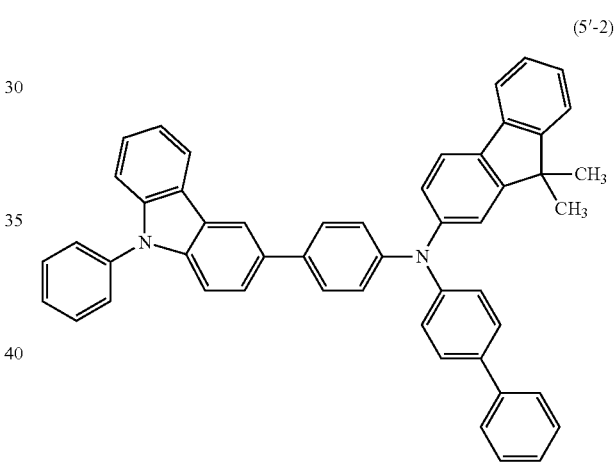

The layer construction of this organic EL device is shown in Table 2. The measured emission characteristics when direct-current voltage was applied to this organic EL device are shown in Table 4.

Comparative Example 2

An organic EL device was fabricated under the same conditions as in Example 44 except that the Arylamine Compound (5'-2) which was used in Comparative Example 1 was used to form a first hole transport layer 5a having a film thickness of 60 nm and a second hole transport layer 5b having a film thickness of 5 nm.

The layer construction of this organic EL device is shown in Table 2. The measured emission characteristics when direct-current voltage was applied to this organic EL device are shown in Table 4.

Comparative Example 3

An organic EL device was fabricated under the same conditions as in Example 50 except that the Arylamine Compound (5'-2) which was used in Comparative Example 1 was used to form a first hole transport layer 5a having a film thickness of 60 nm and a second hole transport layer 5b having a film thickness of 5 nm.

The layer construction of this organic EL device is shown in Table 2. The measured emission characteristics when direct-current voltage was applied to this organic EL device are shown in Table 4.

TABLE 1

| | First hole transport layer | Second hole transport layer | Luminous layer | Electron transport-layer |
|---|---|---|---|---|
| Example 38 | Cpd. 5-1 | Cpd. 1-1 | Cpd. 2-2/EMD-1 | Cpd. 4a-1/ETM-1 |
| Example 39 | Cpd. 5-1 | Cpd. 1-3 | Cpd. 2-2/EMD-1 | Cpd. 4a-1/ETM-1 |
| Example 40 | Cpd. 5-1 | Cpd. 1-4 | Cpd. 2-2/EMD-1 | Cpd. 4a-1/ETM-1 |
| Example 41 | Cpd. 5-1 | Cpd. 1-5 | Cpd. 2-2/EMD-1 | Cpd. 4a-1/ETM-1 |
| Example 42 | Cpd. 5-1 | Cpd. 1-6 | Cpd. 2-2/EMD-1 | Cpd. 4a-1/ETM-1 |
| Example 43 | Cpd. 5-1 | Cpd. 1-7 | Cpd. 2-2/EMD-1 | Cpd. 4a-1/ETM-1 |
| Example 44 | Cpd. 5-1 | Cpd. 1-1 | Cpd. 3-9/EMD-1 | Cpd. 4a-1/ETM-1 |
| Example 45 | Cpd. 5-1 | Cpd. 1-3 | Cpd. 3-9/EMD-1 | Cpd. 4a-1/ETM-1 |
| Example 46 | Cpd. 5-1 | Cpd. 1-4 | Cpd. 3-9/EMD-1 | Cpd. 4a-1/ETM-1 |
| Example 47 | Cpd. 5-1 | Cpd. 1-5 | Cpd. 3-9/EMD-1 | Cpd. 4a-1/ETM-1 |
| Example 48 | Cpd. 5-1 | Cpd. 1-6 | Cpd. 3-9/EMD-1 | Cpd. 4a-1/ETM-1 |
| Example 49 | Cpd. 5-1 | Cpd. 1-7 | Cpd. 3-9/EMD-1 | Cpd. 4a-1/ETM-1 |

Cpd.: Compound

TABLE 2

| | First hole transport layer | Second hole transport layer | Luminous layer | Electron transport-layer |
|---|---|---|---|---|
| Example 50 | Cpd. 5-1 | Cpd. 1-1 | Cpd. 3-16/EMD-1 | Cpd. 4a-1/ETM-1 |
| Example 51 | Cpd. 5-1 | Cpd. 1-3 | Cpd. 3-16/EMD-1 | Cpd. 4a-1/ETM-1 |
| Example 52 | Cpd. 5-1 | Cpd. 1-4 | Cpd. 3-16/EMD-1 | Cpd. 4a-1/ETM-1 |
| Example 53 | Cpd. 5-1 | Cpd. 1-5 | Cpd. 3-16/EMD-1 | Cpd. 4a-1/ETM-1 |
| Example 54 | Cpd. 5-1 | Cpd. 1-6 | Cpd. 3-16/EMD-1 | Cpd. 4a-1/ETM-1 |
| Example 55 | Cpd. 5-1 | Cpd. 1-7 | Cpd. 3-16/EMD-1 | Cpd. 4a-1/ETM-1 |
| Comparative Example 1 | Cpd. 5'-2 | Cpd. 5'-2 | Cpd. 2-2/EMD-1 | Cpd. 4a-1/ETM-1 |
| Comparative Example 2 | Cpd. 5'-2 | Cpd. 5'-2 | Cpd. 3-9/EMD-1 | Cpd. 4a-1/ETM-1 |
| Comparative Example 3 | Cpd. 5'-2 | Cpd. 5'-2 | Cpd. 3-16/EMD-1 | Cpd. 4a-1/ETM-1 |

Cpd.: Compound

TABLE 3

| | Voltage [V] (at 10 mA/cm$^2$) | Brightness [cd/m$^2$] (at 10 mA/cm$^2$) | Luminous efficiency [cd/A] (at 10 mA/cm$^2$) | Power efficiency [lm/W] (at 10 mA/cm$^2$) | Device life (97% attenuation) |
|---|---|---|---|---|---|
| Example 38 | 4.11 | 2693 | 26.96 | 20.60 | 134 hours |
| Example 39 | 4.1 | 2707 | 27.10 | 20.79 | 117 hours |
| Example 40 | 4.16 | 2602 | 26.04 | 19.68 | 131 hours |
| Example 41 | 4.16 | 2684 | 26.85 | 20.30 | 151 hours |
| Example 42 | 4.33 | 2607 | 26.10 | 18.61 | 197 hours |
| Example 43 | 4.4 | 2681 | 26.84 | 18.86 | 121 hours |
| Example 44 | 3.31 | 2588 | 25.92 | 24.61 | 148 hours |
| Example 45 | 3.3 | 2634 | 26.39 | 25.12 | 130 hours |
| Example 46 | 3.38 | 2513 | 25.15 | 23.39 | 169 hours |
| Example 47 | 3.39 | 2603 | 26.04 | 24.15 | 186 hours |
| Example 48 | 3.63 | 2501 | 25.06 | 22.20 | 196 hours |
| Example 49 | 3.67 | 2576 | 25.60 | 22.54 | 135 hours |

TABLE 4

| | Voltage [V] (at 10 mA/cm$^2$) | Brightness [cd/m$^2$] (at 10 mA/cm$^2$) | Luminous efficiency [cd/A] (at 10 mA/cm$^2$) | Power efficiency [lm/W] (at 10 mA/cm$^2$) | Device life (97% attenuation) |
|---|---|---|---|---|---|
| Example 50 | 3.82 | 2521 | 25.23 | 20.69 | 152 hours |
| Example 51 | 3.83 | 2514 | 25.15 | 20.68 | 162 hours |
| Example 52 | 3.87 | 2492 | 24.97 | 20.28 | 197 hours |
| Example 53 | 3.89 | 2466 | 24.69 | 19.94 | 150 hours |
| Example 54 | 4.13 | 2427 | 24.29 | 18.48 | 215 hours |
| Example 55 | 4.18 | 2501 | 25.03 | 18.62 | 155 hours |
| Comparative Example 1 | 4.03 | 2388 | 23.90 | 18.40 | 49 hours |
| Comparative Example 2 | 3.30 | 2267 | 22.69 | 21.52 | 44 hours |
| Comparative Example 3 | 3.79 | 2033 | 20.34 | 16.86 | 63 hours |

As is apparent from the above results, on comparing Examples 38 to 43 with Comparative Example 1 in which the luminous layer 6 was formed of the same material, the organic EL device of Comparative 1 had a luminous efficiency of 23.90 cd/A when an electric current was applied at a current density of 10 mA/cm$^2$, whereas the organic EL devices of Examples 38 to 43 all had higher luminous efficiencies of from 26.04 to 27.10 cd/A.

With regard to power efficiency as well, the organic EL device of Comparative Example 1 had a power efficiency of 18.40 lm/W, whereas the organic EL devices of Examples 38 to 43 all had higher power efficiencies of from 18.61 to 20.79 lm/W.

As for device life (97% attenuation), the organic EL device of Comparative Example 1 had a life of 49 hours, whereas the organic EL devices of Examples 38 to 43 had much longer lives of 117 to 197 hours.

Also, on comparing Examples 44 to 49 with Comparative Example 2 in which the luminous layer 6 was formed of the same material, the organic EL device of Comparative 2 had a luminous efficiency of 22.69 cd/A when an electric current was applied at a current density of 10 mA/cm$^2$, whereas the organic EL devices of Examples 44 to 49 all had higher luminous efficiencies of from 25.06 to 26.39 cd/A.

With regard to power efficiency, the organic EL device of Comparative Example 2 had a power efficiency of 21.52 lm/W, whereas the organic EL devices of Examples 44 to 49 all had higher power efficiencies of from 22.20 to 25.12 lm/W.

As for device life (97% attenuation), the organic EL device of Comparative Example 2 had a life of 44 hours, whereas the organic EL devices of Examples 44 to 49 had much longer lives of 130 to 196 hours.

In addition, on comparing Examples 50 to 55 with Comparative Example 3 in which the luminous layer 6 was formed of the same material, the organic EL device of Comparative 3 had a luminous efficiency of 20.34 cd/A when an electric current was applied at a current density of 10 mA/cm$^2$, whereas the organic EL devices of Examples 50 to 55 all had higher luminous efficiencies of from 24.29 to 25.23 cd/A.

With regard to power efficiency, the organic EL device of Comparative Example 3 had a power efficiency of 16.86 lm/W, whereas the organic EL devices of Examples 50 to 55 all had higher power efficiencies of from 18.48 to 20.69 lm/W. As for device life (97% attenuation), the organic EL device of Comparative Example 3 had a life of 63 hours, whereas the organic EL devices of Examples 50 to 55 had much longer lives of 150 to 215 hours.

In the organic EL devices of the invention, the carrier balance in the device is improved. In addition, because the hole transport layer material and the luminous layer material are combined in such a way as to provide a carrier balance suited to the properties of the emitting material, organic EL devices having a higher luminous efficiency and a longer life than conventional organic EL devices can be achieved.

INDUSTRIAL APPLICABILITY

The organic EL device of the invention exhibits a high luminous efficiency and also has an excellent durability, and thus is expected to be used in household appliances and lighting.

DESCRIPTION OF REFERENCE NUMERALS

1 Transparent substrate
2 Transparent anode
3 Hole injection layer
5 Hole transport layer
5a First hole transport layer
5b Second hole transport layer
6 Luminous layer
7 Electron transport layer
8 Electron injection layer
9 Cathode

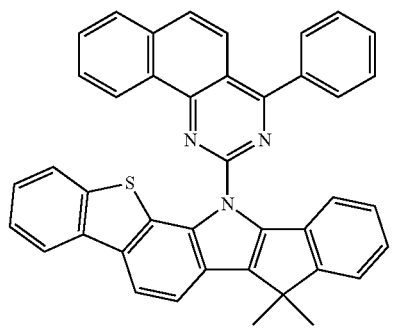

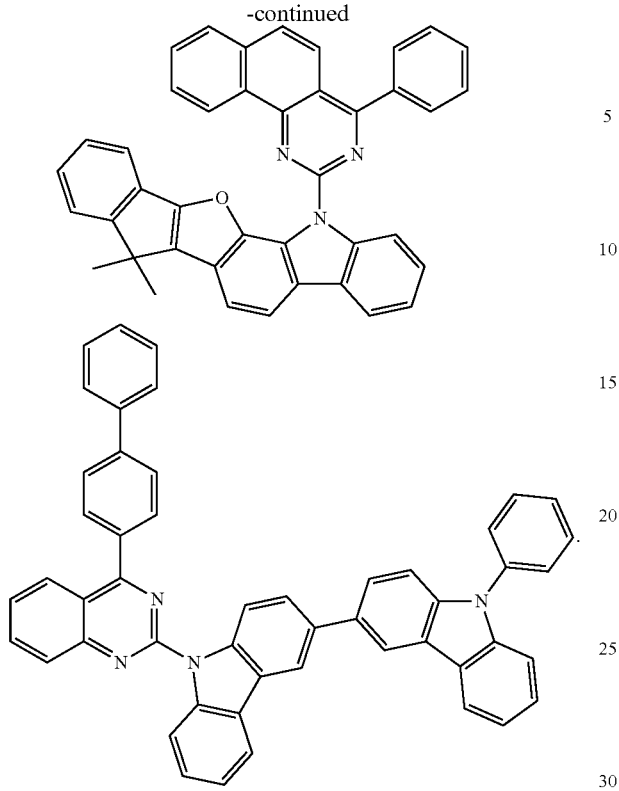

The invention claimed is:
1. An organic electroluminescent device comprising, in order, an anode, a hole transport layer, a luminous layer, an electron transport layer and a cathode, wherein the hole transport layer includes an indenoacridan derivative selected from the group consisting of:

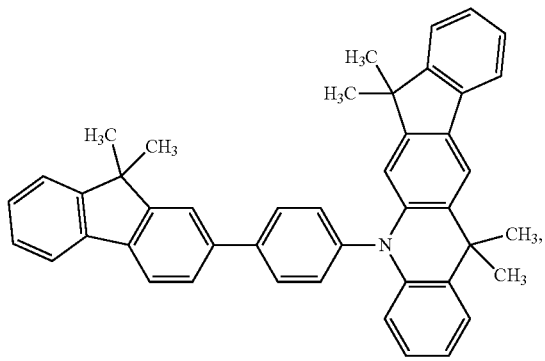

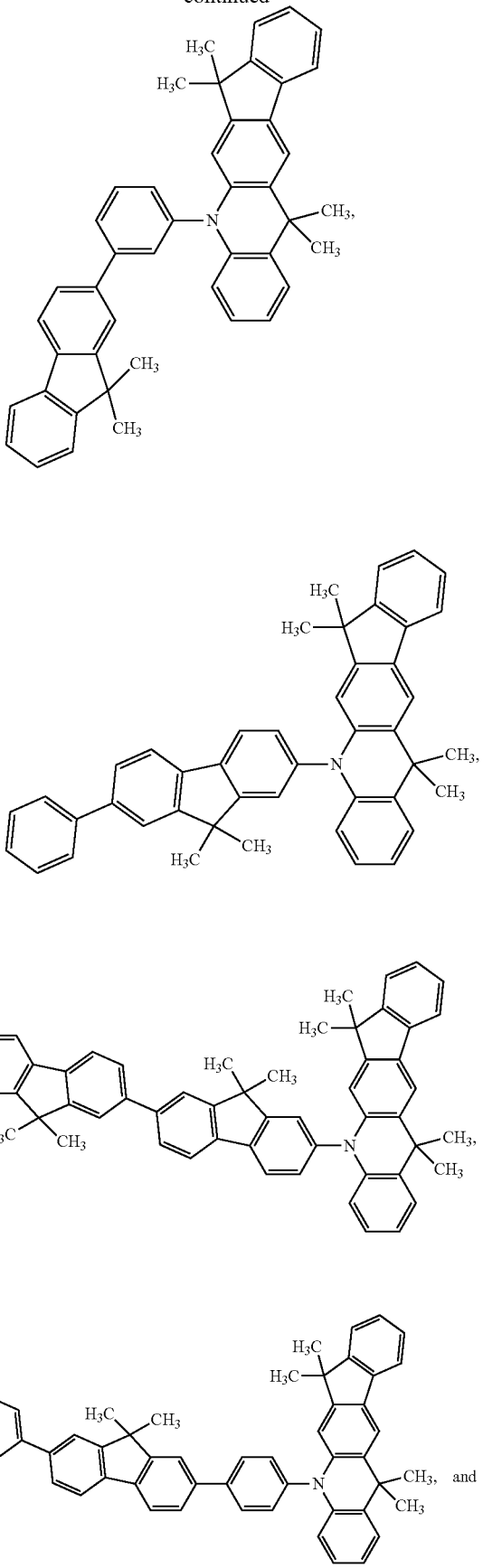

, and

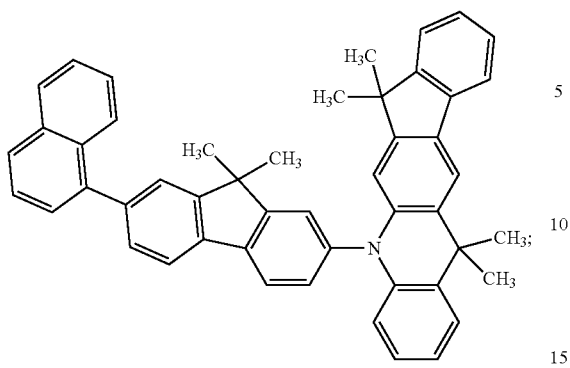
and the luminous layer includes at least one compound selected from the group consisting of:
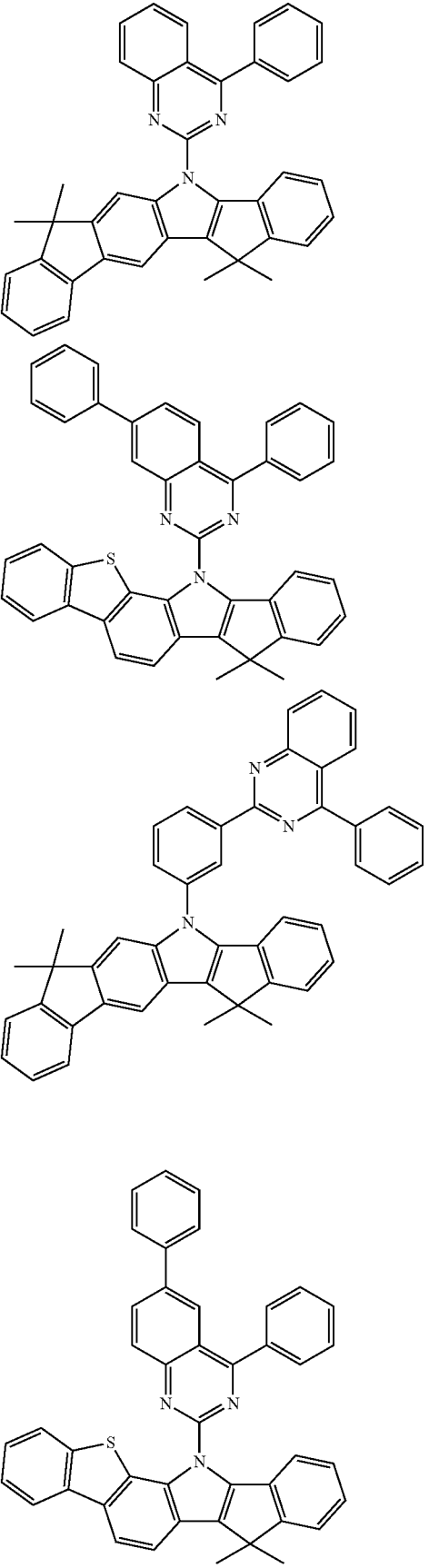

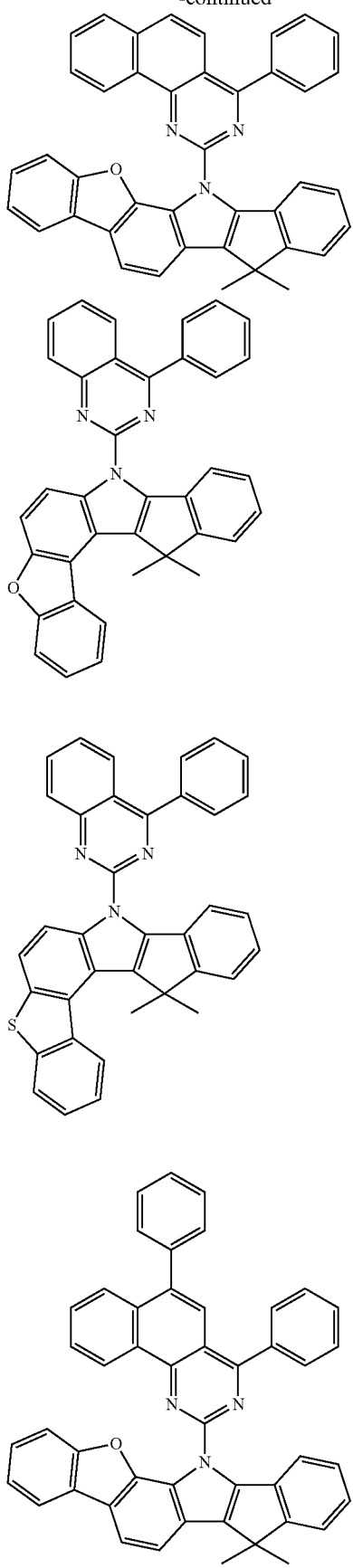
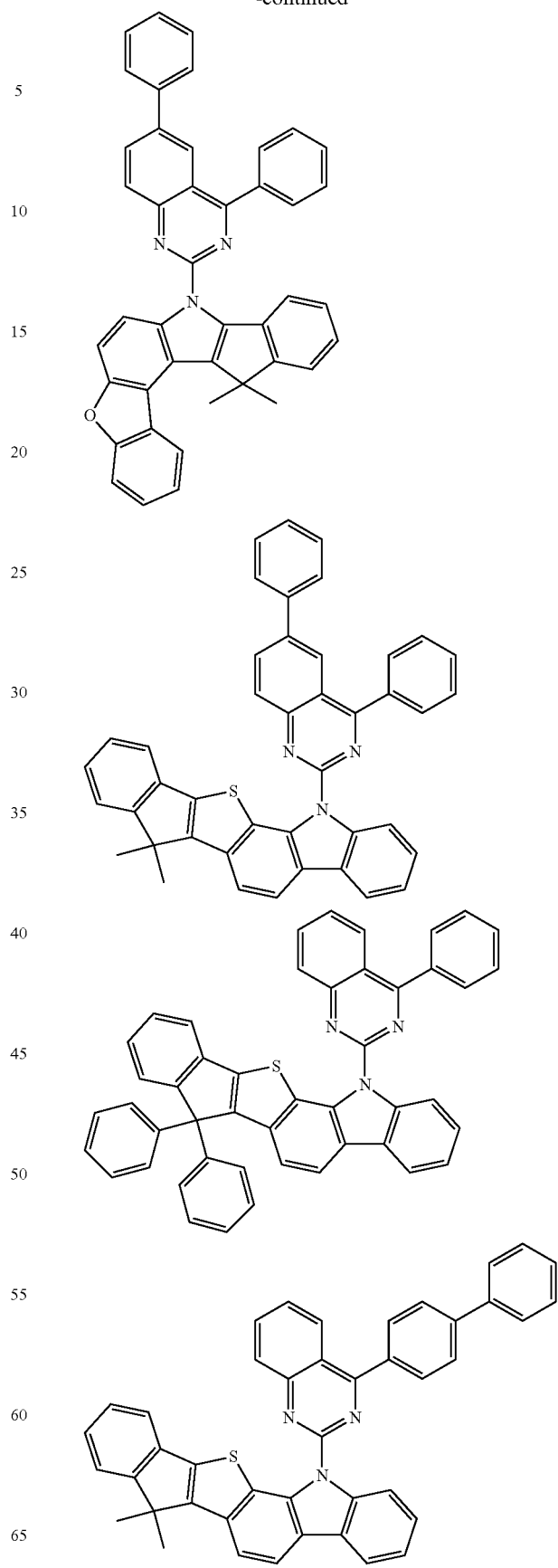

-continued

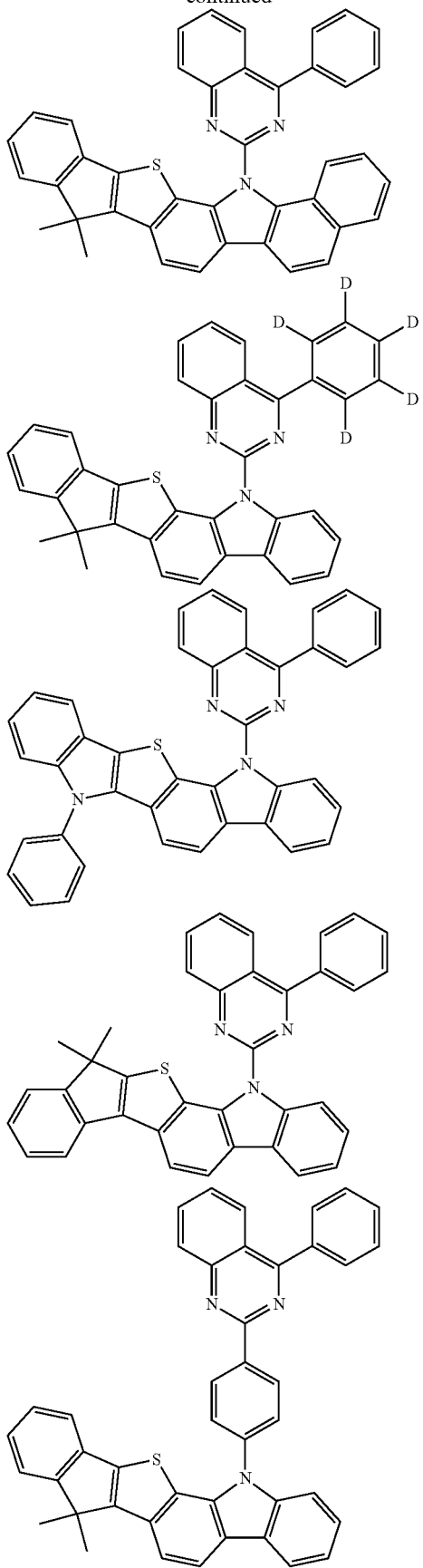

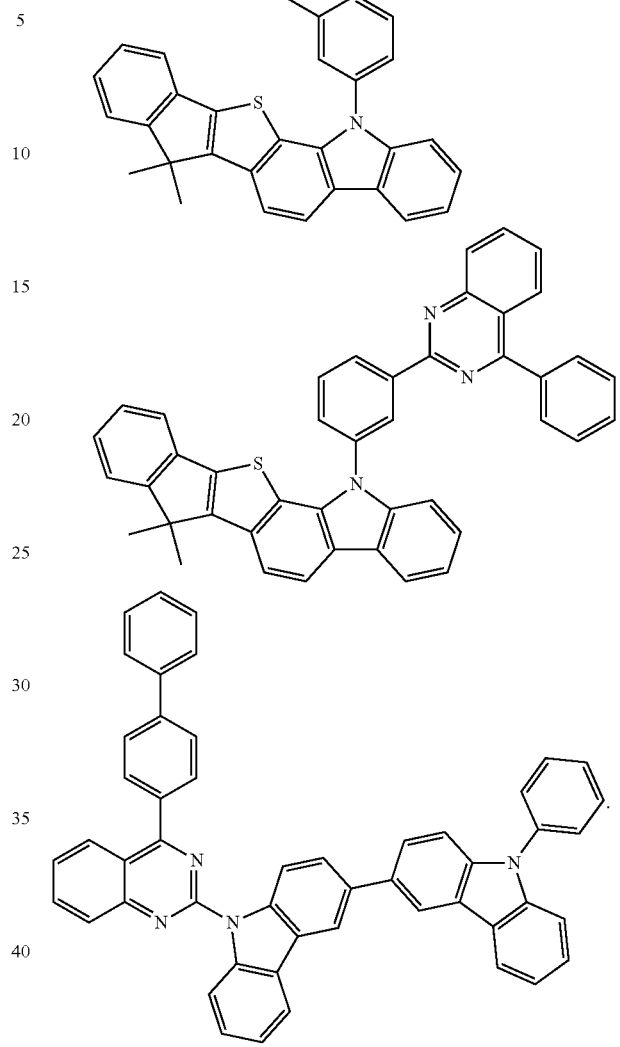

2. The organic electroluminescent device according to claim 1, wherein the electron transport layer includes an anthracene derivative represented by the following formula (4):

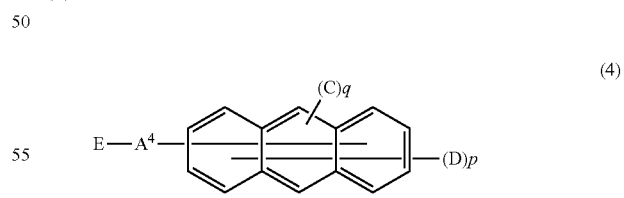

where
$A^4$ is a divalent aromatic hydrocarbon group, a divalent aromatic heterocyclic group or a single bond,
E is a monovalent aromatic heterocyclic group,
C is a monovalent aromatic hydrocarbon group or a monovalent aromatic heterocyclic group,
D is a hydrogen atom, a deuterium atom, a fluorine atom, a chlorine atom, a cyano group or an alkyl group having 1 to 6 carbon atoms, and p is an integer of 7 or 8 and q is an integer of 1 or 2, with the proviso that the sum of p and q is 9.

3. The organic electroluminescent device according to claim 2, wherein the anthracene derivative is represented by the following formula (4a):

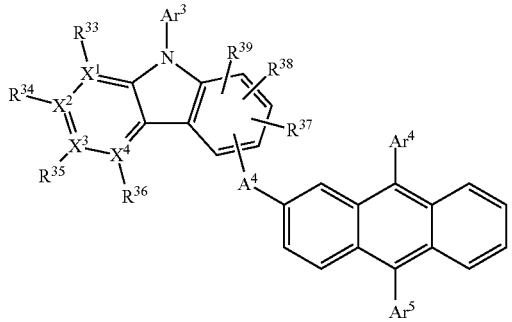

(4a)

where
A$^4$ is as defined in the formula (4),
Ar$^3$, Ar$^4$ and Ar$^5$ each represents a monovalent aromatic hydrocarbon group or a monovalent aromatic heterocyclic group,
R$^{33}$ to R$^{39}$ each represents a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, an aralkyl group or an aryloxy group, and may be bonded to each other via a single bond, a methylene group which may have a substituent, an oxygen atom or a sulfur atom to form a ring, and
X$^1$, X$^2$, X$^3$ and X$^4$ each represents a carbon atom or a nitrogen atom, provided that only one of these is a nitrogen atom, with none of R$^{33}$ to R$^{36}$, including hydrogen atoms, being bonded to the nitrogen atom.

4. The organic electroluminescent device according to claim 2, wherein the anthracene derivative is represented by the following formula (4b):

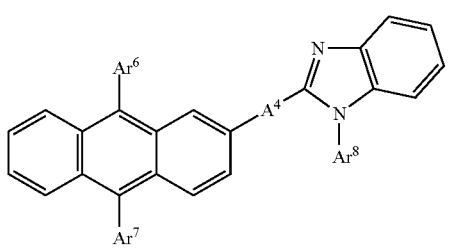

(4b)

where
A$^4$ is as defined in the formula (4), and
Ar$^6$, Ar$^7$, and Ar$^8$ each represents a monovalent aromatic hydrocarbon group or a monovalent aromatic heterocyclic group.

5. The organic electroluminescent device according to claim 2, wherein the anthracene derivative is represented by the following formula (4c):

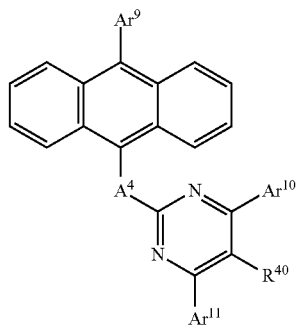

(4c)

where
A$^4$ is as defined in the formula (4),
Ar$^9$, Ar$^{10}$ and Ar$^{11}$ each represents a monovalent aromatic hydrocarbon group or a monovalent aromatic heterocyclic group, and
R$^{40}$ is a hydrogen atom, a deuterium atom, a fluorine atom, a chlorine atom, a cyano group, a nitro group, an alkyl group having 1 to 6 carbon atoms, a cycloalkyl group having 5 to 10 carbon atoms, an alkenyl group having 2 to 6 carbon atoms, an alkyloxy group having 1 to 6 carbon atoms, a cycloalkyloxy group having 5 to 10 carbon atoms, a monovalent aromatic hydrocarbon group, a monovalent aromatic heterocyclic group, an aralkyl group or an aryloxy group.

6. The organic electroluminescent device according to claim 1, wherein the hole transport layer has a two-layer structure including a first hole transport layer and a second hole transport layer, the second hole transport layer being positioned on the luminous layer side and includes the indenoacridan derivative.

7. The organic electroluminescent device according to claim 1, wherein the luminous layer further includes a phosphorescence emitting material.

8. The organic electroluminescent device according to claim 7, wherein the phosphorescence emitting material is a metal complex containing iridium or platinum.

9. The organic electroluminescent device according to claim 8, wherein the phosphorescence emitting material is a red-emitting dopant.

10. The organic electroluminescent device according to claim 1, wherein the luminous layer includes at least one compound selected from the group consisting of: